US01203573682

(12) United States Patent
Macur et al.

(10) Patent No.: US 12,035,736 B2
(45) Date of Patent: Jul. 16, 2024

(54) FOOD MATERIALS COMPRISING FILAMENTOUS FUNGAL PARTICLES AND MEMBRANE BIOREACTOR DESIGN

(71) Applicant: The Fynder Group, Inc., Chicago, IL (US)

(72) Inventors: Richard Eugene Macur, Manhattan, MT (US); Yuval Charles Avniel, Missoula, MT (US); Renata Usaite Black, Bozeman, MT (US); Maximilian DeVane Hamilton, Bozeman, MT (US); Michael John Harney, Bozeman, MT (US); Eleanore Brophy Eckstrom, Chicago, IL (US); Mark Andrew Kozubal, Bozeman, MT (US)

(73) Assignee: The Fynder Group, Inc., Chicago, IL (US)

( * ) Notice: Subject to any disclaimer, the term of this patent is extended or adjusted under 35 U.S.C. 154(b) by 0 days.

(21) Appl. No.: 18/368,001

(22) Filed: Sep. 13, 2023

(65) Prior Publication Data

US 2024/0023587 A1    Jan. 25, 2024

Related U.S. Application Data

(60) Continuation of application No. 18/349,687, filed on Jul. 10, 2023, which is a continuation of application
(Continued)

(51) Int. Cl.
*A23L 31/10* (2016.01)
*A21D 13/04* (2017.01)
(Continued)

(52) U.S. Cl.
CPC .............. *A23L 31/10* (2016.08); *A21D 13/04* (2013.01); *A21D 13/064* (2013.01); *A21D 13/44* (2017.01);
(Continued)

(58) Field of Classification Search
CPC ....... A23L 31/10; A23L 33/195; A23C 9/123; A23C 19/0325; A23C 19/0326; A23C 19/0323
(Continued)

(56) References Cited

U.S. PATENT DOCUMENTS 2,450,055 A * 9/1948 Nord ..................... A23J 3/20
426/72
4,041,189 A * 8/1977 Towersey ................ A23J 3/20
435/270
(Continued)

FOREIGN PATENT DOCUMENTS

TW         201741453       12/2017
WO       WO 00/015045       3/2000

OTHER PUBLICATIONS

U.S. Appl. No. 18/349,687, filed Jul. 10, 2023, Macur et al.
(Continued)

*Primary Examiner* — Hamid R Badr
(74) *Attorney, Agent, or Firm* — Sheridan Ross P.C.

(57) ABSTRACT

Methods of production of edible filamentous fungal biomat formulations are provided as standalone protein sources and/or protein ingredients in foodstuffs as well as a one-time use or repeated use self-contained biomat reactor comprising a container with at least one compartment and placed within the compartment(s), a feedstock, a fungal inoculum, a gas-permeable membrane, and optionally a liquid nutrient medium.

30 Claims, 23 Drawing Sheets

Related U.S. Application Data

No. 17/946,772, filed on Sep. 16, 2022, now Pat. No. 11,723,392, which is a continuation of application No. 17/694,604, filed on Mar. 14, 2022, now Pat. No. 11,478,007, which is a continuation of application No. 17/323,918, filed on May 18, 2021, now Pat. No. 11,272,726, which is a division of application No. 16/842,738, filed on Apr. 7, 2020, now Pat. No. 11,039,635, which is a continuation of application No. 16/803,667, filed on Feb. 27, 2020, now Pat. No. 11,432,575.

(60) Provisional application No. 62/811,421, filed on Feb. 27, 2019.

(51) Int. Cl.

| | |
|---|---|
| A21D 13/064 | (2017.01) |
| A21D 13/44 | (2017.01) |
| A23C 9/123 | (2006.01) |
| A23C 9/13 | (2006.01) |
| A23C 11/10 | (2021.01) |
| A23C 19/032 | (2006.01) |
| A23G 9/32 | (2006.01) |
| A23G 9/36 | (2006.01) |
| A23G 9/38 | (2006.01) |
| A23G 9/42 | (2006.01) |
| A23J 1/00 | (2006.01) |
| A23J 3/20 | (2006.01) |
| A23J 3/22 | (2006.01) |
| A23L 13/40 | (2023.01) |
| A23L 13/60 | (2016.01) |
| A23L 29/00 | (2016.01) |
| A23L 29/30 | (2016.01) |
| A23L 31/00 | (2016.01) |
| A23L 33/135 | (2016.01) |
| A23L 33/195 | (2016.01) |
| C12M 1/00 | (2006.01) |
| C12M 1/04 | (2006.01) |
| C12M 1/12 | (2006.01) |
| C12N 1/14 | (2006.01) |

(52) U.S. Cl.
CPC ............ *A23C 9/123* (2013.01); *A23C 9/1315* (2013.01); *A23C 11/10* (2013.01); *A23C 19/0323* (2013.01); *A23C 19/0325* (2013.01); *A23C 19/0326* (2013.01); *A23G 9/32* (2013.01); *A23G 9/363* (2013.01); *A23G 9/38* (2013.01); *A23G 9/42* (2013.01); *A23J 1/008* (2013.01); *A23J 3/20* (2013.01); *A23J 3/227* (2013.01); *A23L 13/428* (2016.08); *A23L 13/46* (2016.08); *A23L 13/65* (2016.08); *A23L 29/065* (2016.08); *A23L 29/30* (2016.08); *A23L 31/00* (2016.08); *A23L 33/135* (2016.08); *A23L 33/195* (2016.08); *C12M 21/00* (2013.01); *C12M 23/14* (2013.01); *C12M 23/24* (2013.01); *C12M 23/40* (2013.01); *C12M 25/02* (2013.01); *C12M 25/14* (2013.01); *C12N 1/14* (2013.01); *A23V 2002/00* (2013.01)

(58) Field of Classification Search
USPC .......................................................... 426/37
See application file for complete search history.

(56) References Cited

U.S. PATENT DOCUMENTS

| | | |
|---|---|---|
| 2012/0076909 A1 | 3/2012 | Waldner |
| 2017/0020166 A1 | 1/2017 | Keys et al. |
| 2017/0188612 A1* | 7/2017 | Varadan .................. A23L 13/43 |

OTHER PUBLICATIONS

Zapata et al., "Testing the Potential of Using Fungi to Convert Human Waste Into Protein," Faculty Presentation at Valparaiso University Department of Biology, Jan. 1, 2011, pp. 1-2.
Official Action for U.S. Appl. No. 18/349,687, dated Sep. 26, 2023, 8 pages.
Official Action for U.S. Appl. No. 17/882,488, dated Oct. 4, 2023, 12 pages.
Official Action for U.S. Appl. No. 18/364,676, dated Nov. 16, 2023, 11 pages.
Okamura et al., "The artificial Cultivation of Isolants Pleurotus ostreatus and Their Application as Food Ingredient in Extrusion Cooking," Journal of Cookery Science of Japan, vol. 31, No. 1, 1998, pp. 7-14.
Ulziijargal et al., "Quality of bread supplemented with mushroom mycelia," Food Chemistry, vol. 138, 2013, pp. 70-76.
Notice of Allowance for U.S. Appl. No. 18/364,676, dated Mar. 6, 2024, 8 pages.
Official Action for U.S. Appl. No. 18/446,936, dated Dec. 5, 2023, 8 pages.
Official Action for U.S. Appl. No. 18/446,936, dated Mar. 6, 2024, 11 pages.
Official Action for U.S. Appl. No. 18/478,496, dated Jan. 17, 2024, 7 pages.
Official Action for U.S. Appl. No. 18/478,562, dated Jan. 25, 2024, 8 pages.
Official Action for U.S. Appl. No. 18/534,119, dated Mar. 1, 2024, 8 pages. Restriction Requirement.

* cited by examiner

| Sample concentration | H₂O | 0.00825% (1000X) | 0.0825% (100X) | 0.825% (10X) |
|---|---|---|---|---|
| Looks | | | | |
| Refractive index | 1.3318 ± 0.002 | 1.3319 ± 0.002 | 1.3322 ± 0.001 | 1.3340 ± 0.002 |
| Density | 0.9957 g/cm³ | 0.9957 g/cm³ | 0.9957 g/cm³ | 0.9972 g/cm³ |
| Particle size | | Num. avg.: 4267 nm<br>PDI: 1<br>Count rate: 251 cps | Num. avg.: 5590 nm<br>PDI: 1<br>Count rate: 255 cps | Num. avg.: 5277 nm<br>PDI: 1<br>Count rate: 252 cps |
FIG. 20
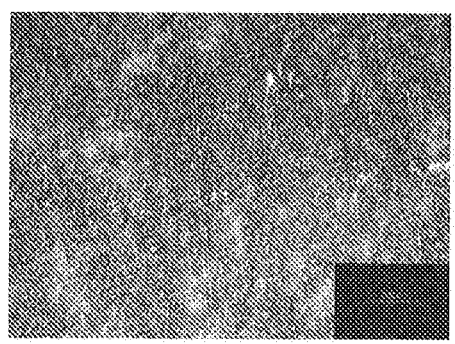 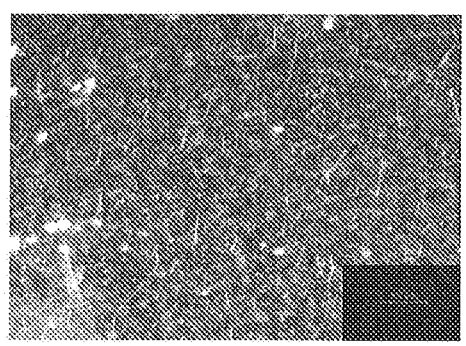
FIG. 21A    FIG. 21B

FOOD MATERIALS COMPRISING FILAMENTOUS FUNGAL PARTICLES AND MEMBRANE BIOREACTOR DESIGN

CROSS-REFERENCE TO RELATED APPLICATION

This application is a continuation of U.S. patent application Ser. No. 18/349,687, filed 10 Jul. 2023, which is a continuation of U.S. patent application Ser. No. 17/946,772, filed 16 Sep. 2022, now U.S. Pat. No. 11,723,392, which is a continuation of U.S. patent application Ser. No. 17/694,604, filed 14 Mar. 2022, and now issued as U.S. Pat. No. 11,478,007, which is a continuation of U.S. patent application Ser. No. 17/323,918, filed 18 May 2021 and now issued as U.S. Pat. No. 11,272,726, which is a divisional of U.S. patent application Ser. No. 16/842,738, filed 7 Apr. 2020 and now issued as U.S. Pat. No. 11,039,635, which is a continuation of U.S. patent application Ser. No. 16/803,667, filed 27 Feb. 2020 and now issued as U.S. Pat. No. 11,432,575, which claims the benefit of priority of U.S. Provisional Patent Application 62/811,421, filed 27 Feb. 2019, the entireties of all of which are incorporated herein by reference.

TECHNICAL FIELD

This application relates to edible filamentous fungi and provides methods of preparing edible fungi for use in foodstuffs, liquid and solid formulations of edible fungi, as well as uses and methods associated therewith, foodstuffs containing edible filamentous fungi, and methods and uses thereof.

BACKGROUND

The United Nations listed the world population as 7.5 billion in August 2017 and predicts that figure to grow to 8 billion in 2023 and to be 10 billion in 2056. In a related report, the Food and Agricultural Organization of the United Nations (FAO) estimates that if the global population reaches 9.1 billion by 2050, world food production will need to rise by 70% and to double in the developing world. That increase in food production will need to occur despite rising energy costs, decreasing underground aquifer resources, loss of farmland to urban sprawl, and increasingly severe weather due to climate change (e.g. increased temperatures, increased drought, increased flooding, etc.). This is a particular challenge for countries such as Africa which, according to 2009 figures, already has inadequate protein intake and countries such as China, India, Pakistan, and Indonesia which are at risk of inadequate protein intake. In addition, the global demand is forecasted for 2040 to increase by 60% for meat and 50% for dairy.

But not all protein sources are created equal. Animal-based foods (meat, eggs, dairy) provide "complete" proteins as they contain all of the essential amino acids; that is, methionine, leucine, isoleucine, phenylalanine, valine, threonine, histidine, tryptophan and lysine. Plant-based foods, while containing some essential amino acids, generally lack the complete set. For example, the protein found in starchy roots lacks the essential amino acid lysine, which must then be obtained from another food in the diet. Beans and legumes contain high levels of lysine, but they lack the essential amino acid methionine. Although it is possible to build a complete protein by pairing plant foods, ensuring a nutritionally balanced diet is much easier with complete proteins.

One non-animal source of complete protein is obtained from edible filamentous fungi, such as *Fusarium venenatum* (formerly classified and *Fusarium graminearum*). However, to date protein production from these sources has required significant investment in energy resources and production equipment, such as capital-intensive bioreactors and centrifuges. There remains a need for growth, harvesting, and foodstuff production methods that require low energy, consume few natural resources, and are low cost. The current invention solves these problems.

In addition, one area of reducing the logistics supply associated with responding to natural disasters, logistically isolated environments or military and/or space/extraterrestrial missions is the closure of life support loops, particularly waste streams, while providing mission critical products such as nutritional and appetizing foods, fuels, metabolite expression platforms, building materials and/or microbial factories. Oftentimes these types of environments have no or limited access to sterile facilities and/or require a sealed aseptic system to fully contain the waste stream and/or food, fuel and materials produced. For example, work by the European Space Agency (Expeditions 25-28, Growth and Survival of Colored Fungi in Space (CFS-A)) demonstrated that fungi can grow inside the space station and could decompose food and other organic materials in humid conditions; here containment of the fungal system is paramount to preventing inadvertent contamination of other supplies and surfaces. In addition to the need to decompose food and waste in the developing area of space travel, these needs are also present when dealing with natural disasters, in-theater military operations, wilderness operations, situations in the third world where sanitation and refrigeration are not reliable, confined spaces, logistically difficult arenas and in some agricultural/industrial operations. Having a self-contained aseptic system that operates efficiently with a minimum of space, energy, and maintenance is needed.

A robust and efficient portable self-contained biomat reactor system that is able to convert a wide variety of waste streams into a multitude of valuable products addresses these problems. The current disclosure describes a simple aseptic bioreactor platform that requires no agitation, no active aeration, no external energy source during fermentation (other than temperature control), generates minimal to no waste residues, requires little water, and produces dense, easily harvested, textured biomats. In addition, the self-contained biomat reactor system can be portable and/or scalable for larger, more concentrated missions and/or populations.

SUMMARY

It is one aspect of the present invention to provide a food material, comprising particles of a filamentous fungus belonging to an order selected from the group consisting of Mucorales Ustilaginales, Russulales, Polyporales, Agaricales, Pezizales and Hypocreales, wherein the filamentous fungus comprises greater than about 40 wt. % protein content and less than about 8 wt. % RNA content.

In embodiments, the filamentous fungus may belong to a family selected from the group consisting of Mucoraceae, Ustilaginaceae, Hericiaceae, Polyporaceae, Grifolaceae, Lyophyllaceae, Strophariaceae, Lycoperdaceae, Agaricaceae, Pleurotaceae, Physalacriaceae, Omphalotaceae, Tuberaceae, Morchellaceae, Sparassidaceae, Nectriaceae, Bionectriaceae, and Cordycipitaceae.

In embodiments, the filamentous fungus may belong to a species selected from the group consisting of *Rhizopus oligosporus*, *Ustilago esculenta*, *Hericululm erinaceus*, *Polyporous squamosus*, *Grifola fondrosa*, *Hypsizygus marmoreus*, *Hypsizygus ulmarius* (elm oyster) *Calocybe gambosa*, *Pholiota nameko*, *Calvatia gigantea*, *Agaricus bisporus*, *Stropharia rugosoannulata*, *Hypholoma lateritium*, *Pleurotus eryngii*, *Pleurotus ostreatus* (pearl), *Pleurotus ostreatus* var. *columbinus* (Blue oyster), *Tuber borchii*, *Morchella esculenta*, *Morchella conica*, *Morchella importuna*, *Sparassis crispa* (cauliflower), *Fusarium venenatum*, strain MK7 (ATCC Accession Deposit No. PTA-10698), *Disciotis venosa*, *Clonostachys rosea*, *Cordyceps mihtaris*, *Trametes versicolor*, *Ganoderma lucidum*, *Flammulina velutipes*, *Lentinula edodes*, *Pleurotus djamor*, *Pleurotus ostreatus*, and *Leucoagaricus* spp.

In embodiments, the filamentous fungus may be a *Fusarium* species.

In embodiments, the filamentous fungus may be *Fusarium venenatum*.

In embodiments, the filamentous fungus may be strain MK7 (ATCC Accession Deposit No. PTA-10698).

In embodiments, the filamentous fungus may have a characteristic selected from the group consisting of (a) comprising greater than about 45 wt. % protein content; (b) comprising greater than about 50 wt. % protein content; (c) comprising greater than about wt. % protein content; (d) comprising greater than about 60 wt. % protein content; (e) comprising less than about 5 wt. % RNA content; (f) comprising less than about 4 wt. % RNA content; (g) comprising less than about 3 wt. % RNA content; (h) comprising less than about 2 wt. % RNA content; and combinations of one of a-d and one of e-h.

In embodiments, the filamentous fungus may comprise less than about 10 ppm of a mycotoxin selected from the group consisting of Alfatoxin B1, Alfatoxin B2, Alfatoxin G1, Alfatoxin G2, Fumonisin B1, Fumonisin B2, Fumonisin B3, Ochratoxin A, Nivalenol, Deoxynivalenol, Acetyl deoxynivalenol, Fusarenon X, T-2 Toxin, HT-2 Toxin, Neosolaniol, Diacetoxyscirpenol zearalenone, beauvericin, fusarin C, fusaric acid, and any combinations thereof.

The filamentous fungus may comprise less than about 10 ppm, or less than about 9 ppm, or less than about 8 ppm, or less than about 7 ppm, or less than about 6 ppm, or less than about 5 ppm, or less than about 4 ppm, or less than about 3 ppm, or less than about 2 ppm, or less than about 1 ppm, or less than about 0.9 ppm, or less than about 0.8 ppm, or less than about 0.7 ppm, or less than about 0.6 ppm of the selected mycotoxin, or alternatively less than about any tenth of a part per million equal to or less than 10 ppm. In particular embodiments, the selected mycotoxin may be a fumonisin or combination of fumonisins, beauvericin, fusarin C, fusaric acid, and combinations thereof.

In embodiments, the filamentous fungus may comprise less than about 10 ppm total mycotoxin content, or less than about 9 ppm total mycotoxin content, or less than about 8 ppm total mycotoxin content, or less than about 7 ppm total mycotoxin content, or less than about 6 ppm total mycotoxin content, or less than about 5 ppm total mycotoxin content, or less than about 4 ppm total mycotoxin content, or less than about 3 ppm total mycotoxin content, or less than about 2 ppm total mycotoxin content, or less than about 1 ppm total mycotoxin content, or less than about 0.9 ppm total mycotoxin content, or less than about ppm total mycotoxin content, or less than about 0.7 ppm total mycotoxin content, or less than about 0.6 ppm total mycotoxin content, or alternatively less than about any tenth of a part per million equal to or less than 10 ppm total mycotoxin content.

In embodiments, the filamentous fungus may comprise greater than about 15 wt. % of branched chain amino acids.

In embodiments, the particles of filamentous fungus may be in the form of a flour. The flour may, but need not, have a particle size of from 30-400 microns. The flour may, but need not, have a particle size of no more than about 400 microns, no more than about 390 microns, no more than about 380 microns, no more than about 370 microns, no more than about 360 microns, no more than about 350 microns, no more than about 340 microns, no more than about 330 microns, no more than about 320 microns, no more than about 310 microns, no more than about 300 microns, no more than about 290 microns, no more than about 280 microns, no more than about 270 microns, no more than about 260 microns, no more than about 250 microns, no more than about 240 microns, no more than about 230 microns, no more than about 220 microns, no more than about 210 microns, no more than about 200 microns, no more than about 190 microns, no more than about 180 microns, no more than about 170 microns, no more than about 160 microns, no more than about 150 microns, no more than about 140 microns, no more than about 130 microns, no more than about 120 microns, no more than about 110 microns, no more than about 100 microns, no more than about 90 microns, no more than about 80 microns, no more than about 70 microns, no more than about 60 microns, no more than about 50 microns, no more than about 40 microns, no more than about 30 microns, no more than about 20 microns, no more than about 10 microns, no more than about 9 microns, no more than about 8 microns, no more than about 7 microns, no more than about 6 microns, no more than about 5 microns, no more than about 4 microns, no more than about 3 microns, no more than about 2 microns, or no more than about 1 micron, or alternatively no more than about any whole number of microns between about 1 micron and about 400 microns. The particle size may be any one or more of a $D_{10}$ particle size, a $D_{25}$ particle size, a $D_{50}$ particle size, a $D_{75}$ particle size, a $D_{90}$ particle size, or a weight-average particle size. In some embodiments, substantially all particles may have a particle size of at least about 30 microns and no more than about 400 microns.

In embodiments, the particles may have a particle length of about 0.05 mm to about 500 mm, a particle width of about 0.03 mm to about 7 mm, and a particle height of about mm to about 1.0 mm. The particles may, but need not, have a particle length, a particle width, and a particle height that are all more than about 0.02 mm, more than about 0.03 mm, more than about 0.04 mm, more than about 0.05 mm, more than about 0.06 mm, more than about 0.07 mm, more than about 0.08 mm, more than about 0.09 mm, more than about 0.10 mm, more than about 0.11 mm, more than about 0.12 mm, more than about 0.13 mm, more than about 0.14 mm, more than about 0.15 mm, more than about 0.16 mm, more than about mm, more than about 0.18 mm, more than about 0.19 mm, or more than about 0.20 mm, or alternatively more than about any whole number of microns that is at least about 20 microns.

In embodiments, the food material may be a liquid dispersion of the particles of filamentous fungus. The liquid dispersion may, but need not, be produced under nitrogen. The liquid dispersion of the particles of filamentous fungus may, but need not, be stable for at least about 1 day.

In embodiments, the food material may be vegan.

In embodiments, the particles of filamentous fungus may be the sole protein component present in the food material.

In embodiments, the particles of filamentous fungus may comprise all essential amino acids. The particles of filamentous fungus may, but need not, comprise at least one branched-chain amino acid selected from the group consisting of leucine, isoleucine, and valine.

In embodiments, the filamentous fungal particles may be nonviable.

It is another aspect of the present invention to provide a yogurt analog food product comprising particles of a filamentous fungus belonging to an order selected from the group consisting of Mucorales, Ustilaginales, Russulales, Polyporales, Agaricales, Pezizales and Hypocreales, wherein the filamentous fungus comprises greater than about 40 wt. % protein content and less than about 8 wt. % RNA content.

In embodiments, the filamentous fungus may belong to a family selected from the group consisting of Mucoraceae, Ustilaginaceae, Hericiaceae, Polyporaceae, Grifolaceae, Lyophyllaceae, Strophariaceae, Lycoperdaceae, Agaricaceae, Pleurotaceae, Tuberaceae, Morchellaceae, Sparassidaceae, Physalacriaceae, Omphalotaceae, Nectriaceae, Bionectriaceae, and Cordycipitaceae.

In embodiments, the filamentous fungus may belong to a species selected from the group consisting of *Rhizopus oligosporus, Ustilago esculenta, Hericululm erinaceus, Polyporous squamosus, Grifola fondrosa, Hypsizygus marmoreus, Hypsizygus ulmarius* (elm oyster) *Calocybe gambosa, Pholiota nameko, Calvatia gigantea, Agaricus bisporus, Stropharia rugosoannulata, Hypholoma lateritium, Pleurotus eryngii, Pleurotus ostreatus* (pearl), *Pleurotus ostreatus* var. *columbinus* (Blue oyster), *Tuber borchii, Morchella esculenta, Morchella conica, Morchella importuna, Sparassis crispa* (cauliflower), *Fusarium venenatum*, strain MK7 (ATCC Accession Deposit No. PTA-10698), *Disciotis venosa, Clonostachys rosea, Cordyceps militaris, Trametes versicolor, Ganoderma lucidum, Flammulina velutipes, Lentinula edodes, Pleurotus djamor, Pleurotus ostreatus*, and *Leucoagaricus* spp.

In embodiments, the filamentous fungus may be a *Fusarium* species.

In embodiments, the filamentous fungus may be *Fusarium venenatum*.

In embodiments, the filamentous fungus may be strain MK7 (ATCC Accession Deposit No. PTA-10698).

In embodiments, the filamentous fungus may have a characteristic selected from the group consisting of (a) comprising greater than about 45 wt. % protein content; (b) comprising greater than about 50 wt. % protein content; (c) comprising greater than about wt. % protein content; (d) comprising greater than about 60 wt. % protein content; (e) comprising less than about 5 wt. % RNA content; (f) comprising less than about 4 wt. % RNA content; (g) comprising less than about 3 wt. % RNA content; (g) comprising less than about 2 wt. % RNA content; and combinations of one of a-d and one of e-h.

In embodiments, the ratio of the filamentous fungal particles to water may range from about 1:10 to about 10:1.

In embodiments, the ratio of the filamentous fungal particles to water may be selected from the group consisting of about 1:3, about 1:2, about 1:1 and about 2:1.

In embodiments, the yogurt analog food product may further comprise an invert sugar.

In embodiments, the yogurt analog food product may further comprise a thickening agent.

In embodiments, cells of the filamentous fungus may be lysed.

In embodiments, the yogurt analog food product may further comprise *Lactobacillus bulgaricus* and *Streptococcus thermophilus*.

In embodiments, the product may be vegan.

In embodiments, the filamentous fungal particles may comprise all essential amino acids.

In embodiments, the filamentous fungal particles may be the sole protein component.

In embodiments, the filamentous fungal particles may be nonviable.

In embodiments, the yogurt analog food product may further comprise a rennet. The rennet may, but need not, be from a source selected from the group consisting of an animal source, a vegetarian source and a microbial source. The rennet may, but need not, be from a source selected from the group consisting of a vegetarian source and a microbial source.

In embodiments, the product may be free of milk solids.

In embodiments, the yogurt analog food product may further comprise a probiotic.

In embodiments, the yogurt analog food product may further comprise an enzymatic water.

It is another aspect of the present invention to provide a foam material, comprising particles of a filamentous fungal biomat; and a liquid phase, wherein the solids content of the foam material is between about 5% and about 30%, and wherein the foam is stable. The liquid phase may, but need not, be an aqueous phase, i.e. comprise water.

In embodiments, the foam material may not collapse spontaneously immediately upon cessation of the foaming process during its production.

In embodiments, the foam material may be stable for at least about 7 days.

In embodiments, the foam material may have an overrun of at least about 10%.

In embodiments, the filamentous fungal biomat may comprise a *Fusarium* species.

In embodiments, the foam material may be free of milk solids.

It is another aspect of the present invention to provide a food product comprising the foam material.

It is another aspect of the present invention to provide a bioreactor, comprising a container; at least one membrane disposed within or on a surface of the container, the at least one membrane comprising a first surface and a second surface; a feedstock for the growth of a filamentous fungus, contacting the first surface of the at least one membrane; and a filamentous fungus inoculum, disposed on either the first surface or the second surface of the at least one membrane, wherein, upon culturing the inoculum in the bioreactor, a biomat of the filamentous fungus forms on the second surface of the at least one membrane after a biomat growth period. As used herein, the term "membrane," unless otherwise specified, refers to any flexible or semi-flexible enclosing or separating part that forms a plane or film and separates two environments, and that has pores therethrough enabling exchange of at least a portion of a fluid between the two environments.

In embodiments, the container may be a bag, wherein the first and second surfaces of the at least one membrane are first and second surfaces of at least a portion of the bag.

In embodiments, the feedstock may be subjected to a positive or negative pressure imparted on a side of the feedstock opposite at least one of the first surface and the second surface of the at least one membrane.

In embodiments, the bioreactor may further comprise cyanobacteria, wherein the cyanobacteria provide at least one of oxygen gas and carbon to promote the growth of the biomat.

In embodiments, at least one of the following may be true: i) a density of the biomat is at least about 0.05 grams per cubic centimeter; and ii) a density of the biomat after drying is at least about 0.01 grams per cubic centimeter.

In embodiments, the biomat may comprise at least one layer.

In embodiments, the biomat may have a tensile strength of at least about 3 kilopascals or at least about 30 grams-force per square centimeter. The biomat may, but need not, have a tensile strength of at least about 100 kilopascals or at least about 1,020 grams-force per square centimeter.

In embodiments, the at least one membrane may comprise at least one polymer selected from the group consisting of polypropylenes, polytetrafluoroethylenes, polycarbonates, polyamides, cellulose acetate, polyvinylidene fluorides, mixed cellulose esters, polyethersulfones, polyethylenes, and polypyrroles.

In embodiments, the at least one membrane may comprise at least one material selected from the group consisting of polypropylene fabrics, polytetrafluoroethylene fabrics, and a nylon net filter.

In embodiments, the at least one membrane may comprise at least one of a glass fiber material and a porous ceramic material.

In embodiments, an average pore size of the at least one membrane may be between about 0.2 µm and about 25 µm. The average pore size of the at least one membrane may, but need not, be between about 5 µm and about 11 µm.

In embodiments, the container may be enclosed and substantially airtight, wherein the container encloses a gas headspace into which the biomat grows.

In embodiments, the biomat may separate from the at least one membrane spontaneously.

In embodiments, when the biomat is removed from the at least one membrane, a new inoculum of filamentous fungi may remain on the at least one membrane.

In embodiments, the filamentous fungus may belong to an order selected from the group consisting of Mucorales, Ustilaginales, Russulales, Polyporales, Agaricales, Pezizales, and Hypocreales.

In embodiments, the filamentous fungus may belong to a family selected from the group consisting of Mucoraceae, Ustilaginaceae, Hericiaceae, Polyporaceae, Grifolaceae, Lyophyllaceae, Strophariaceae, Lycoperdaceae, Agaricaceae, Pleurotaceae, Physalacriaceae, Omphalotaceae, Ophiocordycipitaceae, Tuberaceae, Morchellaceae, and Cordycipitaceae.

In embodiments, the filamentous fungus may be selected from the group consisting of strain MK7 (ATCC Accession Deposit No. PTA-10698), *Fusarium venenatum*, *Rhizopus oligosporus*, *Ustilago esculenta*, *Hericulum erinaceus*, *Polyporous squamosus*, *Grifola fondrosa*, *Hypsizygus marmoreus*, *Calocybe gambosa*, *Pholiota nameko*, *Calvatia gigantea*, *Agaricus bisporus*, *Stropharia rugosoannulata*, *Hypholoma lateritium*, *Pluerotus eryngii*, *Tuber borchii*, *Moschella esculenta*, *Moschella conica*, *Disciotis venosa*, *Ophiocordyceps sinensis* and *Cordyceps militaris*, *Trametes versicolor*, *Ganoderma lucidum*, *Flammulina velutipes*, *Lentinula edodes*, *Pleurotus djamor*, *Pleurotus ostreatus*, *Leucoagaricus holosericeus*, *Calvatia fragilis*, *Handkea utriformis*, and *Pholiota adiposa*.

In embodiments, the feedstock may comprise at least one of feces of an animal and urine of an animal. The animal may, but need not, be a human.

In embodiments, the at least one membrane may be a single composite membrane, wherein the first surface comprises a first material and the second surface comprises a second material.

In embodiments, the at least one membrane may comprise at least a first membrane and a second membrane, wherein the first surface is a surface of the first membrane and the second surface is a surface of the second membrane. The first and second membranes may, but need not, be in physical contact with each other.

In embodiments, the bioreactor may further comprise a selective gas-permeable membrane, wherein a first gas produced during growth of the biomat is selectively separated into a gas headspace on a first side of the selective gas-permeable membrane. A second gas produced during growth of the biomat may, but need not, be selectively separated into a gas headspace on a second side of the membrane. In some embodiments, a gas dissolved or dispersed in a liquid feedstock, or otherwise disposed on a feedstock side of the membrane, may be selectively separated from the feedstock and passed to an opposing side of a membrane.

It is another aspect of the present invention to provide a method for producing a biomat of a filamentous fungus, comprising inoculating a filamentous fungus in a bioreactor, wherein the bioreactor comprises a container; at least one membrane disposed within or on a surface of the container, the at least one membrane comprising a first surface and a second surface, wherein either or both of the first and second surfaces are adapted to receive thereon the inoculum of the filamentous fungus; and a feedstock for the growth of a filamentous fungus, contacting the first surface of the at least one membrane.

In embodiments, the container may be a bag, wherein the first and second surfaces of the at least one membrane are first and second surfaces of at least a portion of the bag.

In embodiments, the feedstock may be subjected to a positive or negative pressure imparted on a side of the feedstock opposite the first surface of the at least one membrane. The positive or negative pressure may, but need not, facilitate the inoculating step.

In embodiments, the method may further comprise providing cyanobacteria in the bioreactor, wherein the cyanobacteria provide at least one of oxygen gas and carbon to promote the growth of the biomat.

In embodiments, at least one of the following may be true: i) a density of the biomat after harvesting is at least about 0.6 grams per cubic centimeter; and ii) a density of the biomat after harvesting and drying is at least about 0.1 grams per cubic centimeter.

In embodiments, the biomat may comprise at least one layer.

In embodiments, during or after the harvesting step, the biomat may have a tensile strength of at least about 3 kilopascals or at least about 30 grams-force per square centimeter. During or after the harvesting step, the biomat may, but need not, have a tensile strength of at least about 100 kilopascals or at least about 1,020 grams-force per square centimeter.

In embodiments, the at least one membrane may comprise at least one polymer selected from the group consisting of polypropylenes, polytetrafluoroethylenes, polycarbonates, polyamides, cellulose acetate, polyvinylidene fluorides, mixed cellulose esters, polyethersulfones, polyethylenes, and polypyrroles.

In embodiments, the at least one membrane may comprise at least one material selected from the group consisting of polypropylene fabrics, polytetrafluoroethylene fabrics, and a nylon net filter.

In embodiments, the membrane may comprise at least one of a glass fiber material and a porous ceramic material.

In embodiments, an average pore size of the at least one membrane may be between about 0.2 µm and about 25 µm. An average pore size of the at least one membrane may, but need not, be between about 5 µm and about 11 µm.

In embodiments, the container may be enclosed and substantially airtight, wherein the container encloses a gas headspace into which the biomat grows.

In embodiments, the biomat may separate from the at least one membrane spontaneously.

In embodiments, the method may further comprise harvesting the biomat, wherein, when the biomat is removed from the at least one membrane, a new inoculum of filamentous fungi remains on the at least one membrane.

In embodiments, the filamentous fungus may belong to an order selected from the group consisting of Mucorales, Ustilaginales, Russulales, Polyporales, Agaricales, Pezizales, and Hypocreales.

In embodiments, the filamentous fungus may belong to a family selected from the group consisting of Mucoraceae, Ustilaginaceae, Hericiaceae, Polyporaceae, Grifolaceae, Lyophyllaceae, Strophariaceae, Lycoperdaceae, Agaricaceae, Pleurotaceae, Physalacriaceae, Omphalotaceae, Tuberaceae, Morchellaceae, and Cordycipitaceae.

In embodiments, the filamentous fungus may be selected from the group consisting of strain MK7 (ATCC Accession Deposit No. PTA-10698), *Fusarium venenatum*, *Rhizopus oligosporus*, *Ustilago esculenta*, *Hericulum erinaceus*, *Polyporous squamosus*, *Grifola fondrosa*, *Hypsizygus marmoreus*, *Calocybe gambosa*, *Pholiota nameko*, *Calvatia gigantea*, *Agaricus bisporus*, *Stropharia rugosoannulata*, *Hypholoma lateritium*, *Pluerotus eryngii*, *Tuber borchii*, *Morchella esculenta*, *Morchella conica*, *Disciotis venosa*, *Ophiocordyceps sinensis* and *Cordyceps militaris*.

In embodiments, the feedstock may comprise at least one of feces of an animal and urine of an animal. The animal may, but need not, be a human.

In embodiments, the at least one membrane may be a single composite membrane, wherein the first surface comprises a first material and the second surface comprises a second material.

In embodiments, the at least one membrane may comprise at least a first membrane and a second membrane, wherein the first surface is a surface of the first membrane and the second surface is a surface of the second membrane. The first and second membranes may, but need not, be in physical contact with each other.

In embodiments, the bioreactor may further comprise a selective gas-permeable membrane, wherein a first gas produced during growth of the biomat is selectively separated into a gas headspace on a first side of the selective gas-permeable membrane. A second gas produced during growth of the biomat may, but need not, be selectively separated into a gas headspace on a second side of the membrane.

It is another aspect of the present invention to provide a method for producing fresh water, comprising inoculating a filamentous fungus in a bioreactor, wherein the bioreactor comprises a container; and a feedstock for the growth of a filamentous fungus; culturing the filamentous fungus to form a biomat on at least one of a surface of the feedstock and a surface of a membrane of the bioreactor, wherein the filamentous fungus produces water as a byproduct during formation or growth of the biomat; and collecting water produced by the formation or growth of the biomat.

In embodiments, the feedstock may comprise at least one of the feces of an animal and the urine of an animal. The animal may, but need not, be a human.

In embodiments, the method may further comprise recycling the collected water to the bioreactor.

In embodiments, the method may further comprise preparing a feedstock comprising the collected water. The method may, but need not, further comprise recycling the prepared feedstock comprising the collected water to the bioreactor.

It is another aspect of the present invention to provide a method for producing a gas, comprising inoculating a filamentous fungus in a bioreactor, wherein the bioreactor comprises a container; and a feedstock for the growth of a filamentous fungus; culturing the filamentous fungus to form a biomat on at least one of a surface of the feedstock and a surface of a membrane of the bioreactor, wherein the filamentous fungus produces the gas as a metabolic byproduct during growth of the biomat; and collecting the gas produced by the growth of the biomat.

In embodiments, the gas may be selected from the group consisting of ammonia, an ammonium species, hydrogen gas, and a volatile ester.

It is one aspect of the present invention to provide a method for producing a biomat of a filamentous fungus, comprising (a) inoculating an effective amount of cells of at least one filamentous fungus to a first aliquot of growth medium to produce an inoculated growth medium; (b) incubating the inoculated growth medium for a first time to produce an initial biomat; (c) removing at least a portion of the first aliquot of growth medium and adding a second aliquot of growth medium to provide a refreshed growth medium; and (d) incubating the refreshed growth medium for a second time to produce a finished biomat.

In embodiments, the dry-mass density of the finished biomat may be at least about grams per liter.

In embodiments, the biomat may comprise greater than about 40 wt % protein and less than about 8 wt % RNA.

In embodiments, the at least one filamentous fungus may belong to an order selected from the group consisting of Ustilaginales, Russulales, Polyporales, Agaricales, Pezizales, and Hypocreales.

In embodiments, the at least one filamentous fungus may belong to a family selected from the group consisting of Ustilaginaceae, Hericiaceae, Polyporaceae, Grifolaceae, Lyophyllaceae, Strophariaceae, Lycoperdaceae, Agaricaceae, Pleurotaceae, Physalacriaceae, Omphalotaceae, Tuberaceae, Morchellaceae, and Cordycipitaceae.

In embodiments, the at least one filamentous fungus is selected from the group consisting of strain MK7 (ATCC Accession Deposit No. PTA-10698), *Fusarium venenatum*, *Ustilago esculenta*, *Hericulum erinaceus*, *Polyporous squamosus*, *Grifola fondrosa*, *Hypsizygus marmoreus*, *Calocybe gambosa*, *Pholiota nameko*, *Calvatia gigantea*, *Agaricus bisporus*, *Stropharia rugosoannulata*, *Hypholoma lateritium*, *Pluerotus eryngii*, *Tuber borchii*, *Moschella esculenta*, *Moschella conica*, *Disciotis venosa*, *Ophiocordyceps sinensis* and *Cordyceps militaris*.

In embodiments, the finished biomat may have a characteristic selected from the group consisting of (a) comprises greater than about 45 wt. % protein content; (b) comprises greater than about 50 wt. % protein content; (c) comprises greater than about 55 wt. % protein content; (d) comprises greater than about 60 wt. % protein content; (e) comprises less than about 5 wt. % RNA content; (f) comprises less than about 4 wt. % RNA content; (g) comprises less than about 3 wt. % RNA content; (h) comprises less than about 2 wt. % RNA content; and (i) combinations of one of a-d and one of e-h.

In embodiments, the finished biomat may comprise less than about 10 ppm of a mycotoxin selected from the group consisting of Alfatoxin B1, Alfatoxin B2, Alfatoxin G1, Alfatoxin G2, Fumonisin B1, Fumonisin B2, Fumonisin B3, Ochratoxin A, Nivalenol, Deoxynivalenol, Acetyl deoxynivalenol, Fusarenon X, T-2 Toxin, HT-2 Toxin, Neosolaniol, Diacetoxyscirpenol zearalenone, beauvericin, fusarin C, fusaric acid, and any combinations thereof.

In embodiments, the finished biomat may comprise less than about 10 ppm total mycotoxin content.

In embodiments, the finished biomat may comprise less than about 5 ppm total mycotoxin content.

In embodiments, the finished biomat may comprise greater than about 15 wt. % of branched chain amino acids.

It is another aspect of the present invention to provide a biomat of at least one filamentous fungus, having a dry-mass density of at least about 75 grams per liter.

In embodiments, the biomat may comprise greater than about 40 wt % protein and less than about 8 wt % RNA.

In embodiments, the at least one filamentous fungus may belong to an order selected from the group consisting of Mucorales, Ustilaginales, Russulales, Polyporales, Agaricales, Pezizales and Hypocreales.

In embodiments, the at least one filamentous fungus may belong to a family selected from the group consisting of Mucoraceae, Ustilaginaceae, Hericiaceae, Polyporaceae, Grifolaceae, Lyophyllaceae, Strophariaceae, Lycoperdaceae, Agaricaceae, Pleurotaceae, Physalacriaceae, Ophiocordycipitaceae, Tuberaceae, Morchellaceae, Sparassidaceae, Nectriaceae, Bionectriaceae, and Cordycipitaceae.

In embodiments, the at least one filamentous fungus is selected from the group consisting of *Rhizopus oligosporus, Ustilago esculenta, Hericululm erinaceus, Polyporous squamosus, Grifola frondosa, Hypsizygus marmoreus, Hypsizygus ulmarius* (elm oyster), *Calocybe gambosa, Pholiota nameko, Calvatia gigantea, Agaricus bisporus, Stropharia rugosoannulata, Hypholoma lateritium, Pleurotus eryngii, Pleurotus ostreatus* (pearl), *Pleurotus ostreatus* var. *columbines* (Blue oyster), *Tuber borchii, Morchella esculenta, Morchella conica, Morchella importuna, Sparassis crispa* (cauliflower), *Fusarium venenatum*, strain MK7 (ATCC Accession Deposit No. PTA-10698), *Disciotis venosa*, and *Cordyceps militaris. Trametes versicolor, Ganoderma lucidum, Flammulina velutipes, Lentinula edodes, Pleurotus djamor, Pleurotus ostreatus*, and *Leucoagaricus* spp.

In embodiments, the biomat may have a characteristic selected from the group consisting of (a) comprises greater than about 45 wt. % protein content; (b) comprises greater than about 50 wt. % protein content; (c) comprises greater than about 55 wt. % protein content; (d) comprises greater than about 60 wt. % protein content; (e) comprises less than about 5 wt. % RNA content; (f) comprises less than about 4 wt. % RNA content; (g) comprises less than about 3 wt. % RNA content; (h) comprises less than about 2 wt. % RNA content; and (i) combinations of one of a-d and one of e-h.

In embodiments, the biomat may comprise less than about 10 ppm of a mycotoxin selected from the group consisting of Alfatoxin B1, Alfatoxin B2, Alfatoxin G1, Alfatoxin G2, Fumonisin B1, Fumonisin B2, Fumonisin B3, Ochratoxin A, Nivalenol, Deoxynivalenol, Acetyl deoxynivalenol, Fusarenon X, T-2 Toxin, HT-2 Toxin, Neosolaniol, Diacetoxyscirpenol zearalenone, fusarin C, fusaric acid, and any combinations thereof.

In embodiments, the biomat may comprise less than about 10 ppm total mycotoxin content.

In embodiments, the biomat may comprise less than about 5 ppm total mycotoxin content.

In embodiments, the biomat may comprise greater than about 15 wt. % of branched chain amino acids.

In embodiments, the biomat may be produced by the methods described herein.

It is another aspect of the present invention to provide a method for producing a biomat of a filamentous fungus, comprising inoculating a filamentous fungus in a bioreactor, wherein the bioreactor comprises a container; at least one mesh scaffold disposed within or on a surface of the container, the at least one mesh scaffold comprising a first surface and a second surface, wherein either or both of the first and second surfaces are adapted to receive thereon the inoculum of the filamentous fungus; and a feedstock for the growth of a filamentous fungus, contacting the first surface of the mesh scaffold.

In embodiments, the mesh scaffold may comprise a nylon material.

It is another aspect of the present invention to provide a cultured food product, comprising particles of a filamentous fungus belonging to an order selected from the group consisting of Mucorales, Ustilaginales, Russulales, Polyporales, Agaricales, Pezizales, and Hypocreales, wherein the filamentous fungus comprises greater than about 40 wt. % protein content and less than about 8 wt. % RNA content; and a microbial food culture.

In embodiments, the microbial food culture may comprise lactic acid bacteria.

It is another aspect of the present invention to provide a method for making a cultured food product, comprising inoculating particles of a filamentous fungus with a microbial food culture, wherein the filamentous fungus belongs to an order selected from the group consisting of Mucorales, Ustilaginales, Russulales, Polyporales, Agaricales, Pezizales, and Hypocreales, wherein the filamentous fungus comprises greater than about wt. % protein content and less than about 8 wt. % RNA content.

In embodiments, the microbial food culture may comprise lactic acid bacteria.

In embodiments, cultured food products described herein may be made by methods of making cultured food products described herein.

BRIEF DESCRIPTION OF THE FIGURES

FIG. 20. Refractive index, density and particle size analysis in 10-1000× diluted samples of a vegan milk made with a filamentous fungus.

FIGS. 21A and 21B. Structure of vegan milk under optical microscope at 10× magnification and 100× magnification, respectively.

DETAILED DESCRIPTION

Figure 1:
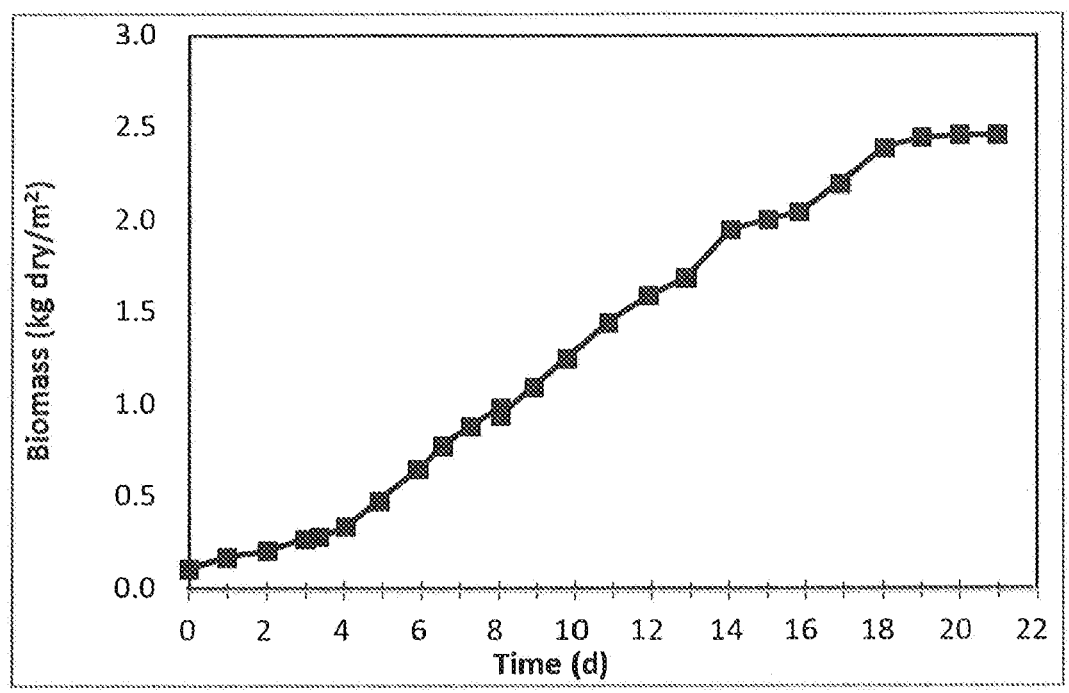
FIG. 1. Growth of *Fusarium* strain MK7 biomat in nutrient medium that was refreshed daily after the initial 4-day biomat growth stage.

As used herein, the term "biomat," unless otherwise specified, refers to cohesive mass of filamentous fungal tissue comprising a network of interwoven hyphae filaments. Biomats as that term is used herein may, but need not, be characterized by one or more of a density of between about 50 and about 200 grams per liter, a solids content of between about wt % and about 20 wt %, and sufficient tensile strength to be lifted substantially intact from the surface of a growth medium.

As used herein, the term "extracellular matrix," unless otherwise specified, refers to extracellular material that at least partially surrounds a filamentous fungal structure in a biomat and protects, supports, and/or isolates fungal mycelia of the biomat against a surrounding environment. Extracellular matrices as that term is used herein may generally include various macromolecules, including but not necessarily limited to proteoglycans (e.g. heparin sulfate, chondroitin sulfates, keratan sulfates), non-proteoglycan polysaccharides (e.g. hyaluronic acid), and proteins (e.g. collagen, elastin).

Edible filamentous fungi can be used as a nutrition source, such as for protein, either alone or incorporated into foodstuffs.

While the fruiting bodies of Basidiomycota and Ascomycota filamentous fungi, are used in foodstuffs, there are only a few products primarily comprising the vegetative mycelia of either the Basidiomycota or Ascomycota filamentous fungi. This is due, in part, to mycelia typically being either subterraneous or largely inseparable from the matter on which it grows.

Yet under particular conditions, filamentous fungi can form fungal biomats via surface fermentation under anaerobic, microaerobic, or aerobic conditions or a combination thereof. Here, the filamentous fungal biomats comprise the fungal species and/or strain and/or progeny thereof primarily in the form of mycelia, fragments of mycelia, hyphae, fragments of hyphae, and to a lesser extent contain conidia, microconidia, macroconidia, or any and all combinations thereof and in some cases can also contain pycnidia, chlamydospores, and portions of extracellular matrix.

Typically, the filamentous fungal biomats are primarily comprised of mycelia; that is, a complex network of interwoven vegetative hyphae filaments. The average length of non-broken filaments within the biomat is generally at least 0.1 mm, such as between 0.1 mm-100 cm, or any range defined by any two whole numbers between 1 mm and 100 cm. In some embodiments, the average length can be at least 0.1 mm, 0.25 mm, 0.5 mm, 1.0 mm, 1.4 mm 1.6 mm, 1.7 mm, 1.8 mm, 2 mm, 2.5 mm, 5 mm, 2 cm, 3 cm, 4 cm, 5 cm, 6 cm, 7 cm, 8 cm, 9 cm, 10 cm, 15 cm, 20 cm, 25 cm, 30 cm, 35 cm, 40 cm, 45 cm, 50 cm, cm, 60 cm, 65 cm, 70 cm, 75 cm, 80 cm, 85 cm, 90 cm, 85 cm, or 100 cm, or any number in between.

Described herein are food materials comprising particles of edible filamentous fungi and particularly ones that are grown as biomats before being processed into particles.

The filamentous fungi suitable for use in the invention (either as biomats or as particles in food materials) may be selected from the phyla or divisions zygomycota, glomermycota, chytridiomycota, basidiomycota or ascomycotal. The phylum (or division) basidiomycota comprises, inter alia, the orders Agaricales, Russulales, Polyporales and Ustilaginales; the phylum ascomycota comprises, inter alia, the orders Pezizales and Hypocreales; and the phylum zygomycota comprises, inter alia, the order Mucorales. The particles of edible filamentous fungi of the present invention belong to an order selected from Ustilaginales, Russulales, Polyporales, Agaricales, Pezizales, Hypocreales and Mucorales.

In some embodiments, the filamentous fungi of the order Ustilaginales are selected from the family Ustilaginaceae. In some embodiments, the filamentous fungi of the order Russulales are selected from the family Hericiaceae. In some embodiments, the filamentous fungi of the order Polyporales are selected from the families Polyporaceae or Grifolaceae. In some embodiments, the filamentous fungi of the order Agaricales are selected from the families Lyophyllaceae, Strophariaceae, Lycoperdaceae, Agaricaceae, Pleurotaceae, Physalacriaceae, or Omphalotaceae. In some embodiments, the filamentous fungi of the order Pezizales are selected from the families Tuberaceae or Morchellaceae. In some embodiments, the filamentous fungi of the order Mucorales are selected from the family Mucoraceae.

In some embodiments, the filamentous fungi may be selected from the genera *Fusarium*, *Aspergillus*, *Trichoderma*, and *Rhizopus*.

Examples of the species of filamentous fungi include, without limitation, *Ustilago esculenta*, *Hericululm erinaceus*, *Polyporous squamosus*, *Grifola fondrosa*, *Hypsizygus marmoreus*, *Hypsizygus ulmariuos* (elm oyster) *Calocybe gamboa*, *Pholiota nameko*, *Calvatia gigantea*, *Agaricus bisporus*, *Stropharia rugosoannulata*, *Hypholoma lateritium*, *Pleurotus eryngii*, *Pleurotus ostreatus* (pearl), *Pleurotus ostreatus* var. *columbinus* (Blue oyster), *Tuber borchii*, *Morchella esculenta*, *Morchella conica*, *Morchella importuna*, *Sparassis crispa* (cauliflower), *Fusarium venenatum*, strain MK7 (ATCC Accession Deposit No. PTA-10698), *Disciotis venosa*, *Cordyceps militaris*, *Ganoderma lucidum* (reishi), *Flammulina velutipes*, *Lentinula edodes*, *Ophiocordyceps sinensis*. Additional examples include, without limitation, *Trametes versicolor*, *Ceriporia lacerate*, *Pholiota gigantea*, *Leucoagaricus holosericeus*, *Pleurotus djamor*, *Calvatia fragilis*, *Handkea utriformis*, and *Rhizopus oligosporus*.

In some embodiments, the filamentous fungus is a *Fusarium* species. In some embodiments, the filamentous fungus is the *Fusarium* strain MK7 (ATCC PTA-10698 deposited with the American Type Culture Collection, 1081 University Boulevard, Manassas, Virginia, USA). Strain MK7 was previously reported to be a *Fusarium oxysporum* strain. However, it has subsequently been identified as not being a *oxysporum* strain. In some embodiments, the filamentous fungus is the *Fusarium* strain *Fusarium venenatum*.

As described in detail herein, the filamentous fungi of the present invention have a surprisingly high protein content. It is noted that the filamentous fungi that grow naturally or in the wild or by prior art methods do not possess such high protein contents, whereas filamentous fungi grown or cultured as disclosed herein have a high protein content, and in particular higher protein content than is achieved in nature or, for some fungi by prior fermentation methods. For example, protein contents of filamentous fungi described herein refer to the protein contents of the filamentous fungi as grown in a biomat according to the present disclosure. Consequently, food materials of the invention have high protein contents based on the filamentous fungi components of the materials without the need for and/or in the absence of protein content from a non-filamentous fungal source. Thus, in various embodiments, food materials of the invention do not contain or have an absence of protein content from a non-filamentous fungal source.

In some embodiments, the filamentous fungi comprise at least about 30 wt. % protein content. Unless specified otherwise herein, percentages of components, such as proteins, RNA or lipids, of biomats or filamentous fungi particles, are given as a dry weight percent basis. For example, biomats can be dried for 2 days at 99° C. and further air dried for a few days, at the end of which the biomats are expected to contain about 5 wt. % or less moisture, such as less than 4 wt. %, less than 3 wt. %, less than 2 wt. %, less than 1 wt. %, less than 0.5 wt. %, less than 0.1 wt. % moisture. The total protein content in dried biomat samples can be measured using total nitrogen analysis method for estimating proteins.

In some embodiments, the filamentous fungi comprise at least about 30%, at least about 31 wt. %, at least about 32 wt. %, at least about 33 wt. %, at least about 34 wt. %, at least about 35 wt. %, at least about 36 wt. %, at least about 37 wt. %, at least about 38 wt. %, at least about 39 wt. %, at least about 40 wt. %, at least about 41 wt. %, at least about 42 wt. %, at least about 43 wt. %, at least about 44 wt. %, at least about 45 wt. %, at least about 46 wt. %, at least about 47 wt. %, at least about 48 wt. %, at least about 49 wt. %, at least about 50 wt. %, at least about 51 wt. %, at least about 52 wt. %, at least about 53 wt. %, at least about 54 wt. %, at least about 55 wt. %, at least about 56 wt. %, at least about 57 wt. %, at least about 58 wt. %, at least about 59 wt. %, at least about 60 wt. % protein content, at least about 61 wt. %, at least about 62 wt. %, at least about 63 wt. %, at least about 64 wt. %, at least about 65 wt. %, at least about 66 wt. %, at least about 67 wt. %, at least about 68 wt. %, at least about 69 wt. %, at least about 70 wt. % protein content, at least about 71 wt. %, at least about 72 wt. %, at least about 73 wt. %, at least about 74 wt. %, at least about 77 wt. %, at least about 76 wt. %, at least about 77 wt. %, at least about 78 wt. %, at least about 79 wt. %, or at least about 80 wt. % protein content. Alternatively, in embodiments of the invention, filamentous fungi can comprise protein in a range between 30 wt. % and 80 wt. % or in any whole number percentage range between 30 wt. % and 80 wt. %. See Examples 21-23.

The filamentous fungi of the present invention also have surprisingly low RNA content. High amounts of RNA in food have been shown to have adverse health or physiological effects. For example, diets that are high in purines (present in RNA) are associated with incidence of gout. Filamentous fungi as grown or cultured as disclosed herein have intrinsically low RNA content and do not require additional or supplemental treatment to modify or lower the RNA content. Thus, in various embodiments, food materials of the invention do not contain filamentous fungal components that have significant levels of RNA and/or that have been treated for the purpose of modifying or lowering the RNA content of the components or food materials. In other embodiments, it will be recognized that food materials of the invention having filamentous fungal components with naturally low amounts of RNA may be treated, for example by heating or steaming to inactive the fungus, or by other treatments that would also reduce or degrade RNA, if it were present. Such materials can be characterized as having filamentous fungal components that have a low RNA content as described herein prior to or without any such reduction or degradation of RNA.

In some embodiments, the filamentous fungi comprise less than about 8 wt. % RNA content. The wt. % RNA content is given on a dry weight basis. For example, the total RNA content in dried biomat samples can be measured using the purine analysis method. See Example 24.

In some embodiments, the RNA content in the filamentous fungi is less than about 8.0 wt. % RNA content, less than about 7 wt. % RNA content, less than about 6 wt. % RNA content, less than about 5.0 wt. % RNA content, less than about 4 wt. % RNA content, less than about 3 wt. % RNA content, less than about 2 wt. % RNA content, or less than about 1 wt. % RNA content, or alternatively less than any increment 0.1-wt % increment less than about 8.0 wt %.

Alternatively, in embodiments of the invention, filamentous fungi can comprise RNA in a range between 0.5 wt. % and 8 wt. % or any sub-range thereof.

In some embodiments, the filamentous fungus comprises a high protein content combined with a low RNA content as described above. For example, in some embodiments the filamentous fungus may comprise greater than 45 wt. % protein, greater than 50 wt. % protein, greater than 55 wt. % protein, or greater than 60 wt. % protein and less than about 8 wt. % RNA content, less than about 5 wt. % RNA content, less than about 4 wt. % RNA content, less than about 3 wt. % RNA content, or less than about 2 wt. % RNA content. In other embodiments, the filamentous fungus can have any protein content described above in combination with any RNA content described above.

The filamentous fungi of the present invention and related food materials can also be characterized as having surprisingly low mycotoxin content. Known mycotoxins include Alfatoxin B1, Alfatoxin B2, Alfatoxin G1, Alfatoxin G2, Fumonisin B1, Fumonisin B2, Fumonisin B3, Ochratoxin A, Nivalenol, Deoxynivalenol, Acetyl deoxynivalenol, Fusarenon X, T-2 Toxin, HT-2 Toxin, Neosolaniol, Diacetoxyscirpenol, beauvericin, fusarin C, fusaric acid, and zearalenone. In some embodiments, the total amount of mycotoxins and/or the total amount of any one of or subset of the above-listed mycotoxins in a filamentous fungi, biomat or food material of the invention is less than about 10 ppm. In other embodiments, the total amount of mycotoxins and/or the total amount of any one of or subset of the above-listed mycotoxins is less than about 9 ppm, less than about 8 ppm, less than about 7 ppm, less than about 6 ppm, less than about 5 ppm, less than about 4 ppm, less than about 3 ppm, less than about 2 ppm, less than about 1 ppm, less than about 0.9 ppm, less than about 0.8 ppm, less than about 0.7 ppm, or less than about 0.6 ppm. See Example 25.

The filamentous fungi of the present invention also have a surprisingly high branched amino acid content. Branched amino acids refer to leucine, isoleucine and valine. In some embodiments, the total amount of branched amino acids is greater than about 10 wt. %, greater than about 11 wt. %, greater than about 12 wt. %, greater than about 13 wt. %, greater than about 14 wt. %, greater than about 15 wt. %, greater than about 16 wt. %, greater than about 17 wt. %, greater than about 18 wt. %, greater than about 19 wt. %, greater than about 20 wt. %, greater than about 21 wt. %, greater than about 22 wt. %, greater than about 23 wt. %, greater than about 24 wt. %, greater than about 25 wt. %, greater than about 26 wt. %, greater than about 27 wt. %, greater than about 28 wt. %, greater than about 29 wt. %, greater than about 30 wt. %. See Example 23 for the content of branched amino acids in exemplary strain MK7 and *Fusarium venenatum* biomats. Example 23 also shows the fatty acid profile of the two fungi.

Growing and Harvesting Filamentous Fungal Biomats

The growth of filamentous fungal biomats can be accomplished via surface fermentation. This involves inoculating a liquid medium containing a carbon source and a nitrogen source with filamentous fungal cells. Suitable carbon sources are sugars (e.g. sucrose, maltose, glucose, fructose, Japan rare sugars, etc.), sugar alcohols (e.g. glycerol, polyol, etc.), starch (e.g. corn starch, etc.), starch derivative (e.g. maltodextrin, cyclodextrin, glucose syrup, hydrolysates and modified starch), starch hydrolysates, hydrogenated starch hydrolysates (HSH; e.g. hydrogenated glucose syrups, maltitol syrups, sorbitol syrups, etc.), lignocellulosic pulp or feedstock (e.g. sugar beet pulp, agricultural pulp, lumber pulp, distiller dry grains, brewery waste, etc.), corn steep liquors, acid whey, sweet whey, milk serum, wheat steep liquors, carbohydrates, food waste, olive oil processing waste, hydrolysate from lignocellulosic materials, and/or combinations thereof. The filamentous fungi generate biomats which are located on the surface of the growth media.

Liquid growth media according to the present invention may be characterized by a desired or preselected mass ratio of carbon to nitrogen ("C:N ratio"). Typically, the C:N ratio of liquid growth media according to the present invention may have a C:N ratio of between about 1:1 and about 50:1, or between about 2.5:1 and about 30:1, or between about and about 10:1, or between about any ratio between 1:1 and 50:1 and about any other ratio between 1:1 and 50:1. By way of non-limiting example, growth media according to the present invention may have a C:N ratio of about 2.5:1, about 5:1, about 7.5:1, about 10:1, about 12.5:1, about 15:1, about 17.5:1, about 20:1, about 22.5:1, about 25:1, about 27.5:1, about 30:1, about 32.5:1, about 35:1, about 37.5:1, about 40:1, about 42.5:1, about 45:1, about 47.5:1, or about 50:1, or alternatively about any ratio of the form X:2 where X is an integer between about 2 and about 100.

Inoculation may be done with an inoculum comprising planktonic filamentous fungal cells, conidia, microconidia or macroconidia or spores, or fruiting bodies. In many cases, especially for Ascomycota fungi, growth media may be inoculated with an inoculum comprising planktonic filamentous fungal cells, conidia, microconidia or macroconidia. Ideally, the cells of the inoculum float on the surface of the growth media, such as those cells having a high lipid content, and result in increased growth rate. Cells or clumps of cells that are submersed within the growth media can negatively affect the cells floating on the surface and the biomats they form. Specifically, the biomats resulting from growth media containing a significant number of clumped submerged cells are typically discolored and tend to not grow homogeneously dense mats.

In some embodiments, the inoculum may comprise spores. For example, in one embodiment, approximately 2 cc of sterile Basidiomycota spores suspended in deionized water from a spore syringe (e.g. MycoDirect, Huntley, IL) were used to inoculate approximately 75 mL of growth media in small Pyrex trays. Alternatively, 1 cc of spores suspended in deionized water from a spore syringe was plated on a container having malt extract agar media+CF (30 g dry malt extract, 20 g agar, 1000 mL water+0.01% chloramphenicol) using standard sterile conditions. Containers were sealed with parafilm and incubated at room temperature until mycelium completely covered the surface of the agar. A segment of mycelium from the agar preparation approximately 2 cm in width cut into a wedge was then diced into the smallest size possible before transferring to a tube with growth media. Liquid culture tubes were sealed, incubated at room temperature, and shaken by hand or shaken by mechanical means (i.e. continuous shaking or a continuous stirred tank reactor) for about 1 minute at least five (5) times per day to break up mycelium as much as possible. Liquid cultures were incubated until visually turbid, typically three or more days. The liquid cultures were then used to inoculate growth medium in trays at a 10% or 15% of total growth medium volume.

In some embodiments, the inoculum may comprise fruiting bodies. For example, in some embodiments, Basidiomycota fruiting bodies were used to generate inoculum for initiating filamentous biomats. In some instances, inoculum was prepared by (a) surface sterilizing fruiting bodies, for example in a 5% bleach solution, (b) rinsing with sterile media, (c) grinding under sterile conditions to either less than 5 mm long aggregates or greater than 5 mm aggregates, depending on the final use, (d) surface sterilizing the ground mushroom biomass for example in a 5% bleach solution, and again rinsing with sterile media. 5 grams of the ground surface-sterilized fruiting body biomass was used directly as inoculum. In other instances, a pure culture derived from a fruiting body was used. In this instance, ~3 mm 3 portions of fruiting body was placed on agar media containing 0.01% chloramphenicol and incubated at room temperature. After 2-5 days of growth, hyphae were transferred onto fresh agar+chloramphenicol media and grown for another 3-7 days. Culture purity was confirmed by extracting and purifying DNA (FastDNA Spin Kit, MP Biomedicals), sequencing the 18S rRNA sequence and/or ITS region, and performing phylogenetic classification of the sequences using Blast (NCBI database). Upon confirmation, hyphae were used to inoculate 50 mL of sterile liquid media and agitated/rotated at 185 rpm for approximately 5 days before using as inoculum at a ratio of about 7.5% inoculum to 92.5% liquid media.

While a number of different media can be used, certain media perform better than others for growth of filamentous fungal biomats; by way of non-limiting example, Hansen's media (per liter=1.0 g peptone, 0.3 g $KH_2PO_4 \cdot 7H_2O$, 2.0 g $MgSO_4 \cdot 7H_2O$ 5.0 g glucose with a C:N ratio of 26.9) did not yield full, cohesive biomats, while those media which work exceptionally well include MK7A, MK7-1, MK7-3 (all described in WO 2017/151684), as well as the media presented below. These are also described in Example 12.

Malt Medium 001 (C:N Ratio of 19.1)

| Ingredient | Amount | Grade |
| --- | --- | --- |
| Light Pilsner Malt | 40.0 g | Food |
| Peptone | 4.0 g | Research |
| Yeast Extract Powder | 1.2 g | Research |
| Canola Oil | 1.0 mL | Food |
| Ground Oats | 4.0 g | Food |
| Tap $H_2O$ | 1000 mL | N/A |

MK-7 SF Medium (C:N Ratio of 7.5)

| Ingredient | Amount | Grade |
| --- | --- | --- |
| $NH_4NO_3$ | 7.553 g | ACS |
| Urea | 2.548 g | USP |
| $CaCl_2$ | 2.000 g | Reagent |
| $MgSO_4 * 7H_2O$ | 2.000 g | USP |
| $KH_2PO_4$ | 7.500 g | Reagent |
| Trace * | 2.000 mL | * |
| Glycerol | 0.075 Kg | Food/USP |
| Yeast Extract | 1.750 g | Research |
| $FeCL_2 * 4H_2O$ | 0.020 g | Reagent |
| DI $H_2O$ | 0.940 L | N/A |

| Trace Components * | | |
| --- | --- | --- |
| Micronutrients* | mg/L | Grade |
| $FeSO_4 \cdot 7 H2O$ | 9.98 | ACS |
| $ZnSO_4 \cdot 7 H2O$ | 4.4 | USP/FCC |
| $MnCl_2 \cdot 4 H2O$ | 1.01 | Reagent |
| $CoCl_2 \cdot 6 H2O$ | 0.32 | Reagent |
| $CuSO_4 \cdot 5 H2O$ | 0.31 | Technical |
| $(NH_4)_6Mo_7O_{24} \cdot 4 H2O$ | 0.22 | ACS |
| $H_3BO_3$ | 0.23 | ACS |
| EDTA, free acid | 78.52 | Electrophoresis |

Malt Media 001 Supplemented with NH$_4$NO$_3$(C:N Ratio of 7.5)

| Ingredient | Amount | Grade |
|---|---|---|
| NH$_4$NO$_3$ | 5.0 g | ACS |
| Light Pilsner Malt | 40.0 g | Food |
| Peptone | 4.0 g | Research |
| Yeast Extract Powder | 1.2 g | Research |
| Canola Oil | 1.0 mL | Food |
| Ground Oats | 4.0 g | Food |
| Tap H$_2$O | 1000 mL | N/A |

Osmotic concentrations as osmolality can be determined by measurement of media with an Osmometer (e.g., Model 3250 SN: 17060594) capable of measuring up to 5000 mOsm/kg. Three readings were taken for several media and provided the following results: Hansen's=39, 39, 38; Malt 001=169, 168, 169; MK-7 SF=1389, 1386, 1387; Malt 001+NH$_4$NO$_3$=288, 287, 286.

As noted before, methods of the invention can result in increasing the protein content, amino acid profile (e.g. content of branched-chain amino acids), and/or nutritional content of the filamentous fungus. Without being bound by theory, this result is believed to be due in part to the media used to grow the fungus.

For example, while the natural protein content of the fruiting body of Blue Oyster mushrooms (*Pleurotus ostreatus* var. *Columbinus*) is reported to be about 16.32% (Ulziijargal and Mau (2011) Int J Medicinal Mushrooms, 13(4): 343-49) or 24.65% (Stamets (2005) Int J Medicinal Mushrooms 7:103-110), as shown in Example 12, Blue Oyster biomats grown according to the present invention on Malt 001 media have a higher moisture corrected protein content of 29.82%, an increase in protein content of 13.6% or 5.71%.

The protein content of the fruiting body of Pearl Oyster mushrooms (*Pleurotus ostreatus*) is reported to be about 23.85% (Ulziijargal and Mau (2011) Int J Medicinal Mushrooms, 13(4):343-49) or 27.25% (Stamets (2005) Int J Medicinal Mushrooms 7:103-110); Pearl Oyster biomats grown according to the present invention have a higher moisture corrected protein content of 39.77%, an increase in protein content of at least 46% to a maximum of 67%.

The protein content of the fruiting body of Cauliflower mushrooms (*Sparassis crispa*) is reported to be about 13.4% (Kimura (2013) BioMed Research International); Cauliflower biomats grown according to the present invention have a higher moisture corrected protein content of 32.21%-46.24%, an increase in protein content of least 140% to a maximum of 245%.

Other characteristics of the media that are believed to be important for the growth of biomats on the surface of a fermentation media are the osmotic pressure and the ionic strength of the media. In some embodiments, the osmotic pressure of the media for growth of biomats can be greater than about 3 atm, greater than about 10 atm, greater than about 20 atm, greater than about 30 atm, greater than about 40 atm, greater than about 50 atm, greater than about 60 atm, greater than about 70 atm, greater than about 80 atm, greater than about atm, greater than about 100 atm, greater than about 110 atm, greater than about 120 atm, greater than about 125 atm, or greater than any whole-number atmosphere value greater than 3 atmospheres through greater than 125 atmospheres. In alternative embodiments, the osmotic pressure may range between about 3 atm to about 125 atm, between about 20 atm and about 100 atm or between any two whole number atm values between 3 and 125.

In some embodiments, the ionic strength of the media that can be used to grow biomats can be greater than about 0.02 M, greater than about 0.05 M, greater than about M, greater than about 0.20 M, greater than about 0.30 M, greater than about 0.40 M, greater than about 0.50 M, greater than about 0.60 M, greater than about 0.70 M, greater than about 0.80 M, greater than about 0.90 M, greater than about 1.0 M, or greater than any one-hundredth M value greater than 0.02 M through greater than 1.00 M. In alternative embodiments, the ionic strength may range between about 0.02 M to about 1.0 M, between about 0.10 M and about 0.50 M or between any two number molar concentration values between 0.01 and 1.0.

Harvesting of biomats can occur at any time a sufficiently thick biomat has formed. Harvesting typically occurs after 2-3 days of growth, although in some instances longer growth periods are desirable, such as when thicker or denser biomats are desired/required. For example, harvesting can occur after growth of between 2 days and 60 days or any range of days or partial days (e.g., hours) between 2 days and 60 days. For example, such growth periods can be 3.5-4 days, 3-5 days, 4-6 days, 5-7 days, 6-9 days, 7-10 days, or 19-21 days, or alternatively about any whole number of days up to and including about 21 days. As used herein, the term "harvesting," refers to any process or step that stops growth of a biomat (e.g., separation from a nutrient source or change in temperature conditions) and/or that modifies a physical characteristic of a biomat (e.g., converting a biomat into particles or strips).

Due to the cohesive structure of the filamentous biomats grown under surface fermentation conditions described in PCT/US2017/020050 and herein, the filamentous biomats have enough tensile strength to be lifted essentially intact from the surface of the media at the end of the growth period. In various embodiments, biomats of the invention can have a tensile strength of at least about 30 g/cm$^2$, at least about 40 g/cm$^2$, at least about g/cm$^2$, at least about 60 g/cm$^2$, at least about 70 g/cm$^2$, at least about 80 g/cm$^2$, at least about 90 g/cm$^2$, at least about 100 g/cm$^2$, at least about 150 g/cm$^2$, at least about 200 g/cm$^2$, at least about 250 g/cm$^2$, at least about 300 g/cm$^2$, at least about 350 g/cm$^2$, at least about 400 g/cm$^2$, at least about 450 g/cm$^2$, at least about 500 g/cm$^2$, at least about 550 g/cm$^2$, or at least about 600 g/cm$^2$, or at least about 650 g/cm$^2$, or at least about 700 g/cm$^2$, or at least about 750 g/cm$^2$, or at least about 800 g/cm$^2$, or at least about 850 g/cm$^2$, or at least about 900 g/cm$^2$, or at least about 950 g/cm$^2$, or at least about 1000 g/cm$^2$, or at least about 1500 g/cm$^2$, or at least about 2000 g/cm$^2$, or at least about 2500 g/cm$^2$, or at least about 3000 g/cm$^2$, or at least about 3500 g/cm$^2$, or at least about 4000 g/cm$^2$. In other embodiments, biomats of the invention can have a tensile strength of greater than any whole number greater than 30 g/cm$^2$. Alternatively, the tensile strength of biomats of the invention can be in a range of between about 30 g/cm$^2$ and about 4000 g/cm$^2$ or any whole number range between about 30 g/cm$^2$ and about 4000 g/cm$^2$. A suitable method for measuring tensile strength is explained in Example 41.

Table 1A presents some examples of tensile strength and other physical characteristics measured for various filamentous fungi.

TABLE 1A

Average Tensile Strength for some filamentous fungal biomats

| Organism | Carbon source | Thickness (cm) | Width (cm) | Avg. Break wt (g) | Avg. Tensile Strength (g/cm$^2$) |
|---|---|---|---|---|---|
| Giant Puffball | Malt | 0.13 | 1.2 | 47.12 | 314.13 |
| | Glycerol | 0.10-1.3 | 1.2 | 29.05 | 214.85 |
| | MK7-1SF | 0.25-0.35 | 0.65-0.8 | 30.67 | 263.98 |
| | Malt + NH$_4$NO$_3$ | 0.09-0.10 | 0.9-1.1 | 27 | 281.15 |
| Cauliflower | Malt | 0.15-2.0 | 1.0-1.2 | 101.05 | 507.38 |
| | Glycerol | 0.09-0.20 | 1.2 | 202.17 | 242.91 |
| Reishi | Malt | 0.5 | 1.0-1.2 | 101.05 | 1854.54 |
| Blue Oyster | Malt | 0.5 | 1.2 | 43.40 | 72.74 |
| | Glycerol | 0.4 | 1.3 | 19.04 | 37.27 |
| Pearl Oyster | Malt | 0.5 | 1.0-1.2 | 56.7 | 98.96 |
| Elm Oyster | Malt | 0.35 | 1.2 | 50.28 | 143.67 |
| F. strain MK7 | Glycerol | 0.5-0.8 | 1.0 | >742 | >570 |

Table 1B shows additional examples of tensile strength and other physical characteristics measured for various filamentous fungi obtained using other media.

| | initial pH | Final pH | Wet Weight g | Dry Weight g | Density g/cm$^3$ | Yield g/m$^2$ | Tensile Strength g/cm$^2$ |
|---|---|---|---|---|---|---|---|
| C:N 5 | | | | | | | |
| MK-7 | 3.3 | 6.2 | 0.4888 | 0.2953 | 0.48 | 483.33 | 333.33 |
| F. Venenatum | 4.5 | 6.15 | 0.3379 | 0.275 | 0.14 | 71.43 | 186.67 |
| GPB | 6 | 6.25 | 0.527 | 0.2708 | 0.21 | 144.76 | 562.96 |
| C:N 7.5 | | | | | | | |
| MK-7 | 3.3 | 7.2 | 0.827 | 0.4416 | 0.31 | 314.62 | 1454.55 |
| F. Venenatum | 4.5 | 4.81 | 0.57 | 0.3245 | 0.09 | 89.06 | 166.67 |
| GPB | 6 | 5.45 | 0.348 | 0.2851 | 0.08 | 38.41 | 1259.26 |
| C:N 15 | | | | | | | |
| MK-7 | 3.3 | 4.91 | 0.4833 | 0.257 | 0.07 | 92.31 | 191.11 |
| F. Venenatum | 4.5 | 3.49 | 0.3458 | 0.2734 | 0.16 | 63.81 | 800.00 |
| GPB | 6 | 2.74 | 0.3245 | 0.322 | 0.20 | 197.12 | 1559.23 |
| C:N 30 | | | | | | | |
| MK-7 | 3.3 | 2.36 | 0.2832 | 0.2774 | 0.10 | 103.64 | 426.67 |
| F. Venenatum | 4.5 | 3.29 | 0.323 | 0.3142 | 0.06 | 76.03 | 370.37 |
| GPB | 6 | 2.87 | 0.271 | 0.2688 | 0.17 | 134.91 | 833.33 |
| C:N 40 | | | | | | | |
| MK-7 | 3.3 | 2.81 | 1.3952 | 0.3638 | 0.05 | 156.09 | 312.12 |
| F. Venenatum | 4.5 | 2.97 | 0.5097 | 0.3637 | 0.43 | 215.95 | 3151.52 |
| GPB | 6 | 3.1 | 0.7196 | 0.3487 | 0.36 | 179.66 | 1040.00 |

In various embodiments, biomats of the invention can have a thickness ranging from about 0.05 cm to at least about 2 cm.

In various embodiments, biomats of the invention can have a width ranging from about 0.6 cm to about 3 meters. Generally, biomats produced according to the present invention may have a width approximately equal to a width of the vessel in which the biomat is grown.

Surface fermentation can be carried out under various conditions, including static media conditions (as described in PCT Publication WO 2017/151684, which is incorporated herein by reference in its entirety), semi-static media conditions, and continuous media flow conditions. Some embodiments are described in Examples 1-4.

Growth under semi-static media conditions means that at least a portion of the medium is replaced before the filamentous fungal biomat is harvested. These conditions allow linear dry biomass production over an extended period of time demonstrating the suitability of this system to operate as a continuous production system. For example, in one experiment, linear dry biomass production was achieved from day 4 through day 18 ($r^2$=0.995), after which biomass weight stabilized at about 2.5 Kg dry/m$^2$.

Biomats can also be produced under continuous media flow conditions where biomat growth is confined to the surface of the growth media where the medium underneath the mat is continuously refreshed or semi-continuously refreshed.

In some instances, however, it is desirable to harvest the growing biomat on a semi-continuous basis. Here, removal of some portion of the biomat occurs and the remaining portion is then physically moved to the open area of medium that was created by removal of the portion of biomat. This can be accomplished by physically grasping the biomat and pulling it until it touches the end of the surface fermentation container or by other mechanical means. The resulting open area is then available for new biomat growth without a separate or additional inoculation step since the medium already contains viable fungal cells. This process can be repeated periodically, which can be particularly useful when the medium is refreshed or nutrients that have become limited are reintroduced.

Biomat harvesting can also be done on a continuous basis. Continuous removal can be facilitated by a number of mechanisms. One such example is a roller wheel that is attached to the mature end of the biomat (see FIG. 7). The roller wheel slowly turns and harvests the mature biomat and at the same time creates open medium for growth of new biomat at the other end of the surface fermentation container. In various embodiments, harvesting can be conducted at a rate of at least about 0.1 cm/day, 0.2 cm/day, 0.3 cm/day, cm/day, 0.5 cm/day, 0.6 cm/day, 0.7 cm/day, 0.8 cm/day, 0.9 cm/day, 1.0 cm/day, 1.1 cm/day, 1.2 cm/day, 1.3 cm/day, 1.4 cm/day, 1.5 cm/day, 1.6 cm/day, 1.7 cm/day, 1.8 cm/day, 1.9 cm/day, 2.0 cm/day, 2.1 cm/day, 2.2 cm/day, 2.3 cm/day, 2.4 cm/day or 2.5 cm/day. A typical rate of harvesting is 1.56 cm/day, although this can be altered for particular needs or as desired by a user.

In some cases, UVB light (290-320 nm) can trigger pigment production by filamentous fungi, such as for *Fusarium* strain MK7 (ATCC Accession Deposit No. PTA-10698), producing a pigmented biomat. In addition to a color change, which can be useful for creating various food effects, treatment with UVB converts ergosterol present in the fungal cell membranes into vitamin D2 and increases production of carotenoids, such as beta carotene and astaxanthin. Consequently, irradiating filamentous fungi, such as *Fusarium* strain MK7, with UVB can be used to increase vitamin D2 and carotenoids in the resulting biomats.

In some cases, the filamentous fungal biomats formed are composed of layers which are uniform in appearance, one surface of the filamentous biomat in contact with the air and one surface in contact with the synthetic media. In other cases, at least two distinct layers are present: an aerial hyphae layer at the top surface and a dense multicellular bottom layer in contact with the synthetic media. Oftentimes three distinct layers are present: (a) an aerial hyphae layer at the top surface, (b) a dense bottom layer and (c) a transitional layer between the top and bottom layers. The transitional layer may be only loosely attached to the dense bottom layer, in those cases enabling easy separation of the bottom layer from the rest of the biomat. Filament densities of the transitional layer range from slightly less dense than the bottom layer in the zone where the two layers meet, to a density that is comparable to the aerial hyphae near the top of the biomat.

In some embodiments, biomats may comprise strain MK7 (ATCC Accession Deposit No. PTA-10698), *Fusarium venenatum, Rhizopus oligosporus, Morchella esculenta* (Morel), *Morchella conica* (Morel), *Morchella importuna* (Morel), *Calvatia gigantea* (giant puffball), *Pleurotus ostreatus* (pearl oyster), *Pleurotus ostreatus* var. *columbinus* (blue oyster), *Sparassis crispa* (cauliflower), *Ganoderma lucidum* (Reishi), *Hypsizygus ulmarius* (elm oyster).

Inactivation of Filamentous Fungal Biomats

While biomats can be rinsed to remove excess growth media, biomat rinsing is not required, although in some cases the removal of growth media or excess growth media is preferable. Similarly, biomats can be squeezed to remove excess growth media, again not required, but which may be preferable for some applications.

Elimination of cell viability and the potential of further biomat growth is desired in some instances, such as for use of the biomat as a stand-alone protein source or a protein ingredient in foodstuffs. This can be accomplished by heating, irradiation, ethanol and/or steaming.

For the heating process, filamentous fungal biomats can be treated according to WO or British Patent No 1,440,642, for example, or incubated at temperatures that destroy the vast majority of the organism's RNA without adversely affecting the organism's protein composition.

In irradiation, filamentous fungal biomats are exposed to ionizing energy, such as that produced by $^{60}Co$ (or infrequently by $^{137}Cs$) radioisotopes, X-rays generated by machines operated below a nominal energy of 5 MeV, and accelerated electrons generated by machines operated below a nominal energy of 10 MeV.

Steaming can also be used for inactivating some filamentous fungal biomats, such as those produced by *Fusarium* strain MK7 (ATCC Accession Deposit No. PTA-10698) and *F. venenatum*, as steaming can also remove some specific metabolites from the biomat construct if those metabolites are produced. Here, biomats are placed such that biomat excreted liquids and condensed steam can easily drip away from the biomats. Suitable biomat holding systems include porous plastic mesh and porous trays. Other biomat holding systems include, but are not limited to, systems that secure the biomat in a vertical position, such as systems with a clamping mechanism that clamps at least one end of a biomat while the remaining end(s) of the biomat hang from said clamp and mesh systems which clamp at least two sides of the biomat, to name but a few.

Biomats are positioned within a steamer such that heated steam, such as steam of a temperature greater than 85° C. or 95° C., comes into contact with the biomats. In those cases where multiple trays are placed in a single steamer, for example one tray above the other, it is preferred to protect a lower positioned biomat from the drippings of a higher positioned biomat. Protection should be of a form which allows steam to contact biomats, thereby de-activating biomat viability, and to also deflect biomat excreted liquids and condensed steam produced at a higher level in the steamer from contacting biomats positioned at a lower level in the steamer. In one embodiment, a cone is positioned between an upper tray and a lower tray to accomplish this result. In other embodiments, separation between upper and lower trays also include at least one other geometric shape such as a cylinder, a cube and/or cuboid, a pyramid, a sphere, a tori, and/or other platonic solids. In yet another embodiment, trays are separated using at least one cylinder, cube and/or cuboid, pyramid, sphere, tori, other platonic solid, mesh, porous belt, or combinations thereof.

Biomats are steamed at least to the point where biomat viability is reduced such that further biomat growth and/or cellular reproduction within a biomat is negligible. Biomat viability is a function of the original substrate, biomat development, steam/heat transfer characteristics, biomat position in a steamer and biomat orientation relative to evolved steam. As an example, *Fusarium* strain MK7 biomats grown on a glycerol or acid whey substrate are non-viable after 5 minutes, and in some cases less than 5 minutes, of steaming. Steamed mats can be rinsed and/or squeezed to remove mat excretions and condensed steam.

The inactivated edible filamentous fungal biomats can be used directly as a protein source, for example in preparing foodstuffs largely comparable to tofu, bacon, and jerky, to name but a few.

Particles of Filamentous Fungal Biomats

The inactivated edible filamentous fungal biomats can also be size reduced for use as a protein source in foodstuffs. The size reduction can occur by mechanical means such as cutting, chopping, dicing, mincing, grinding, blending, etc. or via sonication and is conducted prior to mixing with other ingredients or liquids. Size reduced particles can be uniform in size or variable.

Typically, the length of the sized reduced particles is between 0.05-500 mm, the width is between 0.03-7 mm, and height is between 0.03-1.0 mm. For example, flour-type particles typically range between 0.03 mm and 0.4 mm, jerky-type particles range between 100 mm and 500, etc. Larger size particles can be produced. For example, biomats have been grown in inflatable pools (66" in diameter) producing a single biomat 66" in diameter and completely round. Larger vessels can be used to grow even larger mats.

The number of size reduced particles produced per biomat is dependent on the initial biomat size and the purpose for which the biomat size reduced particles will be used.

Large Particles

In some embodiments, the inactivated edible filamentous fungal biomats are reduced to particles, wherein at least 50%, or at least 60%, or at least 70%, or at least 80%, or at least 90% of the particles have a particle length of about 0.05 mm to about 500 mm, a particle width of about 0.03 mm to about 7 mm, and a particle height of about 0.03 mm to about 1.0 mm, or alternatively in any subranges within these ranges. For example, at least 50%, or at least 60%, or at least 70%, or at least 80%, or at least 90% of the particles may have a particle length of about 0.08 mm to about 100 mm, or 10 mm to about 70 mm, or 130 mm to about 200 mm; a particle width of about 0.05 mm to about 2 mm, or about 1 mm to about 3 mm, or about 4 mm to about 6 mm; and a particle height of about 0.03 mm to about 0.06 mm, or about 0.04 mm to about 0.07 mm, or about 0.08 mm to about 1.0 mm.

In some embodiments, the inactivated edible filamentous fungal biomats are reduced to particles, wherein at least 50%, or at least 60%, or at least 70%, or at least 80%, or at least 90% of the mass of the particles have a particle length of about 0.05 mm to about 500 mm, a particle width of about 0.03 mm to about 7 mm, and a particle height of about mm to about 1.0 mm, or alternatively in any subranges within these ranges. For example, at least 50%, or at least 60%, or at least 70%, or at least 80%, or at least 90% of the mass of the particles may have a particle length of about 0.08 mm to about 100 mm, or mm to about 70 mm, or 130 mm to about 200 mm; a particle width of about 0.05 mm to about 2 mm, or about 1 mm to about 3 mm, or about 4 mm to about 6 mm; and a particle height of about 0.03 mm to about 0.06 mm, or about 0.04 mm to about 0.07 mm, or about mm to about 1.0 mm.

For example, at least 50%, or at least 60%, or at least 70%, or at least 80%, or at least 90% of the particles may have a particle length of about 0.08 mm to about 100 mm, or mm to about 70 mm, or 130 mm to about 200 mm; a particle width of about 0.05 mm to about 2 mm, or about 1 mm to about 3 mm, or about 4 mm to about 6 mm; and a particle height of about 0.03 mm to about 0.06 mm, or about 0.04 mm to about 0.07 mm, or about mm to about 1.0 mm.

Such particles mimic the texture and chewiness of meat products such as chicken nuggets or hamburgers, and are useful in the preparation of such products, such as a filler or extender of meat products, or their vegetarian versions. In the case of use of particles of the invention as a filler or extender of meat product, the ratio of filamentous fungal particles to meat can range from 10:90 to 90:10 or any ratio in between.

For example, in some embodiments, the filamentous fungal particles comprise particles having at least 90% of the particles with lengths less than about 1.5 mm and the majority of lengths being 1 mm or less, widths of less than about 1 mm, and heights of less than about 0.75 mm. Food materials comprising such particles is characterized as having a higher perceived density in the mouth, is easier to chew, offers a creamy mouth feel and a more refined food experience, and such particles may be used to prepare a food material that resembles a hamburger found in fine dining establishments.

In some embodiments, the filamentous fungal particles comprise particles having at least about 90% of the particles with lengths between about 4 mm and about 10 mm, widths of about 1.0 mm to about 3 mm, and heights of less than 0.75 mm. Food materials comprising such particles is found to lead a more heartier food experience similar to the type of burger prepared commonly found in burger restaurants or BBQ's.

Fine Particles (Flour)

In some embodiments, the inactivated edible filamentous fungal biomats are reduced to fine particles. In some embodiments, the particles of filamentous fungus are in the form of a flour. In such embodiments, the particle size and particle size distributions may be the same or similar to those conventional for flour-like materials, such as wheat or other flours. In some embodiments, at least 50%, or at least 60%, or at least 70%, or at least 80%, or at least 90% of the particles fall within the range of 0.03 mm to about 0.4 mm, or alternatively in any subrange within this range, such as about 0.03 mm to 0.07 mm, about 0.07 mm to about 0.12 mm, about 0.12 mm to about 0.15 mm, about 0.15 mm to about 2.0, about 0.04 mm to about 0.2 mm, or 0.06 mm to about 0.120 mm or 0.2 mm to about 0.4 mm. In some embodiments, at least 50%, or at least 60%, or at least 70%, or at least 80%, or at least 90% of the particles fall within the range of 0.075 mm to about 0.12 mm.

In some embodiments, at least 50%, or at least 60%, or at least 70%, or at least 80%, or at least 90% of the mass of the particles fall within the range of 0.03 mm to about 0.4 mm, or alternatively in any subrange within this range, such as about 0.03 mm to 0.07 mm, about 0.07 mm to about 0.12 mm, about 0.12 mm to about 0.15 mm, about 0.15 mm to about 2.0, about 0.04 mm to about 0.2 mm, or 0.06 mm to about 0.120 mm or 0.2 mm to about 0.4 mm. In some embodiments, at least 50%, or at least 60%, or at least 70%, or at least 80%, or at least 90% of the mass of the particles fall within the range of 0.075 mm to about 0.12 mm.

The size reduction may be done using a flour mill, grinder or other conventional equipment for size reduction.

In some embodiments, the moisture content of fine particulate material of the invention is less than about 15%, about 14%, about 13%, about 12%, about 11%, about 10%, about 9%, about 8%, about 7%, about 6%, about 5%, about 4%, about 3%, about 2% or about 1%. The low moisture levels aid to prevent clumping of the particles.

Such particles are useful in the preparation of food materials such as baked goods, including but not limited to bread, rolls, muffins, cakes, cookies, pies, etc. or can be sprinkled on other food products.

Liquid Dispersion (Milk)

One aspect of introducing protein into a foodstuff is to use a liquid dispersion made from the filamentous fungal biomat as a replacement ingredient for milk or a milk analog. The liquid dispersion (also referred herein as "milk") comprises particles of filamentous fungal biomats dispersed in an aqueous medium.

The size of the filamentous fungal biomat particles suitable for use in liquid dispersions is typically smaller than about 10 microns. In some embodiments, at least 50%, or at least 60%, or at least 70%, or at least 80%, or at least 90% of the particles in a liquid dispersion fall within the range of about 1 microns to about 10 microns, or alternatively in any subrange within this range. In some embodiments, at least 50%, or at least 60%, or at least 70%, or at least 80%, or at least 90% of the particles are less than 10 microns, less than 9 microns, less than 8 microns, less than 7 microns, less than 6 microns, less than 5 microns, less than 4 microns, less than 3 microns, less than 2 microns, or less than 1 micron. In some embodiments, at least about 50%, or at least about 60%, or at least about 70%, or at least about 80%, or at least about 90% of the particles may have a particle size of less than about 1 micron.

The liquid dispersion or milk can be prepared by combining and blending a filamentous fungal biomat with an aqueous phase, such as water. The blended mixture can be heated gradually, such as to a boiling temperature. The heated mixture is then allowed to cool. In some embodiments, a liquid dispersion can be produced under nitrogen. This process results in a creamier consistency of liquid dispersion with less fungal scent. Production under nitrogen can be accomplished by bubbling with nitrogen in a closed vessel such that nitrogen replaces most all of the available oxygen, either during blending, such as with a Vitamix or in a high-energy size reduction or milling process, or in the heat cycle. An exemplary method is described in Example 27.

The filamentous fungal biomat to water ratio can be adjusted to produce a liquid dispersion of the appropriate consistency and density. The ratio of the biomat to water can range from about 1:10 to about 10:1 or any range of ratios in between. In some embodiments, the ratio of the biomat to water can be about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1.

In various embodiments, a liquid dispersion of the invention is stable such that the particulates of filamentous fungus do not readily separate from the liquid medium in which they are dispersed. For example, upon forming the dispersion, the formed liquid appears to be homogeneous in appearance and does not visibly separate into distinct phases. For example, no visibly discernable or significant sediment forms on the bottom of the container holding the dispersion. In some embodiments, the liquid dispersion remains stable for at least about 1, 2, 3, 4, 5, 6, 9, 12, 15, 18, 21, or 24 hours or alternatively, it can remain stable for at least about 1, 2, 3, 4, 5, 6, or 7 days, or 1, 2, 3, or 4 weeks, or 1, 2, 3, 4, 5, or 6 months. In these embodiments, the dispersion can either be at room temperature or at refrigerated temperatures, such as at about 35° F. (1.6° C.).

Example 26 illustrates the stability of a liquid dispersion, i.e., a milk, of the invention. A milk that sat undisturbed in a refrigerator for 15 days and 30 days, and no visible separation was observed in either sample. The milk also did not exhibit degradation of flavor or smell.

In some embodiments, the dispersion comprises at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20% solids. In other embodiments, a liquid dispersion of the invention will have a solids content of between about 4% and about 30% or any sub-range between 4% and 30%.

The liquid dispersion can be used as a drink or beverage, including as a substitute for any milk product such as dairy milk, almond milk, rice milk, soy milk etc. It can be used in a number of recipes including soups, ice cream, yogurt, smoothies, fudge, and candies such as caramel and truffles. In some cases, the filamentous fungal biomats produced from different feedstocks/carbon sources result in liquid dispersions having different flavors. For example, when the feedstock/carbon source is glycerol, the resulting liquid dispersion produced from *Fusarium* strain MK7 is sweeter while a liquid dispersion resulting from *Fusarium* strain MK7 grown on an acid whey feedstock/carbon source tends to be sourer. The native sweetness or sourness of the filamentous fungus, e.g. *Fusarium* strain MK7, transfers to the ultimate food product. For instance, acid whey liquid dispersions lends itself to yogurt, while glycerol liquid dispersions tends to lend itself to mouse, caramel or fudge.

In some embodiments, the liquid dispersion can be used to form a stable foam, in that it forms a foam that does not collapse spontaneously immediately upon cessation of the foaming process. The foaming process can include whipping with a whipping appliance, incorporation of compressed gases or other conventional foaming processes. The foam is smooth and creamy in appearance and shows the presence of bubbles in a distribution of sizes. The larger bubbles tend to pop after sitting or being poured, but the smaller bubbles stay in suspension for a long time to form a stable foam product. A foam product of the invention has the compositional characteristics of a liquid dispersion and additionally has air or other gas incorporated into the foam in a stable manner. For example, a foamed material of the invention can have an increased volume (i.e., overrun) by incorporation of air of at least about 10%, at least about 20%, at least about 30%, at least about 40%, at least about 50%, at least about 75%, at least about 100%, at least about 200%, at least about 300%, at least about 400%, or at least about 500%, as compared to the starting volume of the liquid dispersion prior to foaming. In various embodiments, a foamed material is stable for at least about 1 day, at least about 2 days, at least about 3 days, at least about 4 days, or at least about 5 days, at least about 6 days, at least about 7 days, at least about 8 days, at least about 9 days, at least about 10 days, at least about 11 days, at least about 12 days, at least about 13 days, at least about 14 days, or at least about 15 days, at least about 16 days, at least about 17 days, at least about 18 days, at least about 19 days, at least about 20 days, at least about 21 days, at least about 22 days, at least about 23 days, at least about 24 days, or at least about 25 days, at least about 26 days, at least about 27 days, at least about 28 days, at least about 29 days, at least about 30 days. In some embodiments, the liquid dispersion remains stable for at least about one month, at least about two months, or at least about three months. As used in reference to a foam, stability refers to retaining at least about 50%, at least about 60%, at least about 70%, at least about 80%, at least about 90%, at least about 95% of its initial foamed volume.

An average overrun of about 12% is suitable for preparing ice cream (with more fat and emulsifiers), frozen yogurt, cheesecake batters, whipped toppings etc. In some embodiments, the foam may incorporate nitrogen to provide different overrun characteristics.

In some embodiments, the food material is a cultured food product. As used herein, unless otherwise specified, the term "cultured food product" refers to a food product in which a microbial food culture, i.e. live bacteria, yeasts, or molds, is introduced to a filamentous fungus. By way of non-limiting example, fungal food materials according to the present invention may be cultured with *Lactobacillus* spp. or other lactic acid bacteria (to make, e.g., a yogurt analog food product or other dairy analog food product), *Saccharomyces cerevisiae* or other yeasts used in brewing or baking (to make, e.g., a baked good analog food product or an alcoholic beverage analog food product), molds traditionally used to make sausages (e.g. *Penicillium chyrsogenum* or *Penicillium nalgiovense*, to make a sausage analog food product) or soy sauces (such as *Aspergillus oryzae* or *Aspergillus sojae*, to make a soy sauce analog food product), and so on. In some embodiments, cultured food products according to the present invention may be cultured with two or more microbial food cultures, either simultaneously or sequentially, to produce an analog of a food product that is made by fermentation of two or more microbial cultures; by way of non-limiting example, cultured food products according to the present invention may include semi-soft ripened cheese analog food products (made by subjecting a fungal material to a first culture by *Lactobacillus* spp. or other lactic acid bacteria and a second culture by a cheese ripening yeast), blue cheese analog food products (made by subjecting a fungal material to a first culture by *Lactobacillus* spp. or other lactic acid bacteria and a second culture by a mold such as *Penicillium* roqueforti), soft ripened cheese (e.g. Brie or Camembert) analog food products (made by subjecting a fungal material to a first culture by *Lactobacillus* spp. or other lactic acid bacteria and a second culture by *Penicillium* camemberti), etc.

In some embodiments, the food material comprises a yogurt analog food product comprising the particles of the filamentous fungal biomats of the present invention dispersed in an aqueous medium. In some embodiments of the yogurt analog, the ratio of filamentous fungal particles to water may range from about 1:10 to about 10:1. A higher ratio of ratio of filamentous fungal particles to water is expected to increase the texture and reduce runniness of the yogurt analog food product. In some embodiments, the ratio of filamentous fungal particles to water may be about 1:3, 1:2, 1:1 or 2:1.

In some embodiments, the yogurt analog food product comprises an invert sugar or inverted sugar. Invert sugar is resistant to crystallization and promotes retention of moisture. and is used commercially in various foods such as baked goods, confections, or fruit preserves and beverages to enhance flavor and texture and prolong shelf life. Examples include honey or a mixture of glucose and fructose that is obtained by hydrolysis of sucrose and is sweeter than sucrose.

In some embodiments, the yogurt analog food product comprises a thickening or gelling agent. Such agents are known in the art and include but are not limited to: agar, gelatin, starches (i.e. arrowroot, tapioca, corn, potato), higher fat liquids (coconut milk), fat (i.e. coconut flakes, deodorized or otherwise), chickpea water, flax seeds, xanthan gum, guar gum, psyllium husk, ground chia seed, nut/seed butters, pumpkin puree, cooked mashed yams/ sweet potato, applesauce, mashed overripe bananas or plantains, pureed dates or prunes, soaked and simmered figs, shredded fruit/vegetables, shredded coconut, gluten free flours (e.g. teff flour, buckwheat flour, amaranth flour, chickpea flour, sorghum flour, almond flour), cooked pureed beans, cocoa Powder, vegetable gums, polysaccharides, vegetable mucilage, seaweed derivatives, pectin, gluten, soy and egg analogs. A thickening agent may be a fat, which may be a liquid such as coconut milk, or a solid such as deodorized coconut flakes.

In some embodiments, the cells of the filamentous fungi are lysed, which releases more protein and leads to increased thickening and potentially greater bioavailability of the nutrients. The lysis may be effected by any methods known in the art such as sonication.

In some embodiments, the yogurt analog food product comprises lactic acid bacteria (LAB). These bacteria produce lactic acid as the major metabolic end product of carbohydrate fermentation. Examples of LAB include the genera *Lactobacillus, Leuconostoc, Pediococcus, Lactococcus*, and *Streptococcus*. In some embodiments, it comprises the bacteria *Lactobacillus bulgaricus* and/or *Streptococcus thermophilus*.

In some embodiments, the yogurt analog food product further comprises a rennet. The rennet may be derived from an animal source, a vegetarian source or a microbial source. In vegetarian or vegan food products, the rennet is derived from a vegetarian source and/or a microbial source.

In some embodiments, the yogurt analog food product further comprises an enzymatic water. For example, an enzymatic water can be produced as follows. 100 gm of whole rye or durum wheat seeds (or other suitable whole cereal seeds) may be combined with 1 liter of water, and germinated for 2-4 hours. When seeds start to sprout and the first roots appear, the seeds may be placed into a clean jar with 1 liter of water. The jar may be covered with a permeable cloth (linen or cotton), and incubated at room temp for 24 hours, at the end of which the water in the jar changes color and odor. This water is referred to as enzymatic water and can be used in the production of yogurt and cheese.

In some embodiments, the yogurt analog food product further comprises a probiotic. Probiotics are mixtures of live micro-organisms such as bacteria and yeast that provide health benefits including improved digestion.

In some embodiments, the yogurt analog food product comprises milk solids derived from animal milk. In some embodiments, the yogurt analog food product is free of milk solids derived from animal milk, i.e. it does not contain any milk solids.

It is to be expressly understood that in addition to yogurt analog food products, food materials of the present invention may comprise any one or more other dairy analog food products. By way of first non-limiting example, food materials of the present invention may comprise a cheese analog food product, such as a hard cheese (e.g. Parmesan) analog food product, a semi-hard cheese (e.g. Gouda) analog food product, a semi-soft cheese (e.g. Havarti) analog food product, a soft or soft ripened cheese (e.g. Brie) analog food product, a cream cheese analog food product, a sour milk cheese analog food product, a blue cheese analog food product, a mascarpone cheese analog food product, a pasta filata (e.g. Mozzarella) cheese analog food product, a brined cheese (e.g. Feta) analog food product, a whey cheese (e.g. Ricotta or Brunost) analog food product, or a fresh cheese (e.g. cottage cheese) analog food product. By way of second non-limiting example, food materials of the present invention may comprise a butter analog food product, such as a raw cream butter analog food product, a butterfat analog food product, a clarified butter analog food product, a whey butter analog food product, a cultured butter analog food product, a mild cultured butter analog food product, a sweet cream butter analog food product, or a traditional buttermilk analog food product. By way of third non-limiting example, food materials of the present invention may comprise a whey analog food product, such as a sour whey analog food product or a sweet whey analog food product. By way of fourth non-limiting example, food materials of the present invention may comprise a cream analog food product, such as a crème fraîche analog food product, a smetana analog food product, a sour cream analog food product, a half-and-half analog food product, a table cream analog food product, a whipping cream analog food product, a double cream analog food product, a clotted cream analog food product, a soured cream analog food product, a pasteurized cream analog food product, or a condensed cream analog food product. By way of fifth non-limiting example, food materials of the present invention may comprise a sour milk analog food product, such as a quark analog food product, a cheese curd analog food product, a soured milk analog food product, a kefir analog food product, an organic yogurt or mild yogurt analog food product, a yogurt analog food product, a cream yogurt analog food product, or a cultured buttermilk analog food product. By way of sixth non-limiting example, food materials of the present invention may comprise a milk analog food product, such as a raw milk analog food product, a lowfat or skimmed raw milk analog food product, a pasteurized milk analog food product, a fresh whole milk analog food product, a lowfat milk analog food product, a skimmed milk analog food product, an extended shelf-life (ESL) milk analog food product, an ultra-high temperature processed (UHT) milk analog food product, a sterilized milk analog food product, a condensed or evaporated milk analog food product, a part-skim condensed milk analog food product, or a condensed skimmed milk analog food product. By way of seventh non-limiting example, food materials of the present invention may comprise a powdered dairy analog food product, such as a powdered whey analog food product, a powdered milk analog food product, or a powdered skimmed milk analog food product. Dairy analog food products according to the present invention may, in embodiments, be vegan food products, i.e. food products that contain no animal products, and thus allow observers of vegan diets to incorporate such dairy analogs into their diet.

tous fungal biomats, or the size-reduced particles of such biomats, the particles can be optimized for particular textures, mouthfeel, and chewiness. The ability to alter texture, mouth feel, and chewiness allow customization to accommodate individuals having particular dietary needs, such as those that have trouble chewing, or who require/desire softer foods while still providing the same nutritional and taste experience or those who desired food with more texture, more mouthfeel and more mastication. Because of the ability to easily control the particle size, foods augmented with filamentous fungal biomats or made solely from filamentous fungal biomats have textures very similar to the standard protein foods that they emulate, as can be seen in Table 2.

TABLE 2

Results from Stable Micro Systems TA XT plus texture analyzer

| Food | Avg. Max Hardness | Avg. Area (g/mm) | Avg. Mean (g) | Parameters |
|---|---|---|---|---|
| Fish Stick | | | | Pre-Test Speed: 2.00 mm/sec |
| Commercial fish stick | 3654 ± 1774 | 17868 ± 5674 | 894 ± 284 | Test Speed: 4.00 mm/sec Post-Test Speed: 10.00 mm/sec |
| MK7 fish stick | 1618 ± 180 | 19990 ± 610 | 1000 ± 100 | Target Mode: Distance Force: 100.0 g |
| Chicken Nugget | | | | |
| Commercial chicken nugget | 3838 ± 56.8 | 27329 ± 3663 | 1367 ± 183 | Distance: 20.000 mm Strain: 10.0% |
| Quorn chicken nugget | 4013 ± 1066.3 | 27751 ± 1346.4 | 1415 ± 111.4 | Trigger Type: Auto (Force) Tigger Force: 5.0 g |
| MK7 small particle | 3127 ± 19.7 | 33065 ± 3458 | 1654 ± 173 | Probe: HDP/WBV Warner Bratzler V Slot Blade |
| MK7 medium particle | 2514 ± 663 | 27217 ± 6437 | 1361 ± 322 | |
| MK7 large particle | 3461 ± 77.8 | 34591 ± 2971.2 | 1730 ± 14.6 | |
| Burger | | | | |
| 100% Beef burger | 4326 ± 714 | 12350 ± 46.1 | 1727 ± 14.1 | |
| 90% Beef, 10% MK7 | 5011 | 14048 | 1929 | |
| 80% Beef, 20% MK7 | 2615 ± 199 | 10641 ± 511 | 1456 ± 46 | |
| 70% Beef, 30% MK7 | 2240 ± 262 | 9859 ± 2947 | 1291 ± 300 | |
| 60% Beef, 40% MK7 | 2094 ± 156 | 8118 ± 1088 | 1155 ± 180 | |
| 100% MK7, chopped (highly processed) | 2228 ± 1988 | 5079 ± 964 | 1089 ± 70.6 | |

| Food | Firmness (g) | Parameters |
|---|---|---|
| Chocolate Mousse | | Pre-Test Speed: 1.00 mm/sec |
| Nestle chocolate mousse | 182.45 | Test Speed: 1.00 mm/sec Post-Test Speed: 10.00 mm/sec |
| MK7 chocolate mousse | 135.09 | Target Mode: Distance T.A. Variable No: 5: 0.0 g Distance: 10.000 mm Strain: 10.0% Trigger Type: Auto (Force) Tigger Force: 5.0 g Probe: P/25; 25 mm DIA Cylinder Aluminum |

Particles of the filamentous fungal biomat can be added as a protein or other nutritional source to augment the nutritional content of a foodstuff or can be, for example, the sole protein component. For foods composed entirely of filamentous fungal biomats can be used as sole protein components in a food material or can be used to augment protein content of other food materials. Examples of foods that can be produced using only the reduced particle size of the filamentous fungal biomat, with or without added flavorings, include without limitation meat-like vegetarian or vegan products (e.g., ground beef, ground chicken, ground turkey, chicken nuggets, fish sticks or patties, jerky), snacks (e.g. chips), soups, smoothies, beverages, milk analogs, breads, pastas, noodles, dumplings, pastries (e.g. Pate a Choux), cookies, cakes, pies, desserts, frozen desserts, ice cream analogues, yogurt, confections, and candy.

Foods augmented with the reduced particle size of the filamentous fungal biomat can significantly increase the protein content, which is particularly important for individuals following a vegan diet. For example, soups, drinks or smoothies can be augmented with strain MK7 liquid dispersion.

Whether biomat particles of reduced size are used to augment the protein content of food or is used as the sole protein component, in some instances binders are helpful in achieving the desired texture. Approved foodstuff binders are suitable, such as egg albumen, gluten, chickpea flour, vegetarian binders, arrowroot, gelatin, pectin, guar gum, carrageenan, xanthan gum, whey, chick pea water, ground flax seeds, egg replacer, flour, agar-agar, Chia seeds, psyllium, etc. which can be used singularly or in combination. In addition to foodstuff binders, the reduced particle size of the filamentous fungal biomat can also be mixed with approved flavors, spices, flavor enhancers, fats, fat replacers, preservatives, sweeteners, color additives, nutrients, emulsifiers, stabilizers, thickeners, pH control agents, acidulants, leavening agents, anti-caking agents, humectants, yeast nutrients, dough strengtheners, dough conditioners, firming agents, enzyme preparations, gasses, and combinations thereof. Typically, binders, flavors, spices, etc. are selected to meet the demands of a particular population. For example, milk and/or milk solids are not used to accommodate individuals with dairy allergies/sensitivities, wheat flour may not be used to accommodate those with gluten allergies/sensitivities, etc.

In some applications, a substantially unimodal particle size distribution, i.e. in which all particles are approximately the same size, may be used, while in other applications a broad or multimodal distribution or combination of distributions of particle size may be used. Similarly, size-reduced particles can be derived from a single source of filamentous fungal biomat or from a combination of different sources of filamentous fungal biomats; e.g. strain MK7 alone or strain MK7 and *Fusarium venenatum*, or strain MK7 and *Fusarium venenatum* and Giant Puffball biomats, etc.

The use of filamentous fungi for commercial production in the past has generally required significant infrastructure and/or equipment, energy requirements, expensive reagents, and/or significant human resources. Filamentous fungi are well known for having the greatest metabolic diversity of all microorganisms on Earth, including the ability to produce a wide spectrum of organic acids, antibiotics, enzymes, hormones, lipids, mycotoxins, vitamins, organic acids, pigments, and recombinant heterologous proteins (Wiebi (2002) Myco-protein from *Fusarium venenatum*: a well-established product for human consumption. Appl Microbiol Biotechnol 58, 421-427; El-Enshasy (2007) Chapter 9—Filamentous Fungal Cultures—Process Characteristics, Products, and Applications. In. Bioprocessing for Value-Added Products from Renewable Resources. Editor: Shang-Tian Yang. Elsevier; Gibbs et al (2000) Growth of filamentous fungi in submerged culture: problems and possible solutions. Crit. Rev. Biotechnol. 20, 17-48), as well as the ability to degrade many types of recalcitrant materials such as lignocellulose and humic substances in soils.

While widely used, significant challenges to production by submerged fermentation still exist and include important factors such as growth limitation due to the restricted oxygen availability and excessive shear forces generated by agitation (Gibbs et al (2000) Growth of filamentous fungi in submerged culture: problems and possible solutions. Crit. Rev. Biotechnol. 20, 17-48). Since oxygen solubility in water under Earth surface conditions is about 8 mg/L, it is readily depleted during rapid growth in submerged cultures. Thus, continuous aeration using complex, expensive and energy intensive aeration and agitation systems is required to maintain high growth rates. The cultivation of filamentous fungi is even more challenging since the filamentous morphology imparts non-Newtonian rheological behavior that further inhibits oxygen transfer to solution (Nørregaard et al. (2014) Filamentous Fungi Fermentation. In Industrial Scale Suspension Culture of Living Cells, H.-P. Meyer, and D. R. Schmidhalter, eds. (Wiley-VCH Verlag GmbH & Co. kGaA), pp. 130-162). As culture densities increase, the amount of energy required to aerate and mix the cultures increases nonlinearly as well as the energy requirements to aerate dense cultures are very high. For many filamentous species, vigorous agitation and aeration of the cultures becomes detrimental to hyphal growth and as a result dramatically decreases growth rate. These and other challenges to submerged fermentation of filamentous microorganisms require innovative solutions to effectively harness these organisms with the limited resources available in spacecraft and at extraterrestrial stations.

The disclosed reactor system (1) addresses these problems and has the following advantages:
  Active aeration or agitation of the liquid culture is not necessary;
  In-situ aggregation of biomass into a single coherent mat with significant tensile strength (>0.1 kg/cm of biomat width) which allows easy harvesting;
  Textured biomats can be used for a wide variety of mission critical products (i.e. food, bioplastics, biofuels, nutritional supplements, and as an expression platform for a variety of pharmaceuticals;
  Minimal water use as well as minimal and/or no residual waste water or nutrients from the process while maintaining high biomass production (80-120 $g/m^2/d$ or g/L/h)
  Growth rates can translate to the production of fully formed biomats in as little as 2 days or can be further expanded for more than 10 days, in some embodiments up to at least about 21 days;
  High biomass density (biomats are typically 0.684 g/cm 3 wet weight or 0.123 $g/cm^3$ dry weight);
  High yield (6.9 kg/m 2 wet weight or 1.23 $Kg/m^2$ dry weight total, and in some embodiments up to at least about 206 $g/m^2$ dry weight per day);
  A variety of filamentous fungi (including extremophiles, as well as known edible and commercially relevant mushrooms) with specific advantages for different processes can be grown;
  Scale-up or down is relatively straightforward and does not result in decreased productivity up to a growth area of at least about 150 $cm^2$;
  Process can use a very wide variety of C and N-rich waste substrates that arise from natural disasters and/or space missions.

The disclosed reactor system provides a self-contained biomat reactor comprising a container and placed within the container a feedstock, a fungal inoculum, an at least semi-permeable membrane (e.g. gas-permeable, liquid-permeable, gas-semi-permeable, and/or liquid-semi-permeable), and optionally a liquid nutrient medium. Depending upon the circumstances, the reactor can be a one-time use reactor or a reusable reactor.

Typically, the container is capable of being sealed and may include a container cover in addition to a seal. Some container examples are a covered tray, a covered petrie dish, another type of covered container, or a bag. For some uses or in some environments the container has a plurality of growth chambers, for example following a manifold design and/or a baffling system.

The feedstock is inoculated with a filamentous fungal strain as described above. Examples of Ascomycetes strains are strain MK7 (ATCC PTA-10698 deposited with the American Type Culture Collection, 1081 University Boulevard, Manassas, Virginia, USA), *Fusarium venenatum*, *Fusarium avenaceum*, and/or combinations thereof. Inoculation of the feedstock can occur at the time the feedstock is placed within the container or can occur sometime after the feedstock has been placed. That is, the reactor (1) can be primed with freeze-dried filamentous fungal inoculum that is revived upon contact with the feedstock or the feedstock can be directly inoculated after placement in the reactor channel(s) (4) or the feedstock can be inoculated and then placed in the reactor channel(s).

With respect to the feedstock used in the reactor, the feedstock can be as described above. For example, it can be a waste product, such as naturally occurring urine and/or feces, food waste, plant material, industrial waste such as glycerol, and waste by-products, starch and/or by products of starch hydrolysis, acid whey, sugar alcohol, and/or combinations thereof. Synthesized or manufactured waste surrogates, such as surrogate human urine can also be used. Plant material feedstocks are typically lignocellulosic. Some examples of lignocellulosic feedstock are agricultural crop residues (e.g. wheat straw, barley straw, rice straw, small grain straw, corn stover, corn fibers (e.g. corn fiber gum (CFG), distillers dried grains (DDG), corn gluten mean (CGM), switch grass, sugar beet pulp, waste streams from palm oil production, hay-alfalfa, sugarcane bagasse, non-agricultural biomass (e.g. algal biomass, cyanobacterial biomass, urban tree residue), forest products and industry residues (e.g., softwood first/secondary mill residue, hard softwood first/secondary mill residue, recycled paper pulp sludge), lignocellulosic containing waste (e.g. newsprint, waste paper, brewing grains, used rubber tire (URT), municipal organic waste and by-products, yard waste and by-products, clinical organic waste and by-products, and waste and by-products generated during the production of biofuels (e.g. processed algal biomass, glycerol), and combinations thereof.

In embodiments, the permeable membrane may comprise a polymeric material, such as, by way of non-limiting example, a polypropylene, a polyethylene, a polytetrafluoroethylene, a polycarbonate, a polyamide (e.g. nylon), a polypyrrolone, a poly(amidoamine) dendrimer composite, a polyvinylidene fluoride, a polyethersulfone, cellulose acetate, a mix of cellulose esters, and/or butadiene-acrylonitrile. The permeable membrane may comprise, additionally and/or alternatively, a glass fiber material, a porous ceramic material, and/or a fabric, such as, by way of non-limiting example, a polypropylene fabric, a polytetrafluoroethylene fabric, and/or a nylon net filter. While the pore size of the permeable membrane (2) typically may be any 0.01 µm increment value or range of values between about 0.2 µm and about 25 µm, including, by way of non-limiting example, 0.2 µm, 0.22 µm, 0.45 µm, 1.0 µm, 5 µm, 10 µm, and 11 µm, the membrane (2) can be in the form of a sterile cloth-like material or the form of a paper-like material.

A permeable membrane(s) (2) allows optimization of the system in several different ways that are illustrated in FIGS. 15-18. While the reactor system illustrated in the Figures has a total of nine channels (4), the skilled artisan appreciates that any number of channels (4) can be present, from a single channel (4) to a plethora of channels (4), depending on the space available for placement the reactor (1). Similarly, the shape of the channels (4) is not limited to a rectangular prisms or cylinders and can take any shape suitable to fit the space available for the reactor (1).

Figure 12:
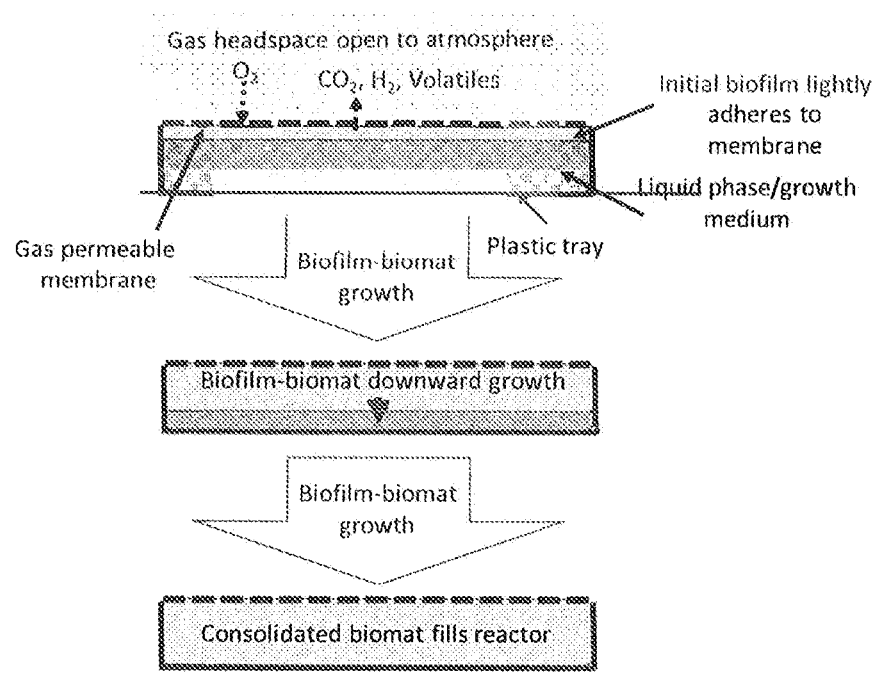
FIG. 12. Growth of biomat in the encapsulated reactor starts when cells attach to the gas-permeable membrane where oxygen is readily available. Over time, biomat grows downward and ultimately fills the space of the reactor, consuming all liquid and nutrients.

In some cases, the membrane (2) is placed in direct contact with the surface of the feedstock, optional liquid media, and inoculum present in the container as shown in FIG. 12. The membrane can also be sealed in contact with the surface of the feedstock, for example, by attaching it to a plastic frame with an integrated rubber gasket.

Figure 15:
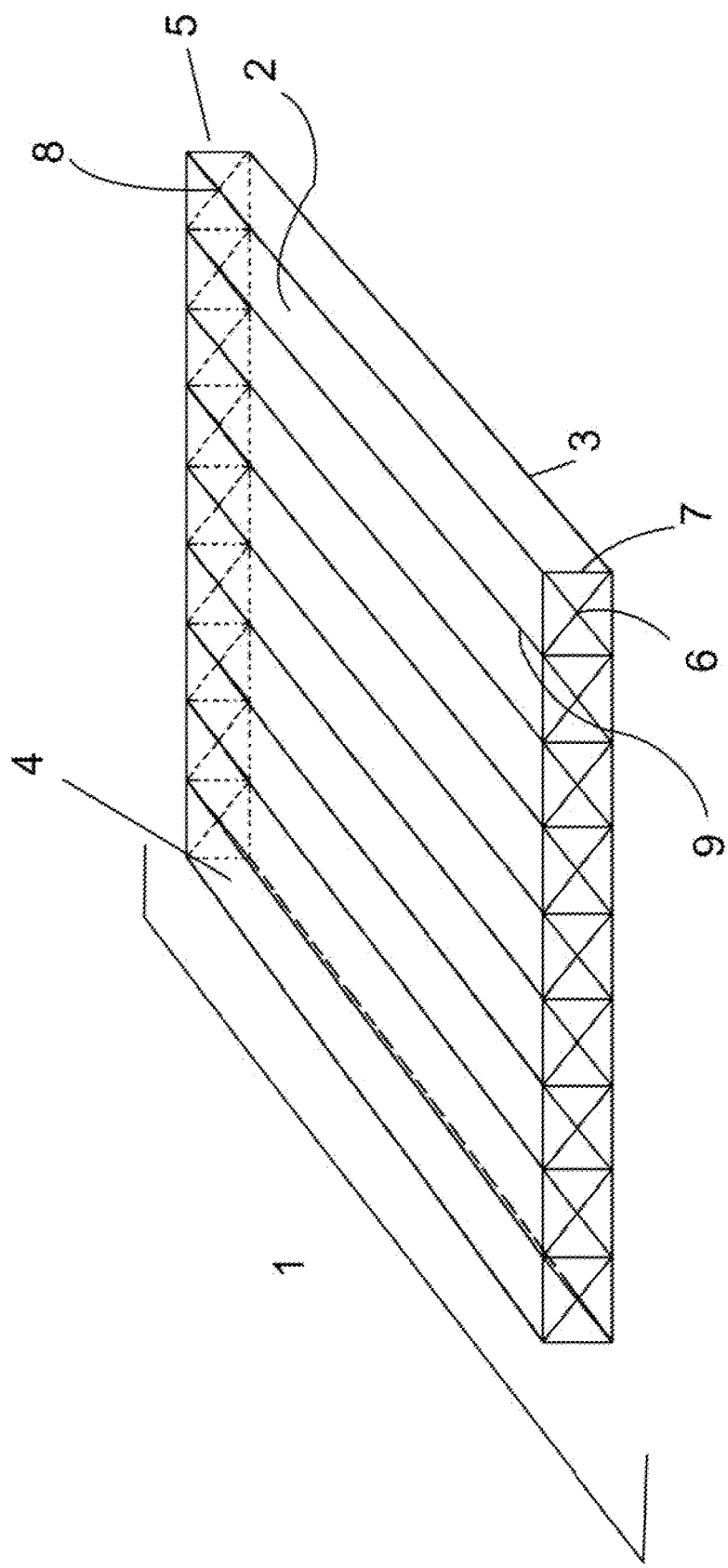
FIG. 15. Basic reactor (1). Multiple channels (4) with shared walls/baffles (9), front valves (6) and back valves (8) and a gas permeable membrane (2) are shown.
Figure 16:
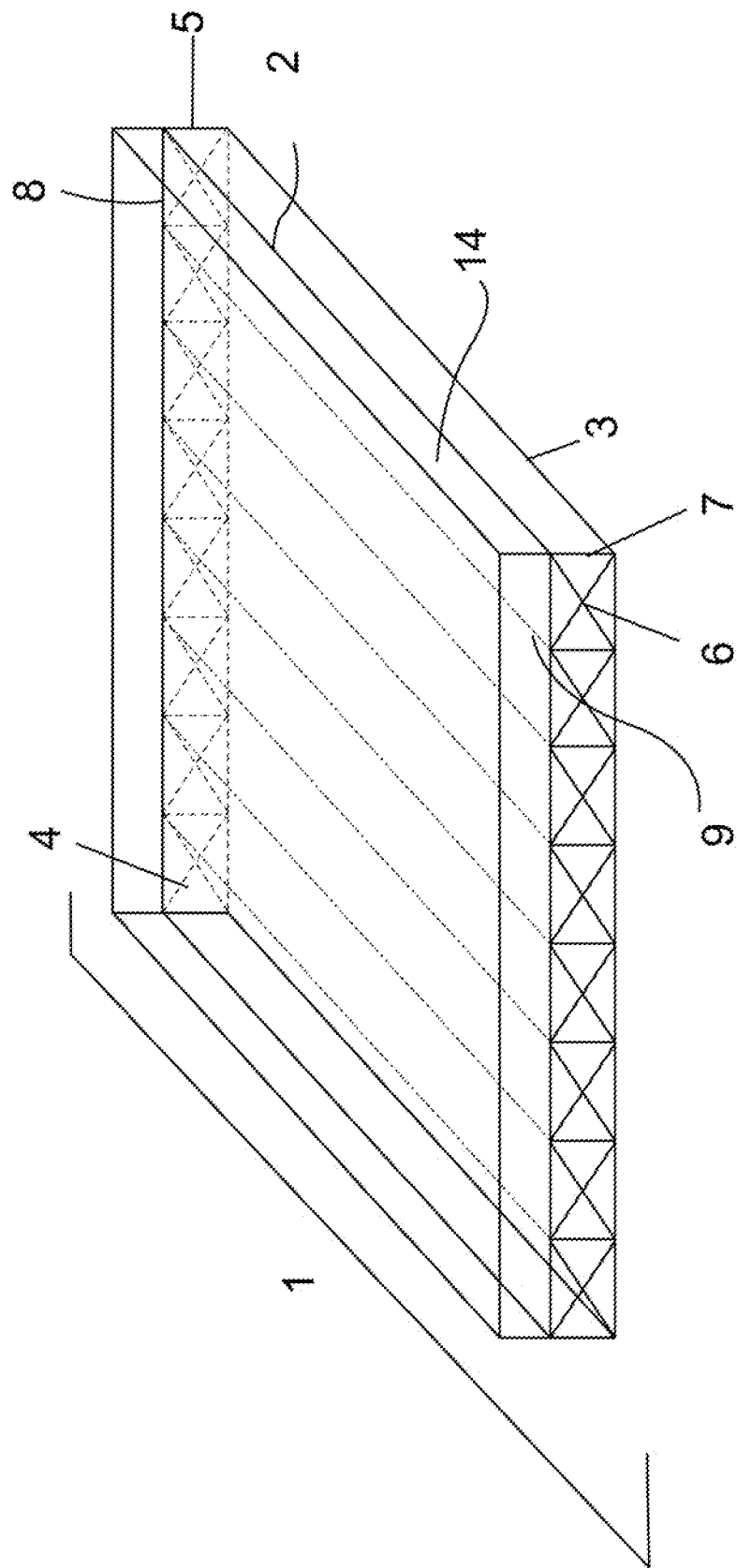
FIG. 16. Basic hermetic reactor (1) with a single gas collection chamber (14).
Figure 17:
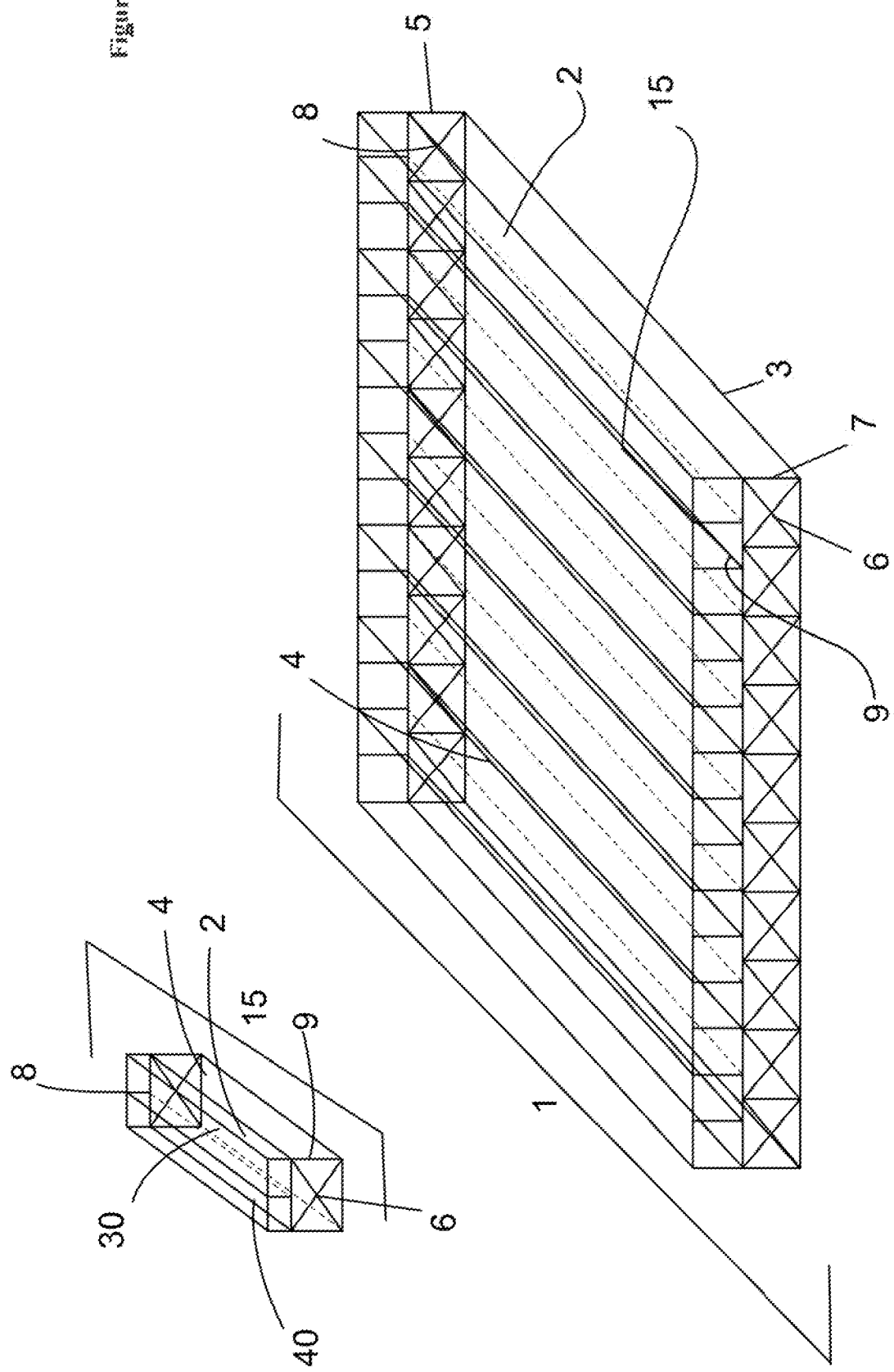
FIG. 17. Basic hermetic reactor (1) with channeled gas collection chambers (15, FIG. 18. Basic hermetic reactor (1) with channeled gas collection chambers (15) having gas specific channels (30, 40) with gas specific permeable membranes (2, 50).

In other instances, the membrane is suspended over the feedstock so that as the fungi grows and consumes oxygen, the membrane drops down towards the mat or onto a baffle system located between the membrane and the feedstock which allow for growth of aerial hyphae. Such a system is shown in FIG. 15. Here, the reactor (1) is comprised of multiple channels (4) which initiate at an inlet valve (6) at the front (7) of the reactor, terminate at an outlet valve (8) at the back (5) of the reactor, and are separated by baffles/walls (9). A gas permeable membrane (2) forms the top of the reactor. The bottom (3) of the reactor can be formed of any suitable substance including, but not limited to both hard and soft plastics such as polyethylene terephthalate, high density polyethylene, polyvinyl chloride, polyactic acid, polycarbonate, acrylic, acetal, nylon, acrylonitrile butadiene styrene, glass, metals such as aluminum, titanium, stainless steel etc. and/or combinations thereof. The baffles/walls (9) can be made of similar materials. Suitable front (6) and back (8) valves include, but are not limited to, one-way valves, 2-way valves, ball valves, butterfly valves, gate valves, plug valves, globe valves, pinch valves, disc check valves, attached valves, detached valves, and/or combinations thereof. The inlet valve (6) serves to provide access to the chamber (4) for delivery of feedstock/media to the chamber while the outlet valve (8) allows removal of exhausted feedstock and/or filamentous fungal biomat. The permeable membrane (2) may comprise a polymeric material, such as, by way of non-limiting example, a polypropylene, a polyethylene, a polytetrafluoroethylene, a polycarbonate, a polyamide (e.g. nylon), a polypyrrolone, a poly(amidoamine) dendrimer composite, a polyvinylidene fluoride, a polyethersulfone, cellulose acetate, a mix of cellulose esters, and/or butadiene-acrylonitrile. The permeable membrane may comprise, additionally and/or alternatively, a glass fiber material, a porous ceramic material, and/or a fabric, such as, by way of non-limiting example, a polypropylene fabric, a polytetrafluoroethylene fabric, and/or a nylon net filter. While the pore size of the permeable membrane (2) typically may be any 0.01 µm increment value or range of values between about 0.2 µm and about 25 µm, including, by way of non-limiting example, 0.2 µm, 0.22 µm, 0.45 µm, 1.0 µm, 5 µm, 10 µm, and 11 µm, the membrane (2) can be in the form of a sterile cloth-like material or the form of a paper-like material. For some uses, the membrane's surface is smooth in texture, for others the surface is rough in texture. In addition, the path for gas diffusion can vary from being essentially direct to following a more tortuous path.

Figure 14:
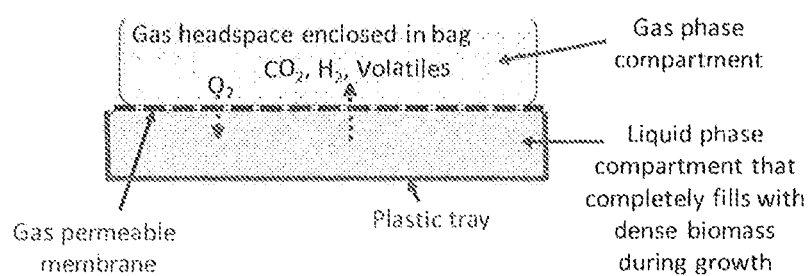
FIG. 14. An attached bag separated from the liquid medium by a gas-permeable membrane is used to supply and capture gasses. The integrated multi-functional membrane allows for ingress of oxygen and egress of $CO_2$ and other produced gases. Fungal biomass grown in the lower liquid compartment (yellow) converts the feedstocks and nutrients into biomat that fills the compartment as it grows. The dense consolidated biomat can be easily harvested by opening the reactor closure system (e.g. Zip-Lock® type) and removal from the bag.

In other situations, the membrane facilitates ingress of oxygen and egress of other gases produced during fungal growth (FIG. 14). In this situation the hermetic reactor (1) has a gas collection chamber (14) that is immediately atop of the gas permeable membrane (2) (see FIG. 16). The gas collection chamber (14) can be made of similar materials to those used for the walls/baffles (9) or the bottom (3) of the reactor; i.e. both hard and soft plastics such as polyethylene terephthalate, high density polyethylene, polyvinyl chloride, polylactic acid, polycarbonate, acrylic, acetal, nylon, acrylonitrile butadiene styrene, glass, metals such as aluminum, titanium, stainless steel etc. and/or combinations thereof. Alternatively, the gas collection chamber is comprised of channels (15) which can mirror the channels (4) of the hermetic reactor (1) or which encompass more than one of the hermetic reactor channels (20) (see FIG. 17).

Figure 18:
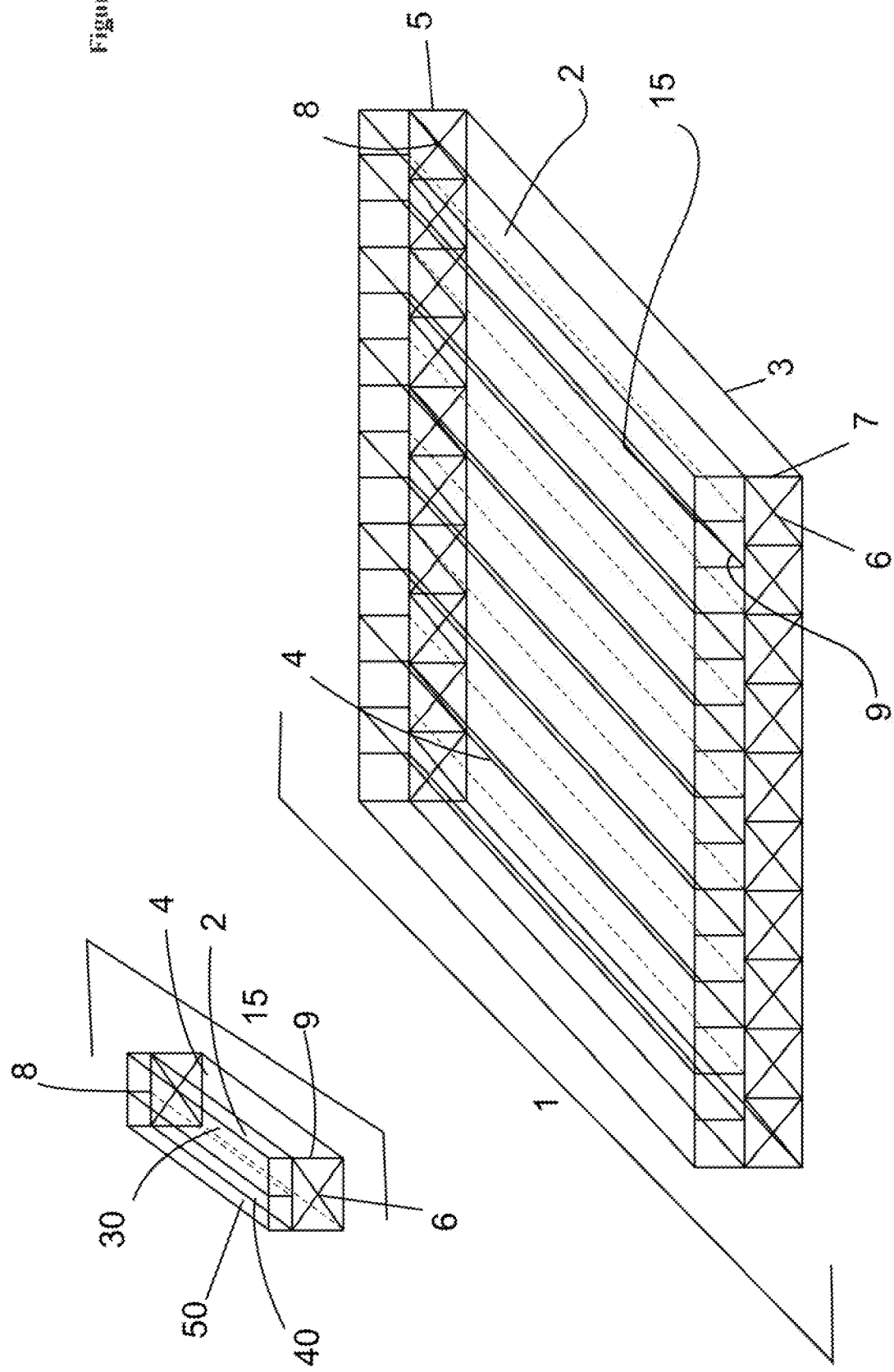
Figure 19:
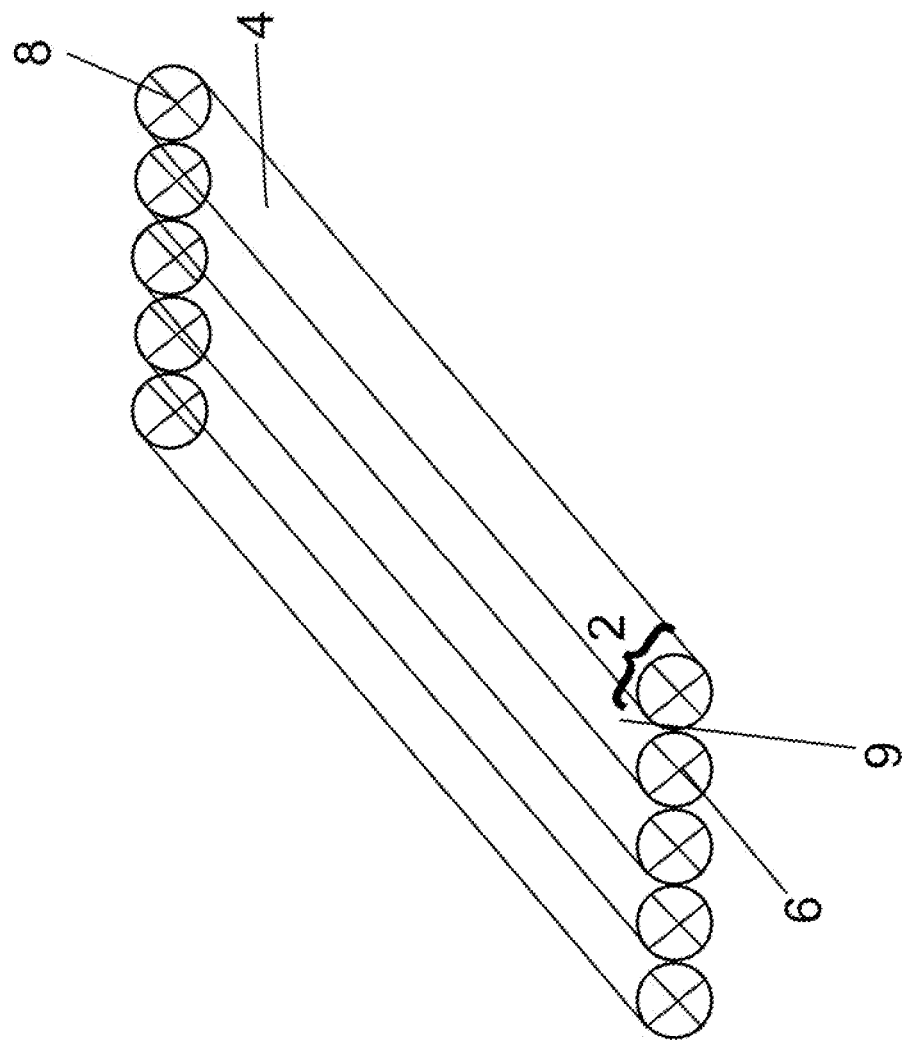
FIG. 19. Basic hermetic reactor (1) with cylindrical channels (4), walls/baffles (9), front valves (6) and back valves (8) and a gas permeable membrane (2).

In yet other systems, separate gas permeable membranes are used for ingress and egress of gases. FIG. 18 illustrates such a system. In this instance, two different gas permeable membranes (2, 50) feed into separate gas collection channels (30, 40) and are present over a single reactor channel (4). This type of system allows ingress, egress, and/or collection and/or separation of distinct useful gases. As an example, one membrane might be calibrated for oxygen passage and the second membrane calibrated for carbon dioxide or hydrogen passage or other relevant gas systems.

The filamentous fungus may be inoculated, and the biomat may be grown, on either or any side of the membrane, including, by way of non-limiting example, an upper side, a lower side, an atmosphere-facing and/or gas headspace-facing side, or a feedstock-facing side. Biomat growth characteristics, including but not limited to density and the side of the membrane on which the biomat grows, may be controlled by controlling various parameters of the bioreactor, e.g. the side of the membrane on which the fungus is inoculated, membrane material, membrane pore size and thickness, temperature, humidity, pressure, wavelength or amount of light and so on. It has generally been found that the best quality of biomat is achieved when the feedstock is constantly in interaction (i.e. physical contact) with the permeable membrane, and the biomat grows on the opposite (i.e. atmosphere- or gas headspace-facing) side of the membrane. Particularly, it may in some embodiments be advantageous for the biomat to grow into a gas headspace that is sealed or otherwise isolated from a surrounding atmosphere and is allowed to become humid as the biomat grows and produces water. It is also advantageous for the bioreactor to be configured to allow the biomat, and in particular hyphae of the filamentous fungus of the biomat, to remain substantially dry (i.e. not in contact with liquid growth medium or other free liquid moisture) during biomat growth.

As the biomat grows, the respiration process of the growing fungus produces water, which accumulates within the bioreactor (generally on the gas phase side of the membrane). In addition to providing a humid environment suitable for further biomat growth, this accumulated water can be collected as a valuable product in its own right and used for any suitable purpose. Thus, one advantage of the present invention is that a portion of the feedstock, which can comprise a waste product such as the feces or urine of an animal, may be converted into clean water. Other feedstocks from which clean water may suitably be produced may comprise, without limitation, any one or more of a sugar (e.g. sucrose, maltose, glucose, fructose, rare sugars, etc.), a sugar alcohol (e.g. glycerol, polyol, etc.), a starch (e.g. corn starch, etc.), a starch derivative, a starch hydrolysate, a hydrogenated starch hydrolysate, a lignocellulosic pulp or feedstock (e.g. sugar beet pulp, agricultural pulp, lumber pulp, distiller dry grains, brewery waste, etc.), corn steep liquor, acid whey, sweet whey, milk serum, wheat steep liquor, industrial liquor, food refinery products/waste streams, agricultural crop residues (e.g. wheat straw, barley straw, rice straw, pea, oat, small grain straw, corn stover, corn fibers (e.g. corn fiber gum (CFG), distillers dried grains (DDG), corn gluten meal (CGM), switch grass, hay-alfalfa, sugarcane bagasse, non-agricultural biomass (e.g. algal biomass, cyanobacterial biomass, urban tree residue), vegetables (e.g. carrots, broccoli, garlic, potato, beets, cauliflower), forest products and industry residues (e.g., softwood first/secondary mill residue, hard softwood first/secondary mill residue, recycled paper pulp sludge, anaerobic digestate), lignocellulosic containing waste (e.g. newsprint, waste paper, brewing grains, used rubber tire (URT), municipal organic waste, yard waste, clinical organic waste, sugar, starch, waste oils, olive oils, olive oil processing waste, cricket excrement, and waste generated during the production of biofuels (e.g. processed algal biomass, glycerol).

As the biomat grows, the respiration process of the growing fungus may also produce one or more gases, e.g. ammonia, hydrogen gas, and/or volatile esters. In embodiments, the membrane may be a selective gas-permeable membrane that allows for separation and/or segregation of at least one gas produced by fungal respiration.

Differences in pressure between one side of the membrane and the other side of the membrane may be leveraged to affect various properties of the filamentous fungus of the biomat. For example, the invention contemplates non-atmospheric pressure on one or both sides of the membrane, such as super- or sub-atmospheric pressure on one side and atmospheric on the other or super-atmospheric or sub-atmospheric on both sides or super-atmospheric on one side and sub-atmospheric on the other. By way of non-limiting example, the growth rate of the biomat may be affected, e.g. a positive pressure on the feedstock side of the membrane may be similar to "force-feeding" the biomass and accelerating biomat production and/or increasing yield, while positive pressure on the "dry" side of the membrane may result in slower production of the biomass, resulting in an altered composition or physical property of the fungal biomass. Conversely, in some embodiments, it may be advantageous for growth rate for the biomat to remain dry during growth, and thus the opposite effect may be observed, i.e. positive pressure results in a "wetter," slower-growing mat while negative pressure results in a "drier," faster-growing mat. Selective application of pressure may also be suitable to determine the type of membrane that is most advantageous for a given application of the bioreactor, e.g. variations in pressure may be more or less advantageous for membranes of a given pore size). Changes in atmospheric pressure in the gas headspace and/or environment may also affect biomat growth characteristics, e.g. aerial hyphae production, production of hyphae, mycelia, and/or filaments, and biomass density, and may even be used to promote inoculation of the filamentous fungus on the membrane.

Figure 29:
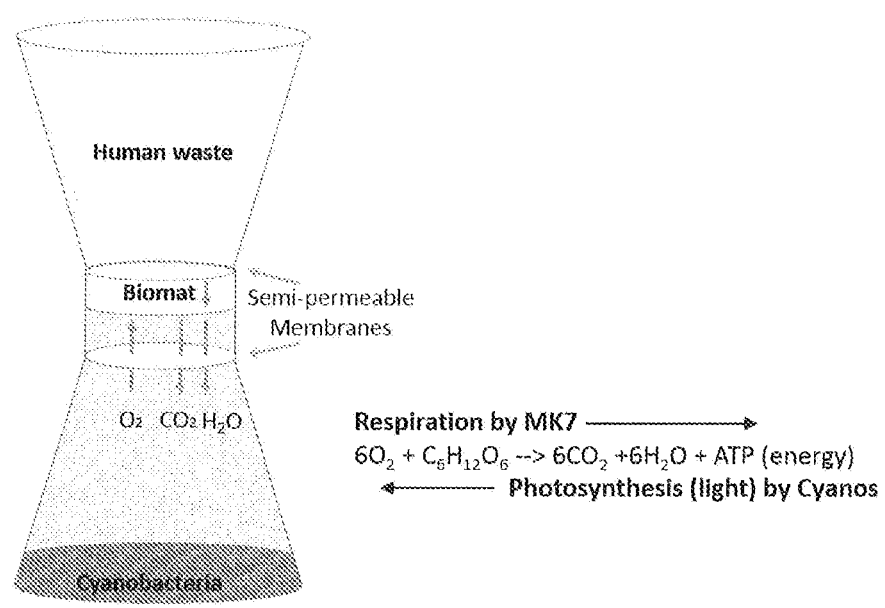
FIG. 29. Exemplary schematic of bioreactor including photosynthesizing cyanobacteria.

In embodiments, cyanobacteria may advantageously be provided on either side of the membrane within the bioreactor, either naturally or by inoculation. Cyanobacteria, whether living or dead, may advantageously contribute to the nutritive characteristics of the feedstock as a source of carbon and nitrogen. Additionally, living cyanobacteria may, as a product of respiration, serve as an oxygen source to promote the growth of the biomass. Either or both of these advantages may make the bioreactors of the present disclosure particularly suitable for various applications where other solutions are inviable, e.g. long-duration crewed space missions. An exemplary schematic of an embodiment of a bioreactor including respiring cyanobacteria is illustrated in FIG. 29.

While in most embodiments a gentle force must be applied to harvest (i.e. remove from the membrane surface) the biomats, in some embodiments the biomats can be "self-harvesting," i.e., they can separate from the membrane spontaneously. The present inventors have particularly observed this phenomenon, e.g., when the biomat has a high water content, when oleic acid is present in the feedstock, and/or when the membrane is relatively thin (e.g. less than 0.2 mm thick), smooth, and characterized by low tortuosity. In some embodiments, self-harvesting may be achieved by application of a pressure. The adhesion strength of the biomat to the membrane may depend, and thus be selected by controlling, any one or more bioreactor parameters, e.g. filamentous fungus species, feedstock composition, membrane characteristics (such as material, pore size, geometry/roughness, etc.), pressure on either side of the membrane and/or pressure differential across the membrane, and so on. It is thus one aspect of the disclosure to provide mats that harvest themselves by separating from the membrane surface spontaneously.

The reactor (1) produces a biomat that serves as a food source, such as a protein source and/or an oil source. However, the biomat can also serve as a leather analog, a bioplastic, a source of biofuel precursors, a biofuel, and/or combinations thereof. In yet other embodiments, the biomat serves to produce organic products such as organic acids, antibiotics, enzymes, hormones, lipids, mycotoxins, vitamins, pigments and recombinant heterologous proteins.

The disclosed biomat reactor fermentation technology enables growth on standard as well as extreme feedstocks and media, such as human waste (urine/feces), and produces a highly consolidated and textured product without the requirement of a separation or concentration step. Relatively high biomass production rates—i.e. at least about 0.05 g/L/h dry biomass (i.e., grams of dry biomass produced per liter of feedstock per hour), or at least about 0.10 g/L/h dry biomass, or at least about 0.15 g/L/h dry biomass, or at least about 0.20 g/L/h dry biomass, or at least about 0.25 g/L/h dry biomass, or at least about 0.30 g/L/h dry biomass, or at least about 0.35 g/L/h dry biomass, or at least about 0.40 g/L/h dry biomass, or at least about 0.45 g/L/h dry biomass, or at least about 0.50 g/L/h dry biomass, or at least about 0.55 g/L/h dry biomass, or at least about 0.60 g/L/h dry biomass, or at least about 0.65 g/L/h dry biomass, or at least about 0.70 g/L/h dry biomass, or at least about 0.75 g/L/h dry biomass, or at least about 0.80 g/L/h dry biomass, or at least about 0.85 g/L/h dry biomass, or at least about 0.90 g/L/h dry biomass, or at least about 0.95 g/L/h dry biomass, or at least about 1.00 g/L/h dry biomass—and/or for example, in the core of batch processes high production (i.e., grams of biomat produced per liter of feedstock) of at least about 10 g/L, or at least about 20 g/L, or at least about 30 g/L, or at least about 40 g/L, or at least about g/L, or at least about 60 g/L, or at least about 70 g/L, or at least about 80 g/L, or at least about 90 g/L, or at least about 100 g/L, or at least about 110 g/L, or at least about 120 g/L, or at least about 130 g/L, or at least about 140 g/L, or at least about 150 g/L, or at least about 160 g/L, or at least about 170 g/L, or at least about 180 g/L, or at least about 190 g/L, or at least about 200 g/L, are achieved without the need for active aeration or agitation. Scale-up of the system vertically, horizontally, and/or in more than two dimensions is simple and does not result in decreased productivity. The produced biomats are typically 0.2 to 2.5 cm thick with a dry matter content of 10-30% and can be readily used for mission critical needs such as meat alternatives, a myriad of other appetizing foods, and building materials.

The fungal biomats grown in the disclosed reactor system can be described as thick pellicles, which in many ways are similar to the microbial biofilms that grow on surfaces, but are consistent with biomats thicknesses described herein and are present at the gas-liquid interface. For example, bacterial cells within biofilms have been shown to withstand extreme disinfection treatments with sodium hypochlorite (bleach) and sodium hydroxide (Corcoran, 2013). The disclosed reactor system takes advantage of the biofilm structure, enabling growth on harsh human and industrial wastes and by-products that may be generated under extreme conditions such as those generated on space missions or by other harsh conditions caused by natural disasters.

The disclosed reactor design incorporates a permeable membrane that sits directly on or suspended just above the liquid surface of a feedstock. In one embodiment, encapsulated reactor design allows for gas exchange with the exterior atmosphere but is hermetically sealed to keep contaminants from entering or gases/liquids from escaping. The encapsulated reactor design can also enable separation of consumable gases from evolved gases by way of gas permeable membrane. To accomplish this, in some instances valves and/or additional porous membranes having the same or different properties are used to form distinct layers between various aspects of the one or more feedstocks and optional liquid culture media.

Figure 13:
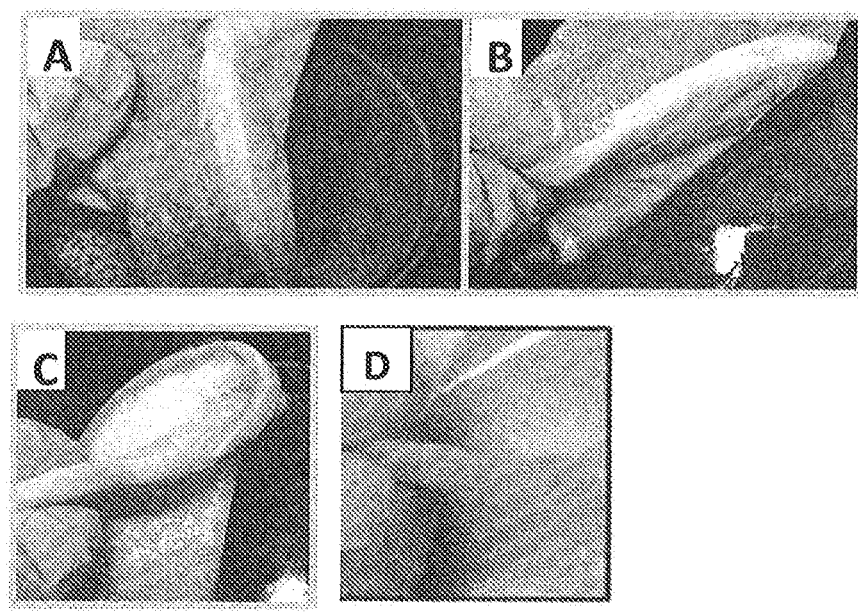
FIG. 13. *Fusarium* strain MK7 biomats grown in five days under static conditions in Petri dishes covered with semi-permeable membranes constructed with (A)-(C) polypropylene and (D) polycarbonate. Essentially no free liquid remained in the Petri dish and all nutrients were incorporated into the biomat. The void/liquid volume of the reactor was essentially filled with biomat.

Rapid biomat growth using the disclosed reactor design has been demonstrated with a variety of permeable membrane materials. FIG. 13 shows an approximately 7 mm thick biomat grown in reactor where the container was a Petri dish covered with a polypropylene membrane which was laid directly on the feedstock/liquid medium surface. The initial biomat formed by direct attachment to the membrane and grew downward into the liquid medium over time (see FIG. 12). By the end of a five-day growth period, essentially all of the feedstock/liquid medium was consumed and dense biomass completely filled the volume underneath the membrane.

The biomat produced only mildly adheres to the membrane and was easily harvested by simply peeling away the biomat from the membrane (see FIGS. 13A-13D). Additional experiments with polycarbonate membranes have produced similar results (data not shown). Thus, the total reactor volume can be efficiently utilized to produce dense, easily harvested biomass. By way of non-limiting example, bioreactors of the present invention can take the form of a sealed "envelope," comprising four membranes: an outer upper membrane, an inner upper membrane, an inner lower membrane, and an outer lower membrane. In such embodiments, feedstock may be provided between the inner upper membrane and the inner lower membrane, whereby the feedstock is "sandwiched" between gas headspaces on either vertical side (i.e. between the outer and inner upper membranes and between the outer and inner lower membranes). Biomat can thus grow on the outer surfaces of the inner membranes, into the gas headspace on either side of the feedstock, while still being at least partially isolated from a surrounding atmosphere due to the outer membranes (which may in embodiments be gas-permeable or gas-semi-permeable membranes). The "envelope" bioreactor may be a highly volume-efficient bioreactor that may be used when space is at a premium, e.g. aboard a spacecraft or in emergency and rescue situations.

The biomats commonly produced in the disclosed reactors are highly dense, as described herein, and, depending on the fungus and growth conditions, exhibit a fibrous texture. Production of a fibrous biomass can be crucial for certain mission critical products such as foods that require texture to simulate meat, as well as fibrous materials that simulate leather and wood. The dense nature of the biomass also enables easy harvesting without the need for a concentration step (e.g., centrifugation, filtration). The density of the biomats can range from about 0.01 g dry biomat weight/cm3 to about 1 $g/cm^3$, and any subrange within this range. In some embodiments, the density can be greater than about 0.01, greater than about 0.02, greater than about 0.03, greater than about 0.04, greater than about 0.05, greater than about 0.06, greater than about 0.07, greater than about 0.08, greater than about 0.09, greater than about 0.1, greater than about 0.2, greater than about 0.3, greater than about 0.4, greater than about 0.5, greater than about 0.6, greater than about 0.7, greater than about 0.8, greater than about 0.9, or greater than about 1 $g/cm^3$.

Figure 23:
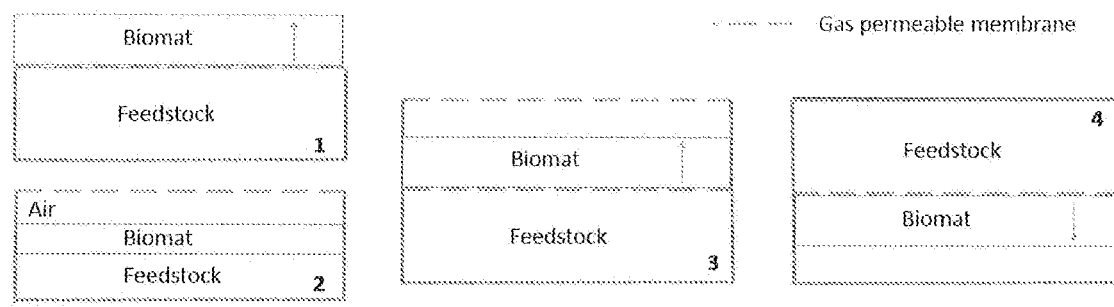
FIG. 23. Generalized schematic of various bioreactor configurations.

Referring now to FIG. 23, several different bioreactor configurations are illustrated, each of which is within the scope of the present disclosure. In the configuration labeled 1, the feedstock is disposed below and in physical contact with the membrane, and the biomat grows upwardly from the upper surface of the membrane (although in some embodiments, fungal material may also grow downwardly from the lower, i.e. feedstock-side, surface of the membrane). In the configuration labeled 2, the biomat grows directly on the surface of the feedstock (i.e. without a membrane present between the biomat and the feedstock) into a gas headspace, and the feedstock, biomat, and headspace are separated from a surrounding environment by a membrane; membranes of this embodiment may be similar to, or different from, the membrane disposed between the feedstock and the biomat in other embodiments. In the configuration labeled 3, two membranes are provided: a lower membrane separating the feedstock from the biomat (as in the configuration labeled 1) and an upper membrane separating the biomat and gas headspace above the biomat from a surrounding environment (as in the configuration labeled 2). In the configuration labeled 4, an "upside-down" bioreactor scheme is provided, wherein the feedstock is provided on the upper surface of the membrane and the biomat grows downwardly from the lower surface of the membrane into a gas headspace and/or the surrounding environment (although in some embodiments, fungal material may also grow upwardly from the upper, i.e. feedstock-side, surface of the membrane).

Figures 24A, 24B:
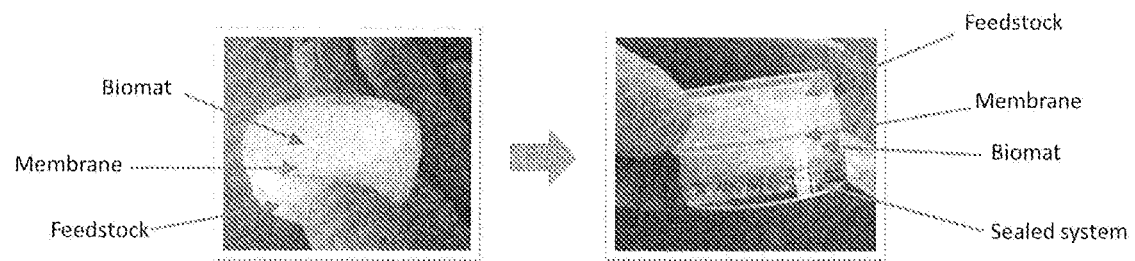
FIGS. 24A and 24B. Illustration of hermetic embodiment of bioreactor configuration "1" before and after production of a biomat, respectively.

Referring now to FIGS. 24A and 24B, a "hermetic" (tightly sealed against the environment) embodiment of a bioreactor according to the configuration labeled "1" in FIG. 23 is illustrated, before (FIG. 24A) and after (FIG. 24B) production of the biomat. As FIG. 24B illustrates, fresh water produced by respiration of the filamentous fungus has condensed and accumulated on the gas-phase side of the membrane.

Figure 33:
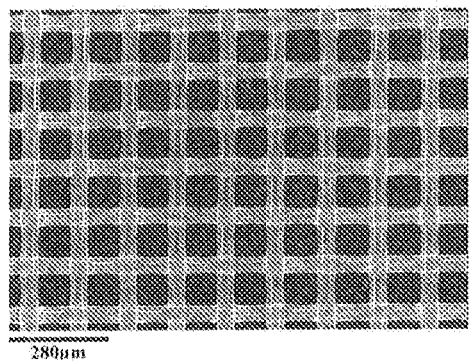
FIG. 33. Illustration of nylon net filter membrane.

Referring now to FIG. 33, a nylon net filter membrane is illustrated. In this embodiment, the nylon net filter consists of two nylon membranes (pore size 11 μm) that are "stacked" (i.e. placed in physical contact such that a second surface of the first membrane abuts a first surface of the second membrane) to reduce the effective porosity of the membrane and allow the membrane to remain above the surface of the feedstock. Membranes of this type are suitable for growing fungal biomats, according to the present disclosure.

Figure 35:
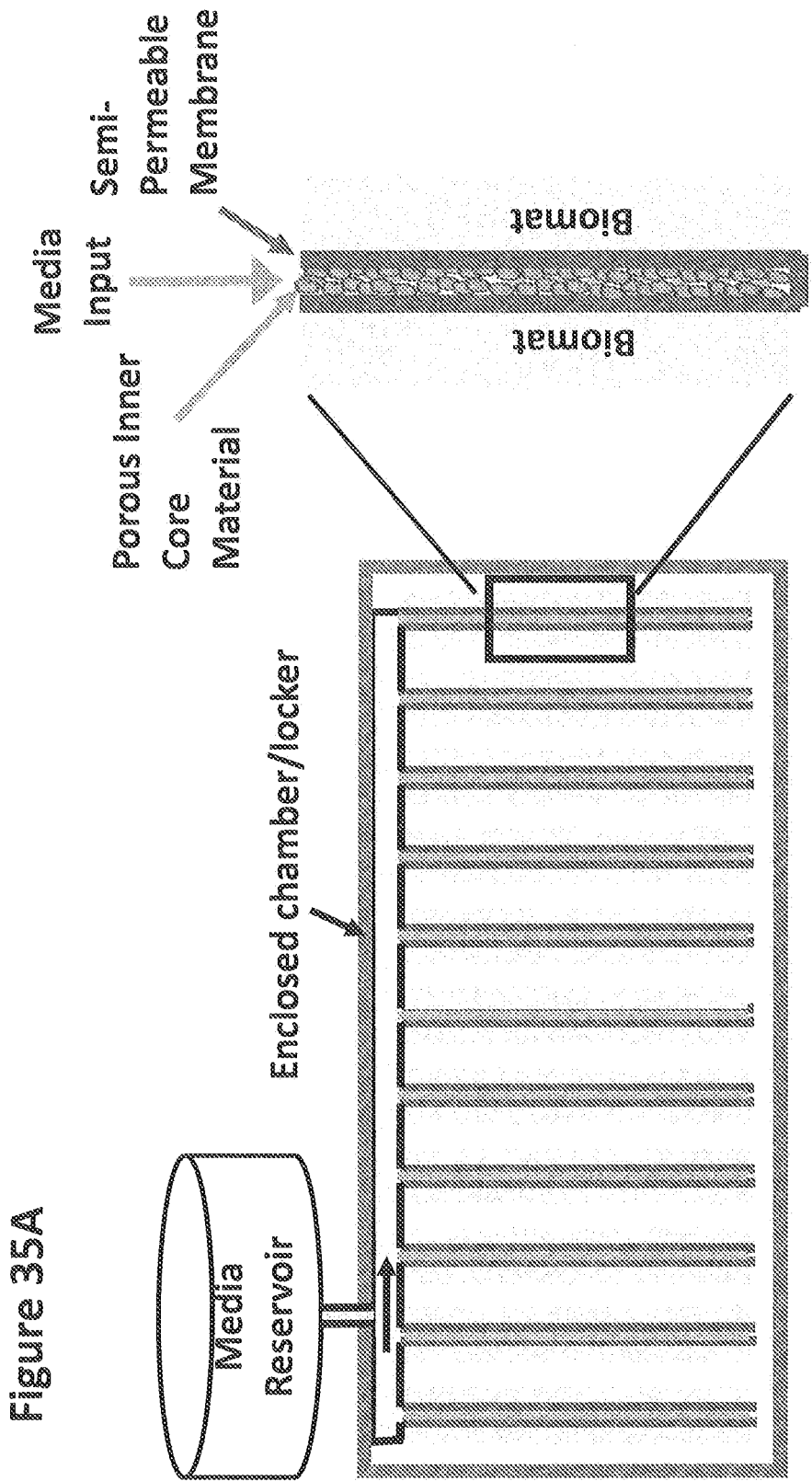
FIG. 35A. Illustration of membrane envelope bioreactor (MEBR).
FIG. 35B. Inset of FIG. 35A illustrating a detail of the membrane envelope bioreactor.

Referring now to FIGS. 35A and 35B, a membrane envelope bioreactor (MEBR) is illustrated. In this embodiment, the MEBR comprises an enclosed chamber or locker, in fluid communication with a media reservoir and enclosing a plurality of membrane envelopes. As illustrated in FIG. 35A, as growth medium enters the MEBR from the media reservoir, it flows into each of the plurality of membrane envelopes. As illustrated in Figure each membrane envelope comprises a porous inner core material surrounded on each side by a semi-permeable membrane. As growth medium flows through the membrane envelope, it comes into contact with and flows through the porous inner core material, enabling a filamentous fungal biomat to access the growth medium through the semi-permeable membrane and thus grow on an outer surface of the semi-permeable membrane.

It is to be expressly understood that various other configurations of bioreactors are contemplated and are within the scope of the present invention. By way of non-limiting example, one such configuration is a "trough" bioreactor, in which an upward-opening arcuate hydrophilic membrane having a relatively small pore size (e.g. 0.2 μm) is provided as a trough, and a hose with holes therethrough is provided longitudinally parallel to the membrane. Feedstock may be provided, e.g. by spraying, through the holes in the hose to ensure that an inner/upper arcuate surface of the trough is evenly saturated with growth medium at all times. Biomass may then grow on the opposite side of the trough membrane, i.e. an outer/lower surface, and may in embodiments thereby be enabled to fall away from the membrane under its own weight when a certain mass is attained.

Use of the Biomat Reactors in Zero Gravity

The primary physical force controlling formation and growth of the biomat in the disclosed reactor is attachment to the membrane. Without being bound by theory, it is believed that biomats grown in the disclosed reactor will not be impacted by the zero-gravity conditions experienced during space flight. Gravity driven directional growth or growth controlled by physical mixing or flow is not the overriding factor in the system, as it tends to be in gravity environments. Previous experiments in space successfully demonstrated fungal growth European Space Agency, Expeditions 25-28, Growth and Survival of Colored Fungi in Space (CFS-A)), providing an additional measure of confidence that the disclosed reactor system will function in a space environment.

For space missions and ease of deployment, freeze dried inoculum and essential ingredients to support growth on specific feedstocks (if needed) can be preloaded in the reactor. Astronauts and space travelers can then prepare the feedstock, inoculum, and any media components. Incubation time is dependent on the feedstocks, the strain of microorganism, and other growth parameters such as pH, temperature and water content. The incubation conditions are simple in that fermentation is conducted under static conditions where the reactor is simply allowed to incubate in place. Dense consolidated biomats are harvested by simply opening the reactor closure (e.g. a Ziplock®-type) and removing the mats.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims. The examples and figures are provided for the purpose of illustration only and are not intended to limit the scope of the present invention. Each publication or other reference disclosed herein is incorporated herein by reference in its entirety, to the extent that there is no inconsistency with the present disclosure.

EXAMPLES

Example 1: Growth of Strain *Fusarium* Strain MK7 and Other Fungi in Static Tray Reactors Filamentous acidophilic *Fusarium* strain MK 7, *Ganoderma lucidum* (Reishi; FIG. 1A), *Pleurotus ostreatus* (pearl oyster, FIG. 1B: and blue oyster, FIG. 1C), *Sparassis crispa* (cauliflower; FIG. 1D), *Hypsizygus ulmarius* (elm oyster; FIG. 1E), *Calvatia gigantea* (giant puffball; FIG. 1F), and *Fusarium venenatum* biomats were grown in shallow static tray reactors as described in PCT/US2017/020050.

Example 2. Growth of *Fusarium* Strain MK7 Biomat on Nutrient Medium Refreshed Daily (Semi-Static Conditions)

Figure 2:
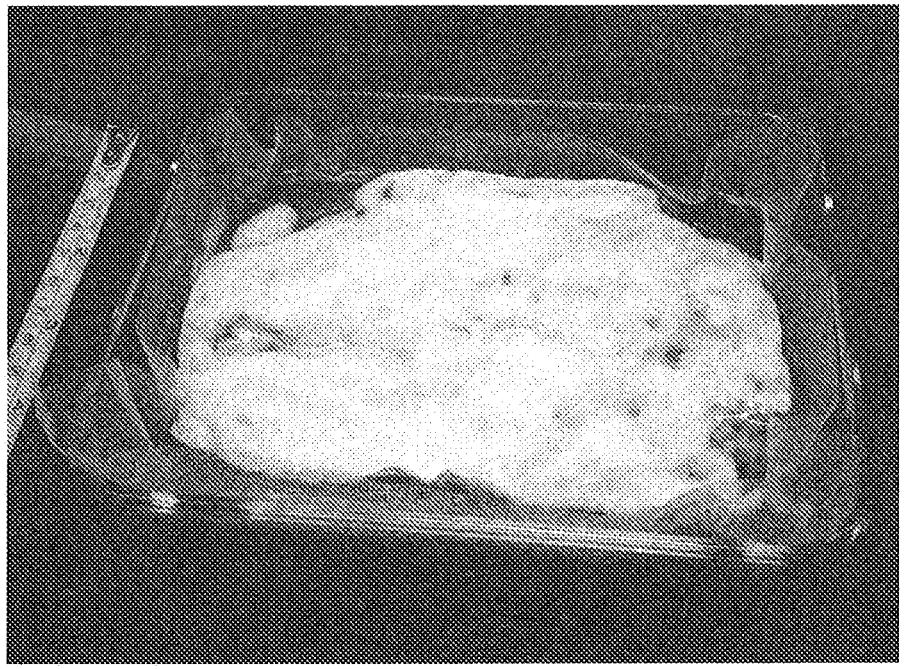
FIG. 2. Three-centimeter-thick biomat of *Fusarium* strain MK7 that was formed in liquid nutrient medium that was refreshed daily (after day 4). Nylon mesh screen underneath the biomat is shown and used for lifting and moving the biomat to fresh medium.

Dense *Fusarium* strain MK7 biomats approximately 3 cm thick were grown in 21 days on nutrient medium that was refreshed daily. The biomats were generated using sterile MK7-1 liquid medium (described in PCT/US2017/020050) containing 7.5% glycerol at pH 3.0 in 12.7×17.8 cm Pyrex® glass trays. To initiate the experiment, 200 mLs of the nutrient medium was inoculated with 5% (volume/volume) of *Fusarium* strain MK7 culture in the late exponential growth phase as described previously in PCT/US2017/020050. 200 mLs of the inoculated medium were added to each of three sterile trays that were lined with sterile coarse nylon mesh screens. The cultures were incubated undisturbed for 4 days at room temperature (~22° C.) to allow development of the initial biomat layer that formed at the surface of the liquid. After 4 days of growth, the biomats were gently lifted out of the tray using the nylon mesh screens and were tilted at a 45 degree angle to allow the liquid to drain out of the mats. The biomats were allowed to drain in this position until less than one drop of liquid dripped out every five seconds. Sufficient draining occurred, on average, after about 3 minutes. The drip-dried biomats in their screens were placed in fresh preweighed 12.7×17.8 cm Pyrex® trays containing 200 mL of fresh MK7-glycerol medium (described in PCT/US2017/020050). Trays with biomats were re-weighed. The process of moving the biomats to another tray containing fresh medium was repeated on approximately a daily basis for 17 more days. Sampling of one of the biomats occurred on days 12, 15 and 21 and the moisture contents of these biomats were determined. The average moisture content of the biomats was 17.3% (std dev=0.7) and this value was used to calculate dry biomass production over the duration of the experiment. Dry biomass production was linear from day 4 through day 18 ($r^2$=0.995) after which biomass weight stabilized at about 2.5 Kg dry/$m^2$ (FIG. 1, y-axis normalized to a per $m^2$ basis, growth is typically exponential between day 0 and day 4). The average growth rate over this time period of linear growth was 6.04 g/$m^2$/h. FIG. 2 shows a ~3 cm thick biomat that developed after a total of 21 days growth using this method.

Figure 36:
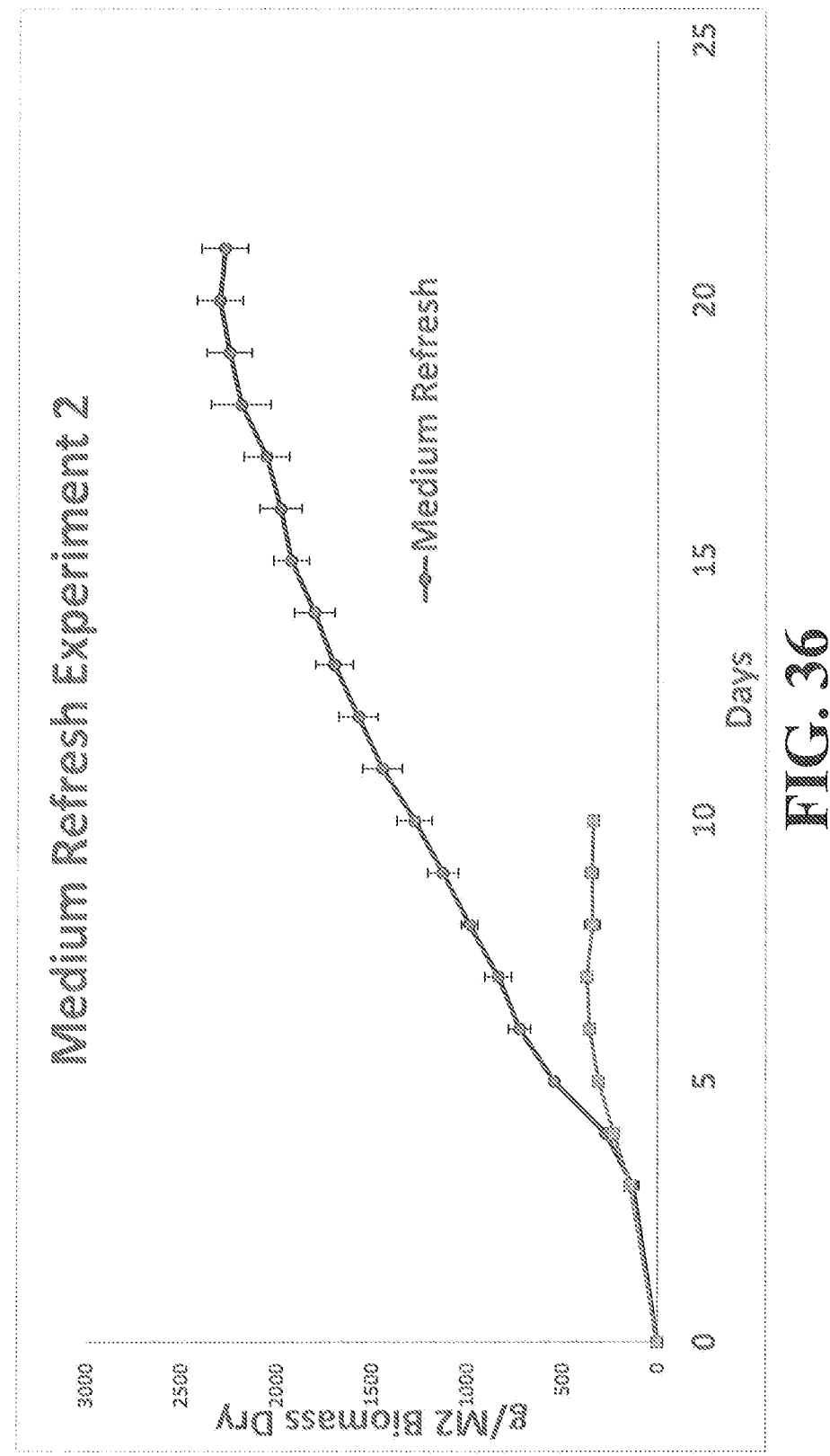
FIG. 36. Illustration of biomat growth rates in the trays with and without refreshing growth medium.

To confirm these findings, the same experimental protocol was repeated, this time alongside control trays in which the medium was not refreshed during biomat growth. The results of this comparative experiment are illustrated in FIG. 36. As FIG. 36 shows, the trays in which the medium was refreshed showed biomat growth that was approximately three times as rapid (109 vs. 34 grams dry biomass per square meter per day), for a period twice as long (21 vs. 10 days). Surprisingly, it was found that refreshing the growth medium did not merely perpetuate the same growth rate as the control, but in fact accelerated growth; where both the refreshed trays and the control showed similar amounts of growth up to day 3 (before the medium was refreshed for the first time), a sharp increase in growth rate was observed in the refreshed trays beginning between days 3 and 4, and this increase persisted over nearly the entire length of the experiment.

Example 3. Growth of Biomats Under Continuous Flow Conditions

Figure 3:
FIG. 3. Continuous flow system designed to continuously feed *Fusarium* strain MK7 biomat growth and remove nutrients from media. Biomats shown in channels after 7 days of growth from the time of inoculation.

A continuous flow bioreactor system was fabricated to demonstrate growth of biomats on the surface of flowing liquid media. The system was fabricated from a 2.44 m long clear plastic roofing panel with a series of corrugations that were used as flow channels (FIG. 3). The ends of each of the channels were dammed with silicon (100% Silicone, DAP Products Inc., Baltimore, MD) enabling liquid to be retained within the channels. Flow was facilitated through the channels by delivery of liquid media to one end of the channels via a peristaltic pump, with the liquid exiting the other end of the channels through holes in the bottom of the channels. The whole plastic roofing panel system was slanted at an angle of 1 cm rise per 1 m run to enable about 500 mL of liquid to be retained in each channel and a consistent flow being a function of the amount of liquid and the angle of the inclination.

The panel system was sanitized and wrapped in Saran®-like plastic wrap to isolate the system from the surrounding room environment. Sterile air was pumped under the plastic wrap at a rate of 400 mL/min creating a positive pressure on the system. To initiate development of a biomat prior to starting flow, a 500 mL volume of nutrient medium inoculated with the desired filamentous fungus was added per channel and allowed to incubate under quiescent/static conditions for 4 days. After 4 days, the peristaltic pump delivered a continuous pulsed flow of 400 mL/d to "feed" the biomats (ON at 2.016 mL/min for 49 min, 39 sec; OFF for 5 h 10 min 21 sec). Two independent experiments were conducted with each experiment using two separate flow channels as replicates (FIG. 3).

Figure 4:
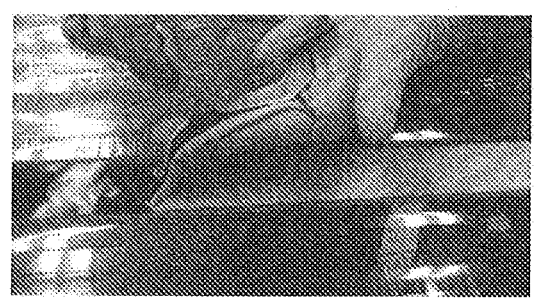
FIG. 4. Biomat growth after 10 days of growth from the time of inoculation (6 days under continuous flow+4 days under quiescent/static conditions).

Consolidated biomats were harvested after 10 days of growth on the nutrient medium (4 days under quiescent/static conditions followed by 6 days under continuous flow; FIG. 4). Average dry weight of the produced biomass was an average of 2.38 g for the replicate flow channels. During the continuous flow periods (day 4 to day 10) the average removal rates of C and N from the flowing liquid medium by the growing biomats were 11.9 and 1.2 mg/L/h, respectively. C and N removal rates from the liquid medium were determined by measuring liquid volume and total C and N inputs and outputs from the bioreactor system using a Costech total C and N analyzer (ECS 4010, Costech Analytical Technologies, Valencia, CA). Thus, the continuous flow system supported biomat growth at the surface. The experiments also served as a laboratory-scale demonstration for continuous feed of *Fusarium* strain MK7 biomat growth and production of consolidated biomats. It should be noted that other feedstocks, flow rates and resulting growth rates can be achieved with this type of system. For example, with 10% glycerol in MK7-1 medium (described in PCT/

US2017/020050) at pH 2.8, expected yields are greater than 40 grams dry biomass per day per m².

Figure 5:
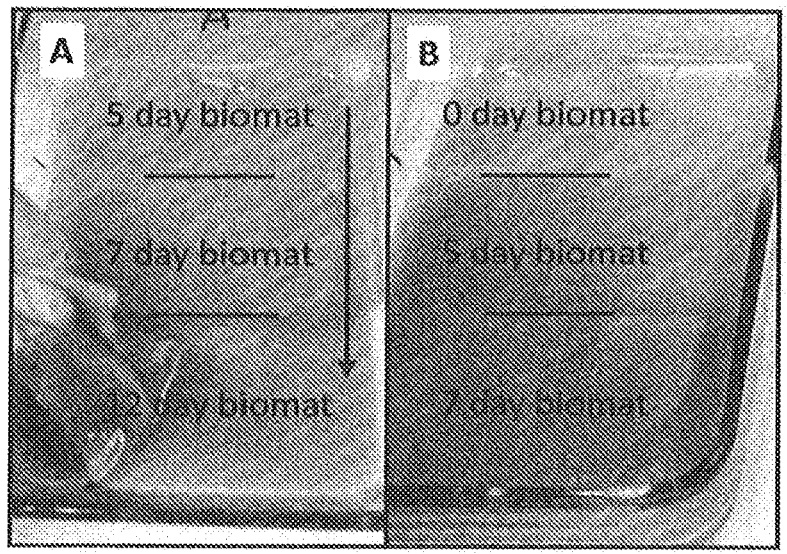
FIG. 5. Semi-continuous production of biomat showing (A) removal of the most mature portion of the biomat at day 12. After harvesting ⅓ of the most mature biomat at the lower end of the tray, the remaining biomat is physically moved down in the direction of the arrow until the edge of the biomat touches the end of the tray (B). Moving the biomat creates a fresh open space at the upper end of the tray where new biomat forms.
Figure 6:
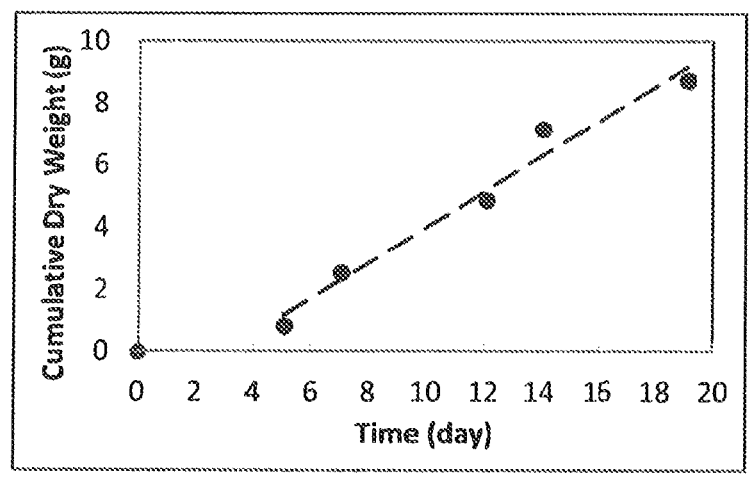
FIG. 6. Cumulative production of biomass over time using the semi-continuous production method. Dashed line is the linear regression line for day 5 through day 19 (y=−1.52, $r^2$=0.973). Error bars are standard deviations of the mean of three replicate trays. Error bars are not visible when smaller than data point symbol.

Example 4. Semi-Continuous and Continuous Production of *Fusarium* Strain MK7 Biomats Dense *Fusarium* strain MK7 biomats were grown and harvested on a semi-continuous basis over a period of 19 days. The biomats were generated using acid whey as the feedstock/carbon source supplemented with ½ strength MK7-1 medium salts (described in PCT/US2017/020050) adjusted to pH 4.0. To initiate the experiment, 200 mL of the nutrient medium inoculated with *Fusarium* strain MK7 (5% volume/volume) in the late exponential growth phase was added to sterilized 12.7×17.8 cm Pyrex® glass trays, which were then covered with Saran® wrap and incubated at room temperature. After 5 days of growth, ⅓ of the biomat from one end of the tray was removed by cutting and removing a 5.9×12.7 cm section of biomat (FIG. 5A). The remaining ⅔ of biomat was then physically moved over to the open area of medium that was created by removal of the ⅓ portion of biomat. The biomat was shifted by physically grasping it with sterile gloved fingers and pulling the biomat over until it touched the end of the tray to open medium with no formed biomat at the other end of the tray (FIG. 5B). The process of harvesting a ⅓ section of the most mature portion of the biomat and then moving the remaining ⅔ of biomat over the open area was repeated periodically. 50 mLs of medium were aseptically removed from the tray every 4 days and replaced with 50 mLs of fresh sterile medium (acid whey with ½ strength MK7-1) to replenish the nutrients removed from the liquid medium by removal of the biomat. Dry biomass production using this method yielded 0.57 g/day per tray or 25.2 g/d/m² between days 5 and 19 (FIG. 6). Thus, a semi-continuous production system was demonstrated whereby the most mature end of the biomat was harvested at an average rate of 1.56 cm/day and fresh biomat growth was initiated in the open area of medium at the other end of the tray.

Figure 7:
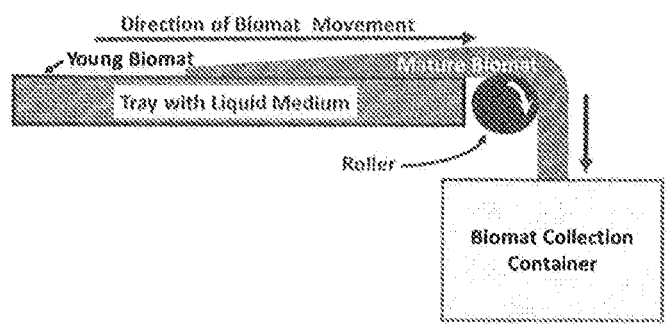
FIG. 7. Continuous production of biomat showing removal of the most mature portion of the biomat at the right. While continuously harvesting the most mature biomat at the right side of the tray, fresh open space is created at the left end of the tray enabling new biomat to form. Liquid medium in the tray can be replenished and/or augmented as required or continuously.

The system is also amenable to continuous harvesting and growth of a biomat whereby continuous removal is facilitated by a roller wheel that is attached to the mature end of the biomat (FIG. 7). The roller wheel slowly turns and harvests the mature biomat and at the same time creates an open medium for growth of new biomat at the other end of the tray. The roller wheel turns and harvests the biomat at a rate of 1.56 cm/day to reproduce the semi-continuous system described above. It is desirable that the nutrients in the liquid medium be replenished at the rate of nutrient removal by the biomat.

Example 5. Membrane Encapsulated Bioreactors

Dense *Fusarium* strain MK7 biomats were grown in liquid growth medium that was encapsulated in a bioreactor system with no gas headspace. Sterile Petri dish bottoms (55 mm diameter) were filled to the brim with 57 mL of inoculated MK7-1 medium (described in PCT/US2017/020050) containing 8% glycerol. Gas permeable/semi-permeable membranes of polypropylene and polycarbonate were placed directly on the surface of the liquid medium and sealed tightly with rubber bands. No gas headspace was provided at the start of the growth period.

Figure 8:
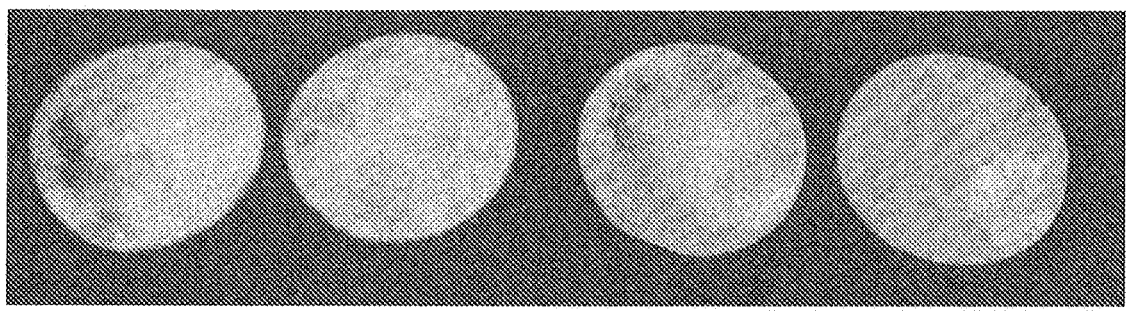
FIG. 8. Orange pigmentation of *Fusarium* strain MK7 biomats (two excised disks at the right) after irradiation with UVB light for four hours. Two excised disks from non-irradiated control biomats are shown at the left.

After inoculating the medium and sealing the membranes, the bioreactors were allowed to sit undisturbed until harvest. FIG. 8 shows the ~5 mm and ~1 mm thick biomats of *Fusarium* strain MK7 that grew directly underneath the polypropylene (FIGS. 13A-13C) and polycarbonate (FIG. 13D) membranes in five days, respectively. The biomats mildly adhered to the membranes and could be easily harvested by simply peeling away the biomats from the membranes (FIG. 13).

Figure 9:
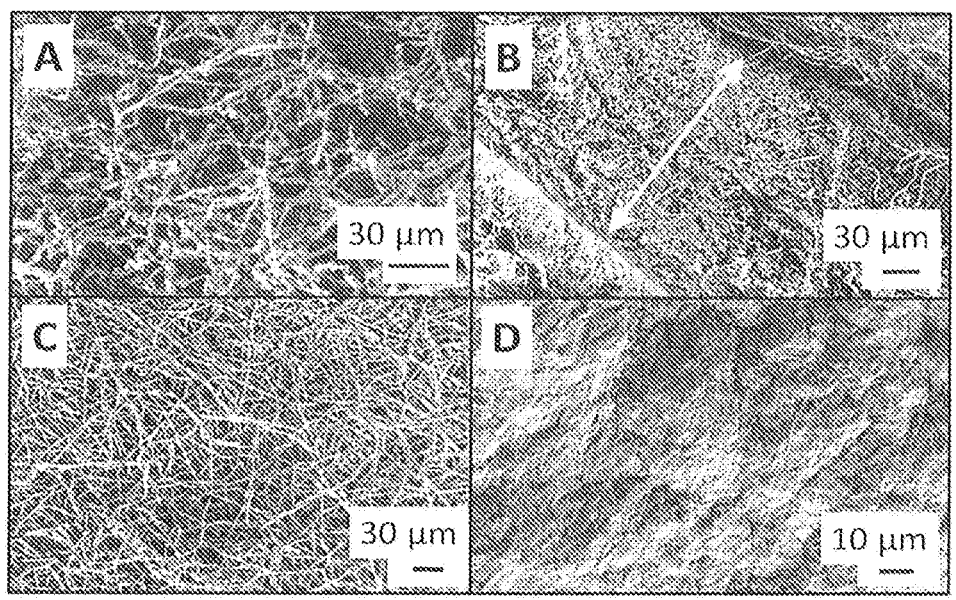
FIG. 9. Field emission scanning electron microscopy of 4 day old *Fusarium* strain MK7 (ATCC Accession Deposit No. PTA-10698) biomats produced using MK7-1 medium (described in PCT/US2017/020050) with glycerol, corn starch and corn steep liquor. Images A, B and C show biomat with extracellular matrix (ECM) removed by ethanol washing. A) View of top surface of biomat with aerial hyphae. B) Cross-section of the dense bottom layer with arrow delineating the layer. The cross-sectional view was created by cutting the biomat with a razor blade. The bottom of the biomat is shown at the bottom left corner of the image and the poorly adhering transition layer above the dense bottom layer is shown at the upper right corner. C) View of bottom surface of biomat. D) View of bottom surface of biomat with ECM in place (i.e., ECM not removed with ethanol wash).

Example 6: Production of Pigments and Vitamin $D_2$ by Irradiation of *Fusarium* MK7 Biomats with UVB UVB light (290-320 nm) was used to trigger pigment production by *Fusarium* strain MK7 biomats. *Fusarium* strain MK7 biomats produced in 3 days on 7.5% glycerol MK7-1 medium (described in PCT/US2017/020050) were irradiated with UVB light for a period of 4 hours. The UVB light was emitted from a 50 W bulb (Slimline Desert 50 UVB T8 fluorescent bulb, 46 cm; Zilla, Franklin, WI) placed 10 cm above the biomat. Orange pigmentation was visually detected after 0.5 h of irradiation and was pronounced after 4 h of irradiation (FIG. 9). In addition, biomats that have not been exposed to UVB light have a vitamin $D_2$ content of less than 50 IU/100 g of biomat whereas after UVB light exposure for approximately 12 hours the vitamin $D_2$ content is increased to approximately 1.2 million IU/100 g biomat.

Example 7: *Fusarium* Strain MK7 Biomats Grown on a Mixture of Glycerol, Starch and Corn Steep Liquor

*Fusarium* strain MK7 biomats were produced from a mixture of glycerol, starch, corn steep liquor and MK7-1 salts (described in PCT/US2017/020050) in as little as 4 days. Glycerol was purchased from Duda Energy LLC (Decatur, AL; 99.7% Purity; USP Grade; Lot #466135376340); 100% Argo Corn Starch manufactured by Argo Food Companies, Inc (Memphis, TN) was purchased from Albertson's supermarket in Bozeman, MT, and the corn steep liquor was purchased from Santa Cruz Biotechnology, Inc. (Dallas, TX; Lot #B0116). The growth medium was a mixture of 7.5% glycerol (weight/weight), 2.5% starch and 2.5% corn steep liquor with MK7-1 salts. The mixture was adjusted to pH 3.3 by adding an appropriate amount of HCl and boiled for 15 minutes in a suitable container. After cooling to room temperature, the pH of the mixture was readjusted to 3.3 and then inoculated with 5% *Fusarium* strain MK7 inoculum (vol/vol) as prepared in PCT/US2017/020050. Aliquots of 1.5 L inoculated media were added to three sanitized 0.25 m² polypropylene trays, placed in a sanitized tray rack system that was completely covered with aluminum foil to create dark conditions, and incubated at 23°±1° C. The filamentous fungal biomats that grew at the surface of the medium were harvested after 4 days by simply lifting the biomats from the trays.

The average final pH of the residual liquid in the three trays was 4.45 (standard deviation=0.14). Three 56.7 cm² circular portions were cut out and removed from each of the biomats at random positions and these portions were dried at 50° C. for 48 h to obtain dry weights. The average biomass dry weight (standard deviation) was 124.6 g/0.25 m² (43.4) or 498.4 g/m² (173.6). The mean thickness of the moist biomats were 7.5 mm and the mean density on a dry weight basis was 0.66 g/cm 3.

To expose the biomat filaments and enable examination by Field emission scanning electron microscopy (FE-SEM), the extracellular matrix (ECM) between the filaments were removed by washing with ethanol. To accomplish this, 1 cm² portions (1 cm×1 cm) of the biomats were excised with a razor blade immediately before harvesting, and the excised portions were subjected to an ethanol washing/dehydration series by sequentially submersing the samples for the noted times in 40 mL of the ethanol mixtures as follows: 25% ethanol, 75% deionized H$_2$O for 20 minutes; 50% ethanol, 50% deionized H$_2$O for 20 minutes; 75% ethanol, 25% deionized H$_2$O for 20 minutes; 95% ethanol, 5% deionized H$_2$O for 20 minutes; 100% ethanol, 0% deionized H$_2$O for 60 minutes. The 100% ethanol treatment was repeated 2 more times before storing the samples in 100% ethanol.

To retain microstructure integrity of the biomats for FE-SEM, ethanol washing/dehydration was followed by critical point drying using a Tousimis Samdri-795 critical point dryer according to the manufacturer instructions (Tousimis Samdri-795 Operations Manual; Tousimis, Rockville, MD). After critical point drying, the samples were either mounted directly onto aluminum stubs or sliced into <0.3 mm thick sections with a razor blade prior to mounting. The samples were then coated with iridium (20 µm, EMITECH K575X, Electron Microscopy Sciences, Hatfield, PA) and examined with a JEOL 6100 FE-SEM using an incident beam energy of 1 keV (JEOL USA, Inc., Peabody, MA).

Figure 10:
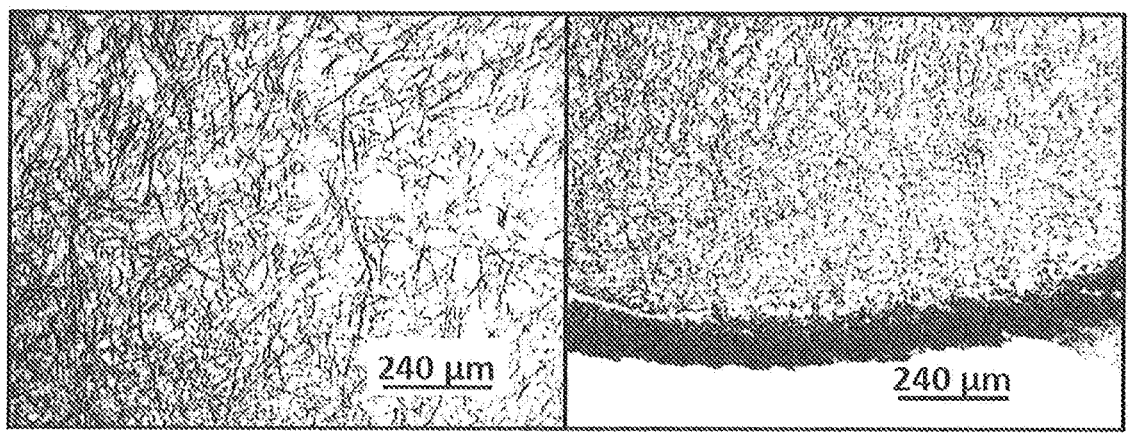
FIG. 10. Transmitted light microscope images (100×) of biomats grown on glycerol, starch and corn steep liquor. The image at the left of the aerial hyphal layer reveals the predominant near-vertical orientation of the filaments. The image at the right shows the dense bottom layer and the adjacent transitional layer.
Figure 11:
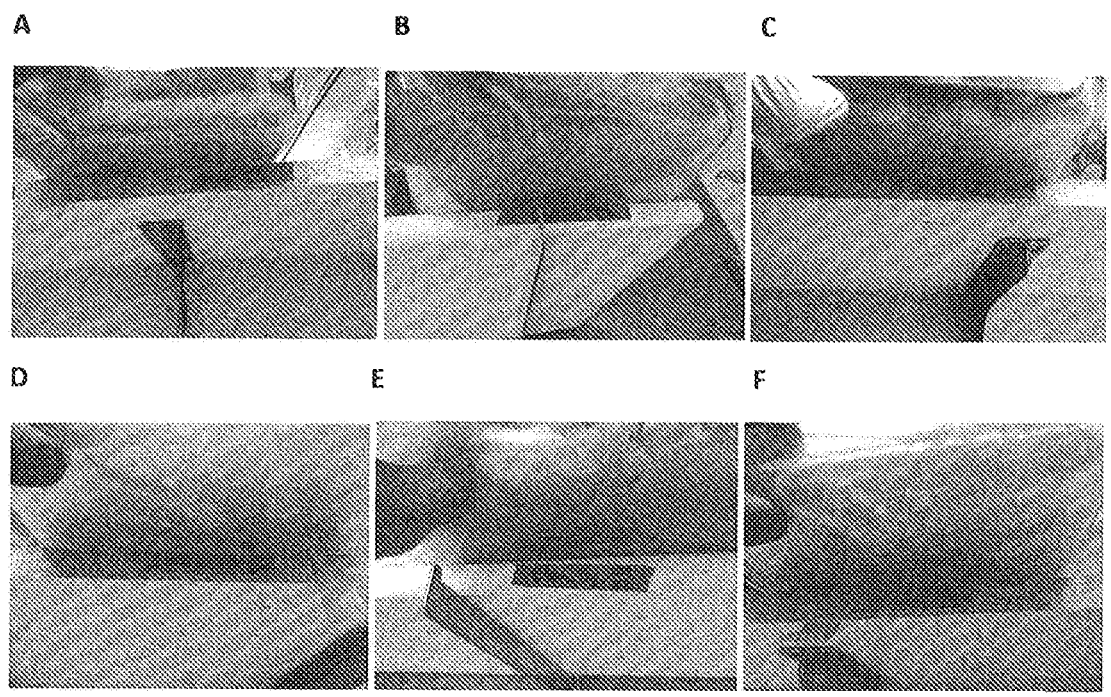
FIG. 11. Biomats produced using the disclosed method. A: Reishi mushroom; B: Pearl Oyster mushroom; C: Blue Oyster mushroom; D: Cauliflower mushroom; E: Elm oyster mushroom; F: Giant Puffball mushroom.

FE-SEM imaging revealed a complex network of interwoven hyphal filaments (FIG. 10), very similar to the structure revealed by light microscopy for biomats grown on glycerol as reported in PCT/US2017/020050. Three distinct layers were observed: (a) an aerial hyphae layer at the top surface, (b) a dense bottom layer and (c) a transitional layer between the top and bottom layers. The transitional layer was only loosely attached to the dense bottom layer, thus enabling easy separation of the bottom layer from the rest of the biomat. Filament densities of the transitional layer ranged from slightly less dense than the bottom layer in the zone where the two layers met, to a density that was comparable to the aerial hyphae near the top of the biomat.

Excised samples were also prepared for light microscopy by slowly dipping into the following solutions in the order and times shown below:

Xylene, 3 min; Xylene, 3 min; 100% ethanol, 3 min; 100% ethanol, 3 min; 95% ethanol, 3 min; 95% ethanol, 3 min; 70% ethanol, 3 min; Deionized water, 3 min; Hematoxylin 1, 1.5 min; Running tap water rinse, 1 min; Clarifier solution, 1 min; Running tap water rinse, 1 min; Bluing solution, 1 min; Running tap water rinse, 1 min; 70% ethanol, dips; 95% ethanol, 30 dips; 95% ethanol, 30 dips; 100% ethanol, 30 dips; 100% ethanol, dips; 100% ethanol, 30 dips; Xylene, 30 dips; Xylene, 30 dips; Xylene, 30 dips; Apply cover slip.

Sections of the biomats approximately 2 cm$^2$ in size were excised from the fresh biomats with a razor blade immediately before harvesting. These sections and then immersed in 35 mL of deionized water in 50 mL conical bottom centrifuge tubes. The tubes were sonicated (CP200T Ultrasonic Cleaner, Crest Ultrasonics, Ewing, NJ) for either 0, 40, or 150 seconds to disperse filaments into the liquid and enable microscopic observation. Aliquots of the liquid (~100 uL) from these tubes were placed on a glass slide, covered with a cover slip and observed with a light microscope (B400B, Amscope, Irvine, CA) at 100× magnification. The average length (std dev) of non-broken filaments were measured and determined to be 1.1 (0.6), 1.2 (0.4), 1.0 (0.4) and 1.2 (0.2) mm for the 0, 40, 90 and 160 second sonication treatments, respectively. The maximum filament length observed in each treatment were 2.5, 1.4, 1.8, and 1.4 mm, respectively. These filament lengths are significantly longer compared to growth of *Fusarium* strain MK7 in submerged shake flask cultures where average lengths are less than 0.02 mm.

Example 8: Production of Chicken Nuggets Using *Fusarium* Strain MK7 Biomats Grown on a Mixture of Glycerol, Starch and Corn Steep Liquor

*Fusarium* strain MK7 biomat, produced as described above, were used to create chicken nuggets. Moist biomats were steamed in a pot steamer at 97° C. for 0.5 hour, cooled to room temperature and used as the base to produce chicken nuggets. Steamed moist biomat (200 g) was chopped into pieces less than 0.5 mm long and homogenized with 4% (weight/weight; 8 g) chicken base and 4% egg white protein (8 g). The resulting mixture comprised more than 90% *Fusarium* strain MK7 biomat. Portions of this biomat mixture (~30 g) were formed into nugget shapes and steamed for in a pot steamer. The prepared nuggets were breaded by coating in egg whites and then mixing with bread crumbs that adhered to the surface prior to frying. The prepared nugget exhibited a chicken meat like texture and exuded the typical aroma of chicken. Taste testing by 5 people deemed the nugget to closely simulate actual chicken containing chicken nuggets in terms of taste and texture.

Example 9: Production of *Fusarium* Strain MK7 Biomat Extract

Highly concentrated and viscous extracts were produced from *Fusarium* strain MK7 biomats. Biomats harvested after 4-16 days of cultivation, as previously described, are rinsed and steamed, drip dried on porous plastic mesh for 5 minutes, and placed in plastic bags and sealed. Sealed bags are frozen at either −20° C. or −80° C. for 24 hours prior to being incubated at 60° C. incubator in the original sealed bags for 48 hours after pH adjustment of the remaining medium liquid to between pH 4-6. After heat treatment, biomats are pressed through <1.5 mm pore size filters and the resulting liquid collected. The collected liquid is boiled for 10 minutes in a non-reactive vessel then dried at 60° C. until water content is ~6-8%, forming a sticky paste extract. The nutritional value of the extract is similar to the nutritional value of the steamed biomat and flour made from steamed biomats.

Example 10. Production of Yogurt from *Fusarium* Strain MK7 Biomats Grown on Acid Whey

*Fusarium* strain MK7 biomats were used directly to produce yogurt. The biomats were grown in trays on an acid whey feedstock/carbon source that was generated as a byproduct of Greek yogurt manufacture, harvested after 6 days and were steamed within 20 minutes of harvesting. 200 g of the cooled, moist biomass was blended together with 600 g of drinking quality tap water to produce a milk-like suspension referred to as "MK7 liquid dispersion." The MK7 liquid dispersion was used as an ingredient by itself or in combination with cow's milk to produce yogurt.

Three mixtures containing different ratios of MK7 liquid dispersion to whole milk were prepared: 1) 25% MK7 liquid dispersion:75% whole milk, 2) 50% MK7 liquid dispersion: 50% whole milk, and 3) 100% MK7 liquid dispersion. The mixtures were used to make three batches of yogurt by heating each mixture to 83° C. and holding at that temperature for 14 minutes with constant stirring. The mixtures were allowed to cool to 43° C. and then live yogurt cultures added as inoculum. The resulting mixture was incubated at 44° C.

in a yogurt maker (Model YM80; EuroCuisine, Los Angeles, CA) for 8 hours. All of the resultant mixtures had the appearance and texture of yogurt, as well as a smell and taste similar to typical yogurt.

Example 11: Growth of Mushroom Biomats on Glycerol

Biomass biomats comprised of Baby Bella Brown Crimini Mushrooms (*Agaricus bisporus*) and White Mushrooms were produced in as little as 10 days using glycerol as the primary carbon source (feedstock). These common edible mushrooms were purchased from Albertson's supermarket in Bozeman, MT and stored at 4° C. The medium used to grow the mushrooms consisted of 1 L of 7.5% glycerol with MK7-1 salts (described in PCT/US2017/020050) that was boiled for 10 minutes followed by cooling to room temperature (~23° C.). The pH of the mixture was adjusted to 2.7 and 200 mL of the pH adjusted mixture was poured in two sterile 12.7×17.8 cm Pyrex® trays. The inoculum consisted of 5 g of blended, surface-sterilized Crimini or White Mushrooms that was added to the medium in each tray. The mushroom inoculum was prepared as follows: 1) 10 g of moist Crimini or White Mushrooms were added to 200 mL of a 5% bleach solution and the suspension was stirred for 2 minutes to surface sterilize the mushrooms, 2) the mushrooms were then rinsed by transferring into 200 mL of sterile glycerol/MK7-1 salts medium (described in PCT/US2017/020050) and stirring for 2 minutes, 3) the surface sterilized mushrooms were blended for 30 seconds in a coffee grinder that had been sterilized by rinsing with 70% ethanol, 4) the ground mushroom biomass (<5 mm long aggregates) was surface sterilized again by repeating steps 1 and 2 with the ground biomass, 5) 5 grams of the ground mushroom biomass was added to the liquid medium in the Pyrex® trays (final pH=4.0-4.1 after addition of mushrooms), and 6) the trays were covered and allowed to incubate at room temperature (22±2° C.) in the dark.

Biomats were observed to develop on the surface of the medium after 3 days of incubation and consolidated biomats were harvested after 10 days of growth. Biomats of Crimini Mushrooms covered the entire surface of the liquid medium in the tray while biomat growth of White Mushrooms covered approximately ½ the liquid medium as five floating biomat islands. The mean thickness of the biomats were 1.5 mm for the Crimini and 1.7 mm for the White Mushrooms. Biomass biomats were dried at 50° C. for 48 h and the dry weights produced per tray were 1.14 g and 2.12 g for the Crimini and White Mushrooms, respectively. Densities on a dry weight basis for the dry biomass biomats were 0.033 and g/cm$^3$ for the Crimini and White Mushrooms, respectively.

Microscope images revealed the mycelial nature of the biomats. Average hyphal thicknesses were 25.2 μm (std dev=6.2) and 18.7 μm (4.0) for the Crimini and White Mushroom biomats, respectively.

Produced Crimini biomats were used to create chicken nuggets. Biomats were steamed at 97° C. for 0.5 hour, cooled to room temperature and used as the base to produce chicken nuggets. Steamed moist biomass (2.5 g) was mixed with 3% (weight/weight; 75 mg) Better Than Bouillon chicken base (Southeastern Mills, Inc. Rome, GA) and 3% Eggwhite Protein (75 mg; Now Foods, Bloomingdale, IL) and chopped into pieces less than 2 mm long using a razor blade. The mixture was formed into a nugget and steamed for 0.5 hour. The prepared nugget provided the typical aroma of chicken with a slight mushroom fragrance. When tasted, the nugget had a chicken to neutral flavor.

Example 12. Growth of Mushroom Biomats on Malt and Glycerol Media

Biomass biomats comprised of *Calvatia gigantea* (giant puffball), *Pleurotus ostreatus* (pearl oyster), *Pleurotus ostreatus* var. *columbinus* (blue oyster), *Hypsizygus ulmarius* (elm oyster), *Sparassis crispa* (cauliflower) and *Ganoderma lucidum* (reishi) were produced in as little as 5 days using Malt Extract Medium 001, Glycerol Medium 002, Hansen's Medium, MK7-SF Medium, Malt Extract+ NH$_4$NO$_3$ Medium 003 (Table 3). All final media contained 0.01% chloramphenicol.

TABLE 3

Ingredients added to deionized or drinking quality tap water to prepare nutrient media.

| Malt Extract Medium 001 | | | | | |
| --- | --- | --- | --- | --- | --- |
| Ingredient | Amount | Grade | Lot # | Vendor | Location |
| Light Pilsner Malt | 40.0 g | Food | 180526B | Homebrewstuff.com | Boise, ID |
| Peptone | 4.0 g | Research | 44984-57374 | Research Products International | Mt Prospect, IL |
| Yeast Extract Powder | 1.2 g | Research | 53852-66581 | Research Products International | Mt Prospect, IL |
| Canola Oil | 1.0 mL | Food | SEP/25/19 CA S3283 | Better Living LLC | Pleasanton, CA |
| Ground Oats | 4.0 g | Food | Jan 25, 2020 I2M 06:36 | Walmart-Stores, Inc | Bentonville, AR |
| Tap H$_2$O | 1000 mL | N/A | N/A | N/a | Bozeman, MT |
| Glycerol Medium 002 | | | | | |
| Ingredient | Amount | Grade | Lot # | Vendor | Location |
| Glycerol | 40.0 g | Food/USP | 20149018137001 | Duda Energy LLC | Decatur, AL |
| Peptone | 4.0 g | Reagent | 44984-57374 | Research Products International | Mt. Prospect, IL |
| Yeast Extract | 1.2 g | Reagent | 53852-66581 | Research Products International | Mt. Prospect, IL |
| Canola Oil | 1.0 mL | Food | SEP/25/19 CA S3283 | Better Living LLC | Pleasanton, CA |

TABLE 3-continued

Ingredients added to deionized or drinking quality tap water to prepare nutrient media.

| Ingredient | Amount | Grade | Lot # | Vendor | Location |
|---|---|---|---|---|---|
| Ground Oats | 4.0 g | Food | Jan 25 2020 I2M 06:36 | Walmart-Stores, Inc | Bentonville, AR |
| Tap $H_2O$ | 1000 mL | N/A | N/A | N/a | Bozeman, MT |

Hansen's Medium

| Ingredient | Amount | Grade | Lot # | Vendor | Location |
|---|---|---|---|---|---|
| Peptone | 1.0 g | Reagent | 44984-57374 | Research Products International | Mt. Prospect, IL |
| $KH_2PO_4 * 7H_2O$ | 0.3 g | Reagent | Mfg. Doesn't use lot numbers | Eisen-Golden Laboratories | Dublin, CA |
| $MgSO_4 * 7H_2O$ | 2.0 g | USP | 81721 | San Francisco Salt Co. | San Leandro, CA |
| Glucose | 5.0 g | Reagent | 0435C235 | Fisher Scientific | Denver, CO |
| Tap $H_2O$ | 1000 mL | N/A | N/A | N/a | Bozeman, MT |

MK7-SF Medium

| Ingredient | Amount | Grade | Lot # | Vendor | Location |
|---|---|---|---|---|---|
| $NH_4NO_3$ | 7.553 g | ACS | A0390194 | Acros Organics | Somerville, NJ |
| Urea | 2.548 g | USP | 30570-67229 | Research Products International | Mt. Prospect, IL |
| $CaCl_2$ | 2.000 g | Reagent | 102615 | Fritz Pro Aquatics | Mesquite, TX |
| $MgSO_4 * 7H_2O$ | 2.000 g | USP | 81721 | San Francisco Salt Co. | San Leandro, CA |
| $KH_2PO_4$ | 7.500 g | Reagent | Mfg. Doesn't use lot numbers | Eisen-Golden Laboratories | Dublin, CA |
| Trace * | 2.000 mL | * | * | * | * |
| Glycerol | 0.075 Kg | Food/USP | 20149018137001 | Duda Energy LLC | Decatur, AL |
| Yeast Extract | 1.750 g | Research | 53852-66581 | Research Products International | Mt. Prospect, IL |
| $FeCL_2 * 4H_2O$ | 0.020 g | Reagent | 951164 | Fisher Scientific | Fair Lawn, NJ |
| DI $H_2O$ | 0.940 L | N/A | N/A | N/A | Bozeman, MT |

Trace Components *

| Micronutrients* | mg/L | Grade | Lot # | Vendor | Location |
|---|---|---|---|---|---|
| $FeSO_4 \cdot 7 H_2O$ | 9.98 | ACS | 3562C398 | Amresco | Solon, OH |
| $ZnSO_4 \cdot 7 H_2O$ | 4.4 | USP/FCC | 61641 | Fisher | Waltham, MA |
| $MnCl_2 \cdot 4 H_2O$ | 1.01 | Reagent | 13446-34-9 | Fisher | Waltham, MA |
| $CoCl_2 \cdot 6 H_2O$ | 0.32 | Reagent | 7791-13-1 | Fisher | Waltham, MA |
| $CuSO_4 \cdot 5 H_2O$ | 0.31 | Technical | 114675 | Fisher | Waltham, MA |
| $(NH_4)_6Mo_7O_{24} \cdot 4 H_2O$ | 0.22 | ACS | 68H0004 | Sigma | St. Louis, MO |
| $H_3BO_3$ | 0.23 | ACS | 103289 | Fisher | Waltham, MA |
| EDTA, free acid | 78.52 | Electrophoresis | 46187 | Fisher | Waltham, MA |

Malt Extract + $NH_4NO_3$ Medium 003

| Ingredient | Amount | Grade | Lot # | Vendor | Location |
|---|---|---|---|---|---|
| $NH_4NO_3$ | 5.0 g | ACS | A0390194 | Acros Organics | Somerville, NJ |
| Light Pilsner Malt | 40.0 g | Food | 180526B | Homebrewstuff.com | Boise, ID |
| Peptone | 4.0 g | Research | 44984-57374 | Research Products International | Mt. Prospect, IL |
| Yeast Extract Powder | 1.2 g | Research | 53852-66581 | Research Products International | Mt. Prospect, IL |
| Canola Oil | 1.0 mL | Food | SEP/25/19 CA S3283 | Better Living LLC | Pleasanton, CA |
| Ground Oats | 4.0 g | Food | Jan 25, 2020 I2M 06:36 | Walmart-Stores, Inc | Bentonville, AR |
| Tap $H_2O$ | 1000 mL | N/A | N/A | N/A | Bozeman, MT |

The above recipes in Table 3 were used to prepare media in either 2 L Pyrex® bottles or 8 L stainless steel pots by mixing the specified ingredients into the specific volumes of water depending on the volume of media desired. Ingredients were added to water while liquid was continuously stirred with a stir bar or a spoon. Each component of the media was thoroughly mixed into the liquid before the next component was added, pH for the MK7-SF medium was adjusted to 5.0, and the solutions autoclaved. All other pH's resulted from simply mixing the ingredients. The medium and vessels were autoclaved for at least 20 minutes at 20 psi and 121° C. Osmotic pressure (as osmolality) of the liquid was measured using an Advanced Instruments, Inc. osmometer Model 3250 (Two Technology Way, Norwood, MA).

After autoclaving, the media were allowed to cool to room to temperature and individual vessels were inoculated with the mushroom species shown in Table 4.

TABLE 4

Mushroom spores (10 cc syringes) were purchased from MycoDirect (12172 Route 47, Ste 199 Huntley, Il 60142) and received on Aug. 8, 2018. Elm Oyster spores were purchased from Everything Mushrooms (1004 Sevier Ave Knoxville, TN 37920) and received on Aug. 3, 2018.

|  | Lot | Date Produced by Company |
|---|---|---|
| Blue Oyster | 3-P7 | February 2018 |
| Pearl Oyster | 9P8 | December 2017 |
| Giant Puffball | N/A | March 2018 |
| Cauliflower Mushroom | N/A | April 2018 |
| Elm Oyster (1 cc dried) | N/A | October 2017 |

Inoculation of growth media was preformed using the following methods applied using aseptic technique. All aseptic work in these experiments were performed in Class II biosafety cabinet. Spore syringes were used to directly inoculate approximately 75 mL of growth medium in previously autoclaved, 12.7×17.8 cm Pyrex® glass trays. This was done by aseptically transferring liquid medium into an autoclaved Pyrex® tray, allowing the media to cool to room temperature and inoculating with 2 cc of the suspension contained in the spore syringe. The tray was covered with sterile aluminum foil and then gently swirled to mix the inoculated medium.

Malt Extract Agar (MEA; Table 5) plates were prepared aseptically by autoclaving MEA, allowing to cool to 50° C., and pouring ~25 mL into 100×15 mm sterile Petri dishes.

MEA plates were inoculated by aliquoting 1 cc of liquid from the suspension contained within the spore syringe onto the plates. The agar plates were then sealed with Parafilm® and placed into a clean dark drawer at room temperature.

After mycelium had covered the entire surface of the MEA plates, they were used for inoculation of 1.5 L medium in 2 L baffled shaker flasks. Approximately 2 $cm^2$ portions of agar medium with mycelium on the surface were excised from the plates with a sterile razor blade and diced into ~2 $mm^2$ portions, which were then added to two flasks containing 1.5 L of Malt Extract 001 medium. The medium was incubated for 3 days at room temperature (23±1° C.) with intermittent shaking by hand (flasks were vigorously shaken by hand for 1 minute at a minimum of five times per day).

The cultures in the shaker flasks were then used as inoculum for 6 L of Malt Extract medium 001 and for 6 L of Malt Extract+$NH_4NO_3$ 003 medium. The media were inoculated with 15% (vol:vol) of inoculum culture and mixed thoroughly. Two liters of inoculated media were poured into each of three 0.25 $m^2$ plastic trays that were placed into a tray rack. The racks were wrapped in Saran® and allowed to incubate for 6 days. Relatively dense biomats covering the entire surface within 4 days and the biomats were harvested after 6 days.

Biomats from 12.7×17.8 cm Pyrex® glass trays and the 0.25 $m^2$ plastic trays were harvested by lifting the biomats from the trays and gently squeezing by hand. Portions of the biomats (3-50 g) were streamed for 20 minutes over boiling water (~5 cm above surface of water) in a pot steamer set on a kitchen oven burner. After steaming, the biomass was allowed to cool to room temperature and immediately bagged in a Ziploc® bag and sent to Eurofins (Des Moines, IA) for protein analysis (N by combustion, Test Code QD252).

TABLE 5

Ingredients used to prepare Malt Extract Agar
Malt Extract Media (MEA)

| Ingredient | Amount | Grade | Lot # | Vendor | Location |
|---|---|---|---|---|---|
| Light Pilsner Malt | 30.0 g | Food | 180526B | Homebrewstuff.com | Boise, ID |
| Agar | 20.0 g | Microbiological | 2170501 | BD | Sparks, MD |
| Tap $H_2O$ | 1000 mL | N/A | N/A | N/A | Bozeman, MT |

TABLE 6

Results from a series of different filamentous fungi growth in trays in various types of media

| Media | Tray Size (m²) | Initial Medium pH | C:N | Ionic Strength (mmol/L) | Osmotic Pressure (mOsm/kg) | Time (days) | Final pH Free Liquid | Biomass per Surface Area (g/m²) | Density (g/cm³) | Wet Biomat Tensile Strength (g/cm³) |
|---|---|---|---|---|---|---|---|---|---|---|
| Giant Puffball | | | | | | | | | | |
| Malt 001 | 0.022 | 6.28 | 19 | 33.1 | 169 | 5.7 | 5.62 | 71.4 | 0.057 | 314.1 |
| Glycerol 002 | 0.022 | 6.96 | 30 | 13.6 | 505 | 5.7 | 5.54 | 40 | 0.04 | 214.9 |
| Hansen's | 0.022 | 8.81 | 27 | 30.7 | 39 | n/a | n/a | n/a | n/a | n/a |
| MK7-SF | 0.022 | 4.91 | 7.5 | 344 | 1387 | 9.0 | 5.07 | 178.6 | 0.045 | 135.0 |
| Malt 001 | 0.25 | 6.96 | 19 | 33.1 | 169 | 6.2 | 6.25 | 111.1 | 0.037 | 264.0 |
| Malt + NH$_4$NO$_3$ 003 | 0.25 | 6.88 | 7.5 | 145.1 | 287 | 5.8 | n/a | 108.3 | 0.11 | 281.1 |
| Cauliflower | | | | | | | | | | |
| Malt 001 | 0.022 | 6.28 | 19 | 33.1 | 169 | 6.7 | 4.44 | 146.7 | 0.073 | 507.83 |
| Glycerol 002 | 0.022 | 6.96 | 30 | 13.6 | 505 | 6.7 | 5.77 | 24.2 | 0.012 | 242.91 |
| Hansen's | 0.022 | 8.81 | 27 | 30.7 | 39 | N/A | N/A | N/A | N/A | N/A |
| MK7-SF | 0.022 | 4.91 | 7.5 | 344 | 1387 | N/A | N/A | N/A | N/A | N/A |
| Malt 001 | 0.25 | 6.96 | 19 | 33.1 | 169 | N/A | N/A | N/A | N/A | N/A |
| Malt + NH4NO3 | 0.24 | 6.88 | 7.5 | 145.1 | 287 | N/A | N/A | N/A | N/A | N/A |
| Blue | | | | | | | | | | |
| Malt 001 | 0.022 | 6.28 | 19 | 33.1 | 169 | 10 | 5.7 | 112.5 | 0.023 | 72.34 |
| Glycerol 002 | 0.022 | 6.96 | 30 | 13.6 | 505 | 10 | 5.56 | 56.1 | 0.014 | 37.37 |
| Hansen's | 0.022 | 8.81 | 27 | 30.7 | 39 | N/A | N/A | N/A | N/A | N/A |
| MK7-SF | 0.022 | 4.91 | 7.5 | 344 | 1387 | N/A | N/A | N/A | N/A | N/A |
| Malt 001 | 0.25 | 6.96 | 19 | 33.1 | 169 | N/A | N/A | N/A | N/A | N/A |
| Malt + NH4NO3 | 0.24 | 6.88 | 7.5 | 145.1 | 287 | 5.8 | N/A | N/A | N/A | N/A |
| Pearl | | | | | | | | | | |
| Malt 001 | 0.022 | 6.28 | 19 | 33.1 | 169 | 10 | 5.47 | 124.4 | 0.025 | 98.97 |
| Glycerol 002 | 0.022 | 6.96 | 30 | 13.6 | 505 | N/A | N/A | N/A | N/A | N/A |
| Hansen's | 0.022 | 8.81 | 27 | 30.7 | 39 | N/A | N/A | N/A | N/A | N/A |
| MK7-SF | 0.022 | 4.91 | 7.5 | 344 | 1387 | N/A | N/A | N/A | N/A | N/A |
| Malt 001 | 0.25 | 6.96 | 19 | 33.1 | 169 | N/A | N/A | N/A | N/A | N/A |
| Malt + NH4NO3 | 0.24 | 6.88 | 7.5 | 145.1 | 287 | 5.8 | N/A | N/A | N/A | N/A |
| Elm | | | | | | | | | | |
| Malt 001 | 0.022 | 6.28 | 19 | 33.1 | 169 | 10 | 5.21 | 111.6 | 0.032 | 143.67 |
| Glycerol 002 | 0.022 | 6.96 | 30 | 13.6 | 505 | N/A | N/A | N/A | N/A | N/A |
| Hansen's | 0.022 | 8.81 | 27 | 30.7 | 39 | N/A | N/A | N/A | N/A | N/A |
| MK7-SF | 0.022 | 4.91 | 7.5 | 344 | 1387 | N/A | N/A | N/A | N/A | N/A |
| Reishi | | | | | | | | | | |
| Malt 001 | 0.022 | 6.28 | 19 | 33.1 | 169 | 6.7 | 4.59 | 0.006 | 0.13 | 101.05 |
| Glycerol 002 | 0.022 | 6.96 | 30 | 13.6 | 505 | 6.7 | 4.54 | N/A | N/A | N/A |
| Hansen's | 0.022 | 8.81 | 27 | 30.7 | 39 | N/A | N/A | N/A | N/A | N/A |
| MK7-SF | 0.022 | 4.91 | 7.5 | 344 | 1387 | N/A | N/A | N/A | N/A | N/A |

Example 13. *Fusarium* Strain MK7 Chicken Nugget

Chicken flavored *Fusarium* strain MK7 is a basic ingredient to a number of recipes including chicken nuggets, with or without breading, chicken for Asian dishes, or other chicken dishes as a chicken replacement. *Fusarium* strain MK7 biomats produced from different feedstocks/carbon sources result in slightly different chicken flavors. The glycerol chicken is sweeter and the acid whey chicken tends to be a little bit sourer.

The amount of food processing and the blade used (i.e. sharp metal blade, dull metal blade, plastic blade) result in different chicken nugget textures. Further, acceptable chicken nuggets can be produced from a wide variety of biomass sizes. That is, biomass can be cut with a knife, lightly food processed or highly food processed and still result in acceptable chicken analogs.

A 50-20:1:1 ratio of *Fusarium* strain MK7:chicken stock: binder was used with or without approximately a 66.6% *Fusarium* strain MK7:fat ratio. Suitable fats include duck fat, coconut butter, and cocoa butter. After mixing, the mixture is steamed for approximately minutes to set the binder; however, some binders may require more or less time. Additional breading can then be added and the resulting nuggets process as typical for such foodstuffs.

Example 14: Breakfast Sausage and/or Hot Dog and/or Burger

An appropriate spice mix is added to size reduced *Fusarium* strain MK7 biomats as needed to develop the flavors desired, which may be between 10 wt. % of spice mix to a quantity of *Fusarium* strain MK7 up to 20%, oftentimes in a ratio of 10 *Fusarium* strain MK7:1 spice mix, with or without additional ingredients such as onion, binders, and a fat such as cocoa butter. The mixture is then fried to remove an appropriate amount of moisture. Additional ingredients can then be added, such as bulgur, vegetable broth, potatoes, etc. prior to shaping in the desired shape and cooking.

Example 15: Ice Cream and Mousse

A ratio of approximately 1:3 *Fusarium* strain MK7 biomat:water is generated having a particle size with average filament lengths less than 900 microns. This mixture is gently heated until there is no longer a fungal scent and then used in approximately a 4:1 ratio with cashews, optionally with an appropriate amount of xanthan gum and/or flavoring, to generate a mix which may be optionally heated and then cooled to form a mousse. For frozen dessert, the mix is then placed in an ice cream churner and, after churning, frozen to form a non-meltable frozen dessert.

Example 16: Production of Truffle Oil from Truffle Biomats

Oil extract can be prepared from Truffle (*Tuber* sp.) biomats grown as described above. In one instance, truffle biomats were grown in trays in as little as 7 days using malt extract, glucose and peptone as the primary carbon sources (feedstock). The edible Truffle mushroom was purchased from IGB Trading LLC on the Amazon Marketplace and stored at 4° C. A pure culture of the *Tuber* sp. fungus was prepared from the purchased truffle by placing ~3 mm 3 portions of truffle (cut with a sterile razor blade) on Malt Extract Agar+chloramphenicol (used to inhibit bacterial growth). A Malt Extract Agar was prepared by mixing 20 g of malt extract, 20 g of glucose, 1 g peptone and 20 g of agar in 1 L of deionized water prior to autoclaving for 30 minutes and cooling to 50° C. before adding chloramphenicol. The sterile mixture was then poured into 9 cm diameter Petri plates and allowed to cool and solidify.

The fungus was observed to grow on the trays after 3 days. After 4 days of growth, hyphae were picked with a sterile microbiological loop and streaked onto a fresh set of Malt Extract Agar+chloramphenicol plates. The fungus was allowed to grow on said plates for days, after which hyphae were picked with a microbiological loop and used to confirm culture purity by DNA sequencing. Confirmation was accomplished by extracting and purifying the DNA (FastDNA Spin Kit, MP Biomedicals) and sequencing the ITS region of the metagenome followed by phylogenetic classification of the sequences using Blast (NCBI database).

Malt Extract Broth was prepared by mixing 20 g of malt extract, 20 g of glucose and 1 g peptone in 1 L of deionized water and sterilized. Scrapes of the hyphae with the microbiological loop were also used to inoculate 50 mL of sterile Malt Extract Broth in sterile baffled shaker flasks capped with sterile gauze material. Sterile gauze was used as it allowed exchange of gases into and out of the shaker flask. Shaker flasks were then rotated at 185 rpm for 5 days. The rotated cultures were then used to inoculate 350 mL of sterile Malt Extract Broth in sterile 12.7×17.8 cm Pyrex® glass trays. The inoculum density was for this culture medium was 7.5% inoculum to 92.5% broth. After 7 days of growth in the trays, the filamentous biomat formed on the surface was harvested by lifting the biomat from the liquid medium. The harvested biomats were dried at 40° C. for 48 h. Lipids/oil from these harvested biomats were extracted by either mechanical pressing or by solvent extraction using hexane, although other extraction methodologies can be used.

Example 17: MK7 Flour

*Fusarium* strain MK7 biomat, produced as described above, was used to create dried powder similar in particle size and particle size distribution to a standard baking flour. Here, moist biomats were steamed in a pot steamer at 97° C. for 0.5 hour, cooled to room temperature and dehydrated in a Cuisinart dehydrator (model DHR-20) for 2-8 hours with an average dehydration time being 4 hours. Dehydration time is a function of the amount of biomass loaded into the dehydrator, distribution of biomats in the dehydrator which impacts air flow in the dehydrator and the water content of biomats (average water content approximately 75%) and room temperature. Water content post dehydration varies between 4 and 14% with average water content post dehydration being below 12%. Dehydrated biomass was size reduced using a coffee grinder (KRUPS, Electric coffee and spice grinder, stainless steel blades F2034251) until finely ground. Average particle size for ground biomat flour ranged from 75 microns to 120 microns. A small fraction of larger particles, app 5 wt %, had a particle size of greater than 180 microns. A small fraction of smaller particles, app. 5 wt % had a particle size smaller than 75 microns. Said smaller particles were of a size which enabled the small particles to remain air borne for extended periods of time. Particle size was determined by sifting 100 gram samples of size reduced biomats for 5 minutes in sieves with 180 μm, 120 μm and 75 μm openings. Water content post dehydration and post size reduction below 6% is preferred as higher water contents can lead to clumping of dried and milled biomass.

Biomat flour was then used as an addition to other standard flours (King Arthur flour, Bob's Red Mill Flour & Bob's Red Mill Wheat Flour) and a variety of baked goods where prepared. Biomat flour was loaded at 5 wt %, 10 wt %, 20 wt % and 30 wt % with no deleterious effect on ultimate baked good taste, rising, texture, appearance or smell. Products demonstrated included bread (7 grain, white & wheat), pastries (Pate a Choux), cookies, pasta and dumplings. The resulting products performed well in taste tests and the inclusion of strain MK7 flour was not detectable to those tasting the products.

Example 18: MK7 Extender

*Fusarium* strain MK7 biomat, produced as described above, was used to create particles of biomass that were used as an addition to meat and fish as an extender (i.e. increase the amount of total food product by the addition of strain MK7 to other exiting foodstuffs). Moist biomats were steamed in a pot steamer at 97° C. for 0.5 hour, cooled to room temperature. Biomats where size reduced (i.e. chopping with a knife or food processing in a food processor) to a desirable particle size distribution. Size reduced biomass was then added to different food products to extend the amount of meat in the case of a meat extender or fish in the case of a fish extender. As an example of meat extension. 10%, 20%, 30%, 40% and 50% additions of size reduced biomass were added to hamburger meat. Size reduction of biomass was evaluated at a number of different size distributions. Smaller particle sizes tended to produce denser and creamier textures. Larger particles tended to produce products with more texture, more mouth feel and required more mastication before swallowing. The extended meat was them processed as though no biomass was added. In the case of hamburger extension, spices or binders can be optionally added and the extended meat was formed into a patty or meat ball and cooked until the meat was cooked to the consumer desired temperature. Cooking methods included stove top, oven, frying and grill. Taste tests showed that acceptable food products where produced at all loading levels and all size distributions of added biomass. Chicken and pork extensions where also tried at similar loading levels with similar cooking and tasting results.

Fish extension was also demonstrated at 10%, 20%, 30% and 40% loadings. Fish fillet and fish balls where produced by adding processed strain MK7 at a variety of different size distributions ranging from small particles (less than 1.0 mm) to large particles (greater than 2 mm) with no deleterious effect on taste, color, smell or over all eating experience. In the case of small particle size additions, resulting foodstuffs had a creamier texture. In the case of large particle size additions, resulting foodstuffs had a firmer texture characterized by larger particles which required more mastication before swallowing. Taste tests showed that acceptable food products where produced at all tested loading and size distribution levels.

Example 19: MK7 Jerky

*Fusarium* strain MK7 biomat, produced as described above, was used to create mycojerky, similar in appearance and taste to meat jerkies (i.e. beef jerky, buffalo jerky, pork jerky, chicken jerky, turkey jerky, etc.). Moist biomats were steamed in a pot steamer at 97° C. for 0.5 hour, cooled to room temperature. Biomats where size reduced to a size consistent with that normally found in jerky products. Size reduced biomat pieces where in some cases seasoned for flavor and dehydrated in a Cuisinart dehydrator (model DHR-20) for 20-200 minutes with an average dehydration time being 40-120 minutes. Dehydration time is a function of the amount of biomass loaded into the dehydrator, distribution of biomats in the dehydrator which impacts air flow in the dehydrator, water content of biomats (average water content approximately 75%), room temperature and desired water content in the final product. Water content post dehydration varied between 8% and 12% depending on desired product characteristics. In some cases, perforating the biomass before dehydration produced a product that tore more readily into small pieces thereby easing consumption. Perforation of the biomass was performed by using a fork, knife or tenderizer tool which both perforated the biomass as well as disrupted the filament network such that it tore more easily. A large variety of spice mixtures (i.e. Cajun, cheese, soy, vinegar, herbs, sour cream & onion, liquid smoke, vegan meat flavors, etc.) where evaluated. Spice mixtures were evaluated both before dehydration and post dehydration. Those samples which were spiced before dehydration offered more taste and better adhered to the biomass than those which were treated after dehydration. The resulting jerkies all performed well in taste tests.

Example 20: Myco-Chips

*Fusarium* strain MK7 biomat, produced as described above, were used to chips, similar in appearance and taste to potato chips or corn chips. Moist biomats were steamed in a pot steamer at 97° C. for 0.5 hour, cooled to room temperature. Biomats where size reduced to a size consistent with that normally found in chip products as well as highly processed into a paste and formed into a chip like geometry. Myco-chips where then put into a frying pan of hot oil (temperature app equal to 380° F.) until brown. Cooking times varied as a function of biomass geometry but cooked very fast, usually in under 15 seconds. Produced fried chips proved to be very palatable and capable of offering a wide variety of taste experiences dependent upon spices added to or coated upon the biomass pre-frying.

TABLE 8

Nutritional data from *Pleurotus eryngii*

| | |
|---|---|
| Species name | *Pleurotus eryngii* |
| Common name | King Oyster Mushroom |
| Strain and source | Blue-Mycodirect |
| Mr. DNA results | Positive ID |
| Harvest Date | Aug. 6, 2018 |
| Media | Malt 001 |
| mmol/L | 33.1 |
| Osmolality (mOsm) | 169 |
| C:N Ratio | 19 |
| Protein | 19.38% |

TABLE 9

Nutritional data from *Sparassis crispa*

| | *Sparassis crispa* | *Sparassis crispa* | *Sparassis crispa* | *Sparassis crispa* |
|---|---|---|---|---|
| Species name | | | | |
| Common name | Cauliflower Mushroom | Cauliflower Mushroom | Cauliflower Mushroom | Cauliflower Mushroom |
| Strain and source | Amazon | Mycodirect | Mycodirect | Mycodirect |
| Mr. DNA results | | Positive ID | Positive ID | Positive ID |
| Harvest Date | Fruiting Body | Jan. 22, 2019 | Jan. 22, 2019 | Jan. 22, 2019 |
| Time (d) | | 8 | 8 | 8 |
| Tray m2 | | 0.022 | 0.022 | 0.022 |
| Initl pH | | 6 | 6 | 6 |
| End pH | | 4.89 | 5.47 | 4.44 |
| Yield (g/m2) | | 156.7 | 90.67 | 149 |
| Density (g/cm3) | | 0.0156 | 0.0121 | 0.011 |
| Tensile Strength (g/cm2) | | 1960.03 | 242.91 | 1243.06 |
| Media | | Malt 001 | Glycerol 002 | Malt 003 |
| mmol/L | | 33.1 | 13.6 | 145.1 |
| Osmolality (mOsm) | | 169 | 505 | 287 |
| C:N Ratio | | 19 | 30 | 7.5 |
| Protein | 13.37% | 35.71% | 32.21% | 46.24% |
| Ash | 6.54% | 3.61% | 3.99% | 3.47% |
| Carbohydrates | 78.44% | 51.16% | 48.16% | 37.57% |
| Fat by AH | Pending | 9.52% | 15.60% | 2.20% |
| Total Fat as Triglycerides | 1.65% | | | |
| Total Saturated Fatty Acids | 0.36% | | | |

TABLE 11

Nutritional data from *Morchella esculenta*

| Species name | *Morchella esculenta* | *Morchella esculenta* | *Morchella esculenta* |
|---|---|---|---|
| Common name | Yellow Morel | Yellow Morel | Yellow Morel |
| Strain and source | Amazon | Mycodirect | Mycodirect |
| Mr. DNA result | | Positive ID | Positive ID |
| Harvest Date | Fruiting Body | Dec. 28, 2018 | Feb. 5, 2018 |
| Time (d) | | 10 | 14 |
| Tray m2 | | 0.022 | 0.075 |
| Initl pH | | 6 | 6 |
| End pH | | 5.7 | 4.8 |
| Yield (g/m2) | | 243.85 | 218.85 |
| Density (g/cm3) | | 0.083 | 0.0331 |
| Tensile Strength (g/cm2) | | | 387.04 |
| Media | | Malt 001 | Malt 001 |
| mmol/L | | 33.1 | 33.1 |
| Osmolality (mOsm) | | 169 | 169 |
| C:N Ratio | | 19 | 19 |
| Protein | 30.37% | 16.62% | 26.29% |
| Ash | 6.98% | Below detection | 1.85% |
| Carbohydrates | 60.90% | Not tested | 64.47% |
| Fat by AH | 2.78% | Not tested | 14.07% |
| Total Fat as Triglycerides | 1.76% | Not tested | 7.68% |
| Total Fatty Acids | 1.67% | Not tested | 7.05% |
| Total Saturated Fatty Acids | 0.41% | Not tested | 1.32% |

TABLE 12

Nutritional data from *Calvatia gigantea*

| Species name | "*Calvatia gigantea*" | "*Calvatia gigantea*" | "*Calvatia gigantea*" | "*Calvatia gigantea*" |
|---|---|---|---|---|
| Common name | Giant Puffball | Giant Puffball | Giant Puffball | Giant Puffball |
| Strain and source | Mycodirect | Mycodirect | Mycodirect | Mycodirect |
| Mr. DNA result | *C. rosae* | *C. rosae* | *C. rosae* | *C. rosae* |
| Harvest Date | Aug. 9, 2018 | Aug. 20, 2018 | Aug. 23, 2018 | Aug. 23, 2018 |
| Time (d) | 5.7 | 6.2 | 9 | 5.8 |
| Tray m2 | 0.022 | 0.25 | 0.022 | 0.25 |
| Initl pH | 6.5 | 6.5 | 6.5 | 6.5 |
| End pH | 5.62 | 6.25 | 5.07 | Not recorded |
| Yield (g/m2) | 71.42 | 111.1 | 178.6 | 108.3 |
| Density (g/cm3) | 0.07 | 0.037 | 0.045 | 0.11 |
| Tensile Strength (g/cm2) | 314.1 | 264 | 135 | 281.1 |
| Media | Malt 001 | Malt 001 | MK7-SF | Malt 003 |
| mmol/L | 33.1 | 33.1 | 334 | 145.1 |
| Osmolality (mOsm) | 169 | 169 | 1387 | 287 |
| C:N Ratio | 19 | 19 | 7.5 | 7.5 |
| Protein | 32.03% | 34.89% | 46.32% | 46.90% |
| Ash | Not tested | 3.69% | 7.81% | 3.66% |
| Carbohydrates | Not tested | 53.16% | Not tested | Not tested |
| Fat by AH | Not tested | Below detection | Not tested | Not tested |
| Total Fat as Triglycerides | Not tested | 8.27% | Not tested | Not tested |
| Total Fatty Acids | Not tested | 7.91% | Not tested | Not tested |
| Total Saturated Fatty Acids | Not tested | 1.66% | Not tested | Not tested |

TABLE 13

Nutritional data from *Calvatia gigantea*

| Species name | "*Calvatia gigantea*" | "*Calvatia gigantea*" | "*Calvatia gigantea*" | "*Calvatia gigantea*" | "*Calvatia gigantea*" |
|---|---|---|---|---|---|
| Common name | Giant Puffball | Giant Puffball | Giant Puffball | Giant Puffball | Giant Puffball |
| Strain and source | Outgrow | Outgrow | Outgrow | Outgrow | Outgrow |
| Mr. DNA result | *C. rosae* | *C. rosae* | *C. rosae* | *C. rosae* | *C. rosae* |
| Harvest Date | Feb. 11, 2019 | Feb. 11, 2019 | Feb. 11, 2019 | Feb. 11, 2019 | Feb. 11, 2019 |
| Time (d) | 6 | 6 | 6 | 6 | 6 |
| Tray m2 | 0.022 | 0.022 | 0.022 | 0.022 | 0.022 |
| Initl pH | 6 | 6 | 6 | 6 | 6 |
| End pH | 6.25 | 4.45 | 2.74 | 2.87 | 3.1 |
| Yield (g/m2) | 144.76 | 38.41 | 197.12 | 170.66 | 179.66 |
| Density (g/cm3) | 0.21 | 0.08 | 0.2 | 0.17 | 0.36 |
| Tensile Strength (g/cm2) | 562.96 | 1259.26 | 1559.23 | 833.33 | 1040 |
| Media | MK7-102 5% Glyc | MK7-102 5% Glyc | MK7-102 5% Glyc | MK7-102 5% Glyc | MK7-102 5% Glyc |
| C:N Ratio | 5 | 7.5 | 15 | 30 | 40 |
| Protein | 45.95% | 49.26% | 38.15% | 20.61% | 24.30% |
| Ash | 4.65% | 4.76% | 6.20% | 3.74% | 4.61% |
| Carbohydrates | 45.77% | 38.90% | 53.65% | 70.19% | 66.78% |
| cis, cis-Poly unsaturated FA | 2.05% | 2.76% | 1.00% | 1.07% | 0.83% |
| Cis-Monounsaturated FA | 0.51% | 0.61% | 0.35% | 1.26% | 0.73% |
| Total Saturated Fatty Acids | 0.93% | 1.10% | 0.40% | 0.92% | 0.67% |
| Total Fat as Triglycerides | 3.63% | 4.70% | 2.00% | 3.40% | 2.33% |
| Total Trans FA isomers- GC | Below Detection | Below Detection | Below Detection | Below Detection | Below Detection |

TABLE 14

Nutritional data from *Fusarium venenatum*

| | |
|---|---|
| Species name | *Fusarium Venenatum* |
| Strain and source | ATCC |
| Mr. DNA result | Positive ID |
| Romer Labs Toxicity | Passed |
| Harvest Date | Jan. 16, 2019 |
| Time (d) | 5 |
| Tray m2 | 0.25 |
| Initl pH | 4.5 |
| Yield (g/m2) | 66 |
| Density (g/cm3) | 0.85 |
| Tensile Strength (g/cm2) | 866.2 |
| Media | MK7-102 10% Glycerol |
| C:N Ratio | 7.5 |
| Protein | 41.56% |
| Ash | 6.14% |
| Carbohydrates | 44.89% |
| Total Fat as Triglycerides | 7.43% |
| Total Fatty Acids | Below detection |
| Total Saturated Fatty Acids | 2.29% |

TABLE 15

Nutritional data from *Fusarium Venenatum*

| Species name | *Fusarium Venenatum* | *Fusarium Venenatum* | *Fusarium Venenatum* | *Fusarium Venenatum* | *Fusarium Venenatum* |
|---|---|---|---|---|---|
| Common name | | | | | |
| Strain and source | ATCC | ATCC | ATCC | ATCC | ATCC |
| Mr. DNA result | Positive ID | Positive ID | Positive ID | Positive ID | *C. Rosea* |
| Harvest Date | Feb. 11, 2019 | Feb. 11, 2019 | Feb. 11, 2019 | Feb. 11, 2019 | Feb. 11, 2019 |
| Time (d) | 6 | 6 | 6 | 6 | 6 |
| Tray m2 | 0.022 | 0.022 | 0.022 | 0.022 | 0.022 |
| Initl pH | 4.5 | 4.5 | 4.5 | 4.5 | 4.5 |
| End pH | 6.15 | 4.81 | 3.49 | 3.29 | 2.97 |
| Yield (g/m2) | 71.43 | 89.06 | 63.81 | 76.03 | 215.95 |
| Density (g/cm3) | 0.14 | 0.09 | 0.16 | 0.06 | 0.43 |
| Tensile Strength (g/cm2) | 186.67 | 166.67 | 800 | 370.37 | 3151.52 |
| Media | MK7-102 5% Glycerol | MK7-102 5% Glycerol | MK7-102 5% Glycerol | MK7-102 5% Glycerol | MK7-102 5% Glycerol |
| C:N Ratio | 5 | 7.5 | 15 | 30 | 40 |
| Protein | 44.11% | 43.14% | 45.25% | 48.11% | 28.13% |
| Ash | 5.00% | 5.20% | 4.43% | 5.22% | 5.31% |
| Carbohydrates | 44.95% | 44.77% | 42.70% | 42.25% | 64.16% |
| cis, cis-Poly unsaturated FA | 2.36% | 2.23% | 2.80% | 3.04% | 1.05% |
| Cis-Monounsaturated FA | 1.26% | 0.48% | 0.80% | 0.68% | 0.57% |
| Total Saturated Fatty Acids | 2.05% | 1.00% | 1.42% | 1.28% | 0.67% |
| Total Fat as Triglycerides | 5.95% | 3.89% | 5.26% | 5.24% | 2.39% |
| Total Trans FA isomers-GC | Below Detection | Below Detection | Below Detection | Below Detection | Below Detection |

TABLE 16

Nutritional data from *Fusarium* strain MK7

| Species name | *Fusarium* | *Fusarium* | *Fusarium* | *Fusarium* | *Fusarium* |
|---|---|---|---|---|---|
| Common name | MK-7 | MK-7 | MK-7 | MK-7 | MK-7 |
| Strain and source | MK-7 Stock Culture | MK-7 Stock Culture | MK-7 Stock Culture | MK-7 Stock Culture | MK-7 Stock Culture |
| Mr. DNA result | Positive ID | Positive ID | Positive ID | Positive ID | Positive ID |
| Harvest Date | Feb. 11, 2019 | Feb. 11, 2019 | Feb. 11, 2019 | Feb. 11, 2019 | Feb. 11, 2019 |
| Time (d) | 6 | 6 | 6 | 6 | 6 |
| Tray m2 | 0.022 | 0.022 | 0.022 | 0.022 | 0.022 |
| Initl pH | 3.3 | 3.3 | 3.3 | 3.3 | 3.3 |
| End pH | 6.2 | 7.2 | 4.91 | 2.36 | 3.3 |
| Yield (g/m2) | 483.33 | 314.62 | 92.31 | 103.64 | 156.09 |
| Density (g/cm3) | 0.48 | 0.31 | 0.07 | 0.1 | 0.05 |
| Tensile Strength (g/cm2) | 333.33 | 1454.55 | 191.11 | 426.67 | 312.12 |
| Media | MK7-102 5% Glycerol | MK7-102 5% Glycerol | MK7-102 5% Glycerol | MK7-102 5% Glycerol | MK7-102 5% Glycerol |
| C:N Ratio | 5 | 7.5 | 15 | 30 | 40 |
| Protein | 53.09% | 38.71% | 46.67% | 35.31% | 40.74% |
| Ash | 8.92% | 7.67% | 8.20% | 10.00% | 10.66% |
| Carbohydrates | 33.52% | 50.74% | 41.60% | 51.98% | 44.95% |
| cis, cis-Poly unsaturated FA | 2.59% | 1.60% | 2.13% | 1.23% | 2.14% |
| Cis-Monounsaturated FA | 0.58% | 0.43% | 0.40% | 0.12% | 0.44% |
| Total Saturated Fatty Acids | 0.94% | 0.74% | 0.80% | 0.68% | 0.89% |
| Total Fat as Triglycerides | 4.24% | 2.89% | 3.53% | 2.35% | 3.63% |
| Total Trans FA isomers-GC | Below Detection | Below Detection | Below Detection | Below Detection | Below Detection |

TABLE 17

Nutritional data from *Lenitnula edodes*

| | |
|---|---|
| Species name | *Lenitnula edodes* |
| Common name | Shiitake Mushroom |
| Strain and source | Safeway |
| Harvest Date | Fruiting Body |
| Protein | 15.73% |
| Ash | 0.56% |
| Carbohydrates | 76.24% |
| Fat by AH | 5.80% |
| Total Fat as Triglycerides | 1.68% |
| Total Fatty Acids | 2.06% |
| Total Saturated Fatty Acids | 0.46% |

TABLE 18

Nutritional data from *Agaricus bisporus*

| | |
|---|---|
| Species name | *Agaricus bisporus* |
| Common name | White Button Mushroom |
| Strain and source | Safeway |
| Harvest Date | Fruiting Body |
| Protein | 15.72% |
| Ash | 5.57% |
| Carbohydrates | 77.02% |
| Fat by AH | 5.80% |
| Total Fat as Triglycerides | 1.68% |
| Total Fatty Acids | Below detection |
| Total Saturated Fatty Acids | 0.46% |

Example 22: Protein Content Data from Strain MK7 Biomats Grown on Two Different Media Biomats were dried in the oven for couple of days (at 99° C.) and left in a desiccator for a few days. Samples were ground and prepared for total nitrogen analysis. About 5% of $H_2O$ was estimated to be in the dried strain MK7 samples. Total protein was calculated to be:

For membrane-grown strain MK7 on MK102 medium—41.2%

For membrane-grown strain MK7 on AUM medium—43.8%

Media Characteristics (Particularly Suitable for Membrane Reactors)

| Medium | Ionic strength (mmol/L) | Osmolality (mOsm) | Carbon source (wt %) | Yield* (g/m²) |
|---|---|---|---|---|
| AUM | 308.5 | 1902 | Glycerol, 10% | 359 |
| MK7-102 | 296 | 1804 | Glycerol, 10% | 507 |
| Lignocellulose | 1401.6 | 2723 | LCB**, 10% | 247.4 |

*Best yield, strain MK7 biomat on membrane, 8.5 mL medium, 35 mm Petri dish, 5-7 days
**Lignoceelulosic biomass-derived from dry hay, treated with sulfuric acid Growth Media Chemistry

AUM-artificial urine medium

| | g/L |
|---|---|
| CaCl2*2H2O | 0.37 |
| MgSO4*7H2O | 0.49 |
| NaCl | 5.2 |
| Na2SO4 | 1.41 |
| Trisodium citrate | 0.61 |
| Li-lactate | 0.1 |
| KH2PO4 | 0.95 |
| K2HPO4 | 1.2 |
| NH4Cl | 1.3 |
| urea | 10 |
| creatinine | 0.8 |
| yeast extract (to account for trace elements and nucleic acids) | 0.005 |
| peptone, bacteriological (to account for amino acids) | 1 |
| FeSO4*7H2O | 0.0012 |
| Na2CO3 | 2.1 |
| H2O | to 1L |
| HCl to adjust pH | 3.5 |

Lignocellulosic biomass medium

| | g/L |
|---|---|
| Ground hay | 100 |
| NH4NO3 | 10.5 |
| Urea | 3.5 |
| CaCl2 | 1 |
| MgSO4*7H2O | 1 |
| KH2PO4 | 4 |
| EDTA-free trace | 0.4 |
| Yeast Extract | 2 |
| H2O to 1L | |
| H2SO4 to adjust pH | |

MK7-102

| | g/L |
|---|---|
| NH4NO3 | 10.5 |
| Urea | 3.5 |
| CaCl2 | 1 |
| MgSO4*7H2O | 1 |
| KH2PO4 | 4 |
| EDTA-free trace | 0.4 |
| Glycerol | 10 |
| Yeast Extract | 2 |
| H2o to 1L | |
| HCl to adjust pH | |

Example 23: This Example Shows the Comparative Nutritional Data from Two *Fusarium* Filamentous Fungi—Strain MK7 and *Fusarium venenatum*

Comparative Nutritional Data Obtained from Strain MK7 and *Fusarium venenatum* Total Protein Analysis

| Units | Analyte | MK7 QCB252 | F.V. Mat produced by SB January 2019 | Quorn (F.V)* |
|---|---|---|---|---|
| Percent dry weight | Total Protein | 43-52% | 42% | 44.0% |
| | Total Fat | 12.0% | 7.4% | 12.00% |
| | Total Fiber | 23.3% | 25.1% | 24.0% |
| | Total sugars | <0.35% | 0.0% | 0.00% |
| | Total Ash | 12.4% | 6.1% | |
| | Total Carb (calculated) | 35.4% | 45.0% | 36.0% |
| | Total Nucleotides | 1.47% | | |

*Product includes protein from non-fungal sources (egg, egg whites, yeast, wheat gluten)

Branched Amino Acid Analysis

| Units | Analyte | MK7 QCB252 | F.V. Mat produced by SB Jan 2019 | Quorn (F.V) | F.V. mycoprotein (from GRAS application) | F.V. for fish food (see ref) | Egg whole |
|---|---|---|---|---|---|---|---|
| Percent of total protein dry weight | Tryptophan* | 1.07% | 1.52% | 1.24% | 1.6% | 0.94% | 1.60% |
| | Cystine | 0.82% | 0.97% | | 0.8% | | 2.21% |
| | Methionine* | 1.54% | 1.66% | 1.59% | 2.1% | 1.51% | 3.08% |
| | Alanine | 10.43% | 5.94% | | 6.0% | | 5.58% |
| | Arginine | 5.67% | 5.94% | | 7.3% | 4.72% | 6.33% |
| | Aspartic | 10.30% | 10.77% | | 10.3% | | 10.35% |
| | Glutamic | 11.56% | 11.46% | | 12.5% | | 13.17% |
| | Glycine | 5.58% | 5.25% | | 4.3% | | 3.35% |
| | Histidine* | 2.11% | 2.90% | 2.69% | 3.5% | | 2.48% |
| | Isoleucine* | 5.42% | 4.56% | 3.93% | 5.2% | 3.96% | 5.02% |
| | Leucine* | 8.25% | 7.04% | 6.55% | 8.6% | 5.85% | 8.56% |
| | Phenylalanine* | 2.52% | 4.01% | 3.72% | 4.9% | | 5.22% |
| | Proline | 4.91% | 5.52% | | 4.5% | | 3.78% |
| | Serine | 4.98% | 4.97% | | 5.1% | | 7.78% |
| | Threonine* | 5.99% | 4.97% | 4.21% | 5.5% | 3.77% | 4.39% |
| | Total lysine* | 7.12% | 8.98% | 6.28% | 8.3% | 5.66% | 6.88% |
| | Tyrosine | 2.33% | 3.73% | | 4.0% | | 4.08% |
| | Valine* | 9.39% | 9.81% | 4.14% | 6.2% | 4.72% | 6.17% |
| | Essential AA total | 43.42% | 45.44% | 34.34% | 45.9% | | 43.4% |
| | Branched chain | 23.06% | 21.41% | 14.62% | 20.0% | | 19.8% |

Vitamins

| Units | Analyte | MK7 QCB252 | F.V. Mat produced by SB January 2019 | Quorn (F.V) |
|---|---|---|---|---|
| IU/100 g wet | Vitamin A | 7.53 | 44 | |
| mg/100 g wet | Folic acid | 0.15 | | |
| mg/100 g wet | B3 niacin | 2.06 | | 0.35 |
| ug/100 g wet | B12 | 1.82 | | |
| mg/100 g wet | B2 | 0.89 | | 0.23 |
| mg/100 g wet | B5 | 0.33 | | 0.25 |
| mg/100 g wet | B1 | 0.01 | | 0.01 |
| IU/100 g wet | D2 | 222 | | |
| mg/100 g wet | Omega-3 Linolenic | 148 | | 400 |
| mg/100 g wet | Calcium | 229 | 1170 | 42.5 |
| mg/100 g wet | Iron | 3.88 | 2.8 | 0.5 |

Fatty Acid Analysis

| Units | Fatty acid | FV mat January 2019 | MK7 |
|---|---|---|---|
| percent of total triglycerides | Capric acid (C10:0) | 0.00% | |
| | Myristic acid (C14:0) | 0.00% | 1.91% |
| | Pentadecanoic acid (C15:0) | 0.00% | |
| | Palmitic acid (C16:0) | 17.32% | 26.75% |
| | Palmitoleic acid (C16:1) | 0.00% | |
| | Margaric acid (C17:0) | 0.00% | |
| | Stearic acid (C18:0) | 11.02% | 7.64% |
| | Oleic acid (C18:1 z-9) | 19.69% | 21.66% |
| | Linoleic acid (C18:2 z-9,12) | 44.88% | 32.48% |
| | Gamma linolenic acid | 0.00% | |
| | Alpha linolenic acid | 0.00% | 3.82% |
| | Arachicid acid (C20:0) | 0.00% | |
| | 11-Eicosenoic acid C20:1 (z-11) | 0.00% | |
| | Behenic acid (C22:0) | 0.00% | |
| | Lignoceric acid (c24:0) | 0.00% | |
| | Other > C20 | 0.00% | |
| | Other < C20 | 0.00% | 2.55% |
| | Saturated | 32.80% | 41.40% |
| | Monounsaturated | 20.00% | 22.29% |
| | Polyunsaturated | 47.20% | 36.31% |

Example 24. RNA Content Measurement from Various Filamentous Fungi

Purine Analysis Experimental Procedure: Preparation of 1000 m/ml Purine Standards: 100 mg of each purine base (Adenine, Guanine, Xanthine and Hypoxanthine) were added separately to 4 100 ml volumetric flasks. 90 ml of ultra-purified water was added to each flask and the flasks were shaken to divide the purine solids. 10M NaOH prepared in ultra-purified water was added dropwise until the purine base began to dissolve. Flasks were shaken repeatedly until all solids were fully dissolved. Additional base was added as needed to provide complete dissolution. Flasks were capped and stored under refrigeration.

Preparation of 200 μg/ml mixed purine standard: 20 ml of each 1000 ug/ml purine standard was added to a 100 ml volumetric flask the volume was brought to 100 ml by addition of water. Stored under refrigeration Preparation of pH 2.5-2.8, 150 mM Phosphate Buffer: 150 mmol sodium phosphate buffer solution was prepared by dissolving 74.88 g of NaH2PO4 in 2 liters of ultra-purified water. The solution was filtered thru a 0.45 um pore size filter under vacuum. 7.88 ml of 80% phosphoric acid was added to 2 liters of ultra-purified water and the resulting solutions were combined. If outside the buffer range of pH 2.5-2.8 the pH can be adjusted by dropwise addition of 80% phosphoric acid to an approximately pH 2.6 endpoint.

Sample preparation: Freeze dried mushroom samples were processed as obtained. Wet samples were transferred to tared 15 ml falcon tubes. The samples were then frozen at −80 F in preparation for lyophilization. The pre-frozen samples were lyophilized for 24-48 hrs. on a Labconco lyophilizer until dry.

Dried samples were weighed, and the weight recorded. The dried material was ground to a fine powder in a mortar and pestle and weighed into a 50 ml Erlenmeyer flask to obtain ca 500 mg sample. 15 ml of 70% perchloric acid was added to the reaction flask. The reactions were then heated to 95 C in a water bath for 1 hr with stirring by magnetic stir bar. The flasks were removed from the water bath and a 5 ml sample was removed from each reaction and transferred to a 15 ml falcon tube. pH was increased by dropwise addition of a KOH solution until the solution was at pH4. The volume of the neutralized sample was recorded, and the solution was centrifuged at 4000 rpm for 30 min. pH was checked after centrifugation and adjusted as necessary, the final volume was recorded. 3 ml of the supernatant was drawn up with a syringe and filtered thru a 0.45 um syringe filter for submission to HPLC analysis.

HPLC Conditions:
- HPLC: Waters e2695 Separations Module
- Column: Shodex Asahipak GS-320HQ 7.5 mm×300 mm
- Solvent: 150 mM Sodium Phosphate buffer (pH 2.5-2.8)
- Injection volume: 10 uL
- Flow rate: 0.6 mL/min
- Column temperature: 35° C.
- Detection wavelength: 260 nm RNA Content

| Species | RNA wt % in dry biomat |
|---|---|
| Hericululm erinaceus (Lion's Mane) | 0.76-2.23 |
| Sparassis crispa (cauliflower) | 1.56 |
| Pleurotus ostreatus (pearl) | 0.95 |
| Morchella esculenta | 0.51 |
| Morchella conica | 0.14 |
| Fusarium venenatum | 3.52-4.86 |
| MK7 strain | 1.3-1.95 |

Example 25. Toxicity Data from the Biomats of Filamentous Fungi *Fusarium venenatum* and *Morchella conica* (Black Morel)

Toxicity/Growth Studies with *Daphnia magna*

*Fusarium venenatum* biomat did not result in acute toxicity to *Dapnia magna*, a highly sensitive macroinvertebrate commonly used for toxicity assays (EPA Publication, 1987; Guilhermino et al., 2000).

Live *D. magna* was purchased from Carolina Biological Supply (Cat #142330, Burlington, NC). Immediately after receiving the cultures from the supplier, 100 mL of the liquid medium containing live *D. magna* was mixed with 800 mL of Arrowhead Spring Water (Nestle Waters North America, Inc. Stamford, CT) in a sanitized glass bowl (rinsed with 70% isopropanol and dried). The culture was gently mixed by stirring with a sanitized plastic spoon and 400 mL of this liquid, without any *Daphnia*, was removed and stored in an Arrowhead Spring water bottle at 4° C. for later use. One-quarter of a pellet of *Daphnia* food (Carolina Biological Supply, Cat #14-2316) was added to the remaining 500 mL of liquid in the bowl containing the *Daphnia*. The bowl was covered with a loose-fitting plastic wrap and the culture was incubated at room temperature (21±2° C.) as directed in the manual provided by the supplier. After 48 hours of growth and observation, the live *Daphnia* were used for the growth/toxicity experiments.

Sterile Petri dishes (Fisherbrand 100×15 mm, Cat #08-757-13, Thermo-Fisher) were filled with 35 mL of the liquid growth medium (mixture of spring water/Carolina Biological Supply medium) that was stored at 4° C. (described above). The liquid medium was allowed to equilibrate to room temperature. Four active *Daphnia*, each approximately 1-1.2 mm in length, were captured with an eye dropper (Carolina Biological Supply, capture method described in suppliers manual) and added to each of the eight Petri dishes. Additionally, four of the Petri dishes received 0.15 g of moist *F. venenatum* biomat (18% solids) and four Petri dishes received 0.03 g dry *Daphnia* food. The biomass was produced after 5 days of growth on MK7-102 medium, harvested from the tray, gently pressed by hand to remove excess medium and steamed for 30 minutes to kill the cells. The steamed biomass was pressed in a Francesco Palumbo grape press to remove liquid until a moisture content of approximately 18% solids (82% liquid) was obtained. The pH in both the control and *F. venenatum* biomass containing Petri dishes ranged from 7.4 to 7.8 during the toxicity experiments. Live *Daphnia* were counted every 24 h in each of the Petri dishes, as shown in the following table.

After four days, the control treatment had an average of 3.50 live *Daphnia* per dish (std dev=1.29), while the *F. venenatum* treatment had an average of 3.75 live *Daphnia* per dish (std dev=0.50). At this time, the control treatment had an average of 0.75 deaths per dish (std dev=0.96), while the *F. venenatum* treatment had an average of 0.25 deaths per dish (std dev=0.5).

In summary, these data indicated that steamed *F. venenatum* biomass does not result in acute toxicity to *Daphnia* as accessed in the described manner.

*Daphnia* Toxicity Study on *Fusarium Venenatum*

| Adult Daphnia ~3 mm length, Temperature 20.0 ± 0.5 | | | | | |
|---|---|---|---|---|---|
| F. Venenatum | t = 0 | day = 1 | day = 2 | Initial pH | Final pH |
| #1 | 4 | 3 | 3 | 7.38 | 7.42 |
| #2 | 4 | 4 | 3 | | |
| #3 | 4 | 3 | 2 | | |
| #4 | 4 | 3 | 3 | | |
| | | mean | 2.75 | | |
| | | std dev | 0.50 | | |
| Control | t = 0 | t = 1 | t = 2 | Initial pH | Final pH |
| #1 | 4 | 4 | 4 | 7.4 | 7.63 |
| #2 | 4 | 2 | 1 | | |
| #3 | 4 | 3 | 3 | | |
| #4 | 4 | 4 | 3 | | |
| | | mean | 2.75 | | |
| | | std dev | 1.26 | | |

| Immature Daphnia ~1 mm length, Temperature 19.2 ± 0.5 | | | | | | |
|---|---|---|---|---|---|---|
| F. venenatum immature | t = 0 | day = 1 | day = 2 | day = 3 | day = 4 | Initial pH | Final pH |
| #1 | 4 | 4 | 4 | 4 | 4 | 7.47 | 7.58 |
| #2 | 4 | 4 | 4 | 4 | 4 | | |
| #3 | 4 | 4 | 4 | 4 | 4 | | |
| #4 | 4 | 4 | 4 | 4 | 3 | | |
| | | | | mean | 3.75 | | |
| | | | | std dev | 0.50 | | |
| Control | t = 0 | t = 1 | t = 2 | t = 3 | t = 4 | Initial | Final |
| #1 | 4 | 4 | 5 | 5 | 5 | 7.38 | 7.75 |
| #2 | 4 | 4 | 4 | 4 | 4 | | |

| | | | | | |
|---|---|---|---|---|---|
| #3 | 4 | 3 | 3 | 3 | 3 |
| #4 | 4 | 2 | 2 | 2 | 2 |
| | | | | mean | 3.50 |
| | | | | std dev | 1.29 |

Mycotoxin Content
Method Reference US-Multitoxin LCMSMS 45-2-LWI

| | Fusarium venenatum 1 (biomat unground, cooled) | Black Morel (biomat unground, frozen) |
|---|---|---|
| Alfatoxin B1 | <1.3 ppb | <1.3 ppb |
| Alfatoxin B2 | <1.2 ppb | <1.2 ppb |
| Alfatoxin G1 | <1.1 ppb | <1.1 ppb |
| Alfatoxin G2 | <1.6 ppb | <1.6 ppb |
| Fumonisin B1 | <0.1 ppm | <0.1 ppm |
| Fumonisin B2 | <0.1 ppm | <0.1 ppm |
| Fumonisin B3 | <0.1 ppm | <0.1 ppm |
| Ochratoxin A | <1.1 ppb | <1.1 ppb |
| Deoxynivalenol | <0.6 ppm | <0.6 ppm |
| Acetyldeoxynivalenol | <0.8 ppm | <0.8 ppm |
| Fusarenon X | <0.4 ppm | <0.4 ppm |
| Nivalenol | <0.6 ppm | <0.6 ppm |
| T-2 Toxin | <0.2 ppm | <0.2 ppm |
| HT-2 Toxin | <0.2 ppm | <0.2 ppm |
| Neosolaniol | <0.4 ppm | <0.4 ppm |
| Diacetoxyscirpenol | <0.4 ppm | <0.4 ppm |
| zearalenone | <51.7 ppb | <51.7 ppb |

Example 26. Characterization of a Liquid Dispersion Comprising Strain MK7 Biomat Particles Materials: MK7 vegan milk sample: app. 8.25% solid in water All the measurements were done at room temperature (25° C.), unless otherwise noted.

Appearance and color: Appearance is slightly off white with slight beige tones. Smell of is very slightly woody.

Refractive index, density and particle size analysis in 10-1000× diluted samples are illustrated in FIG. 20.

Dynamic light scattering (DLS) was used to analyze the particle size in solution.

Milk structure under optical microscope is illustrated in FIGS. 21A (10×) and 21B (100×).

Fat content of the sample (8.25%) was found to be 0.6 g/100 g.

pH content was found to be as shown below.

| Concentration | 0.0825% | 0.825% | 4.125% | 8.25% |
|---|---|---|---|---|
| pH | 6.73 | 6.17 | 5.99 | 5.91 |

Figure 22:
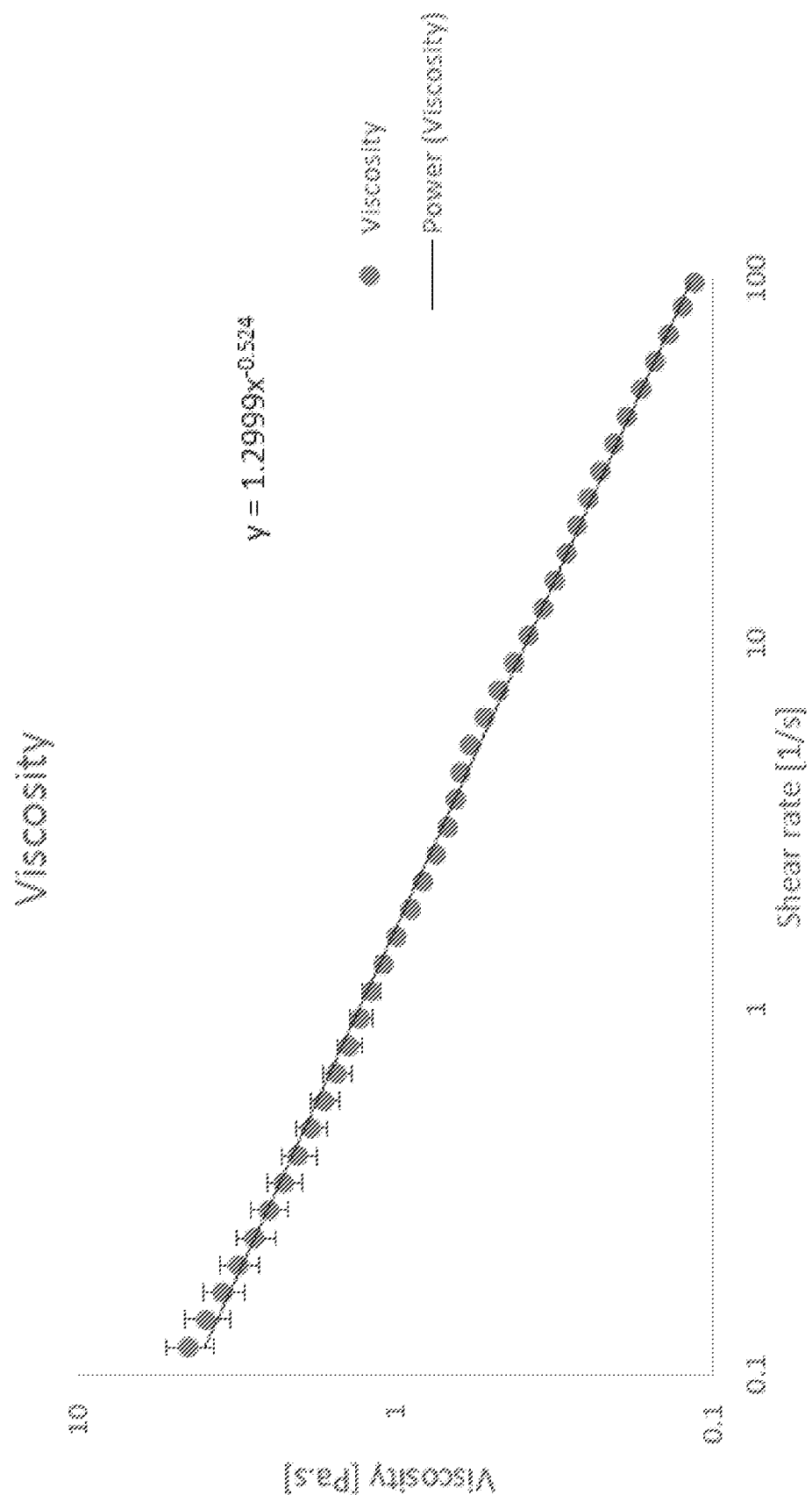
FIG. 22. Plot of viscosity of vegan milk sample against shear rate.

Viscosity: The viscosity of vegan milk sample at original concentration (8.25%) was studied. FIG. 22 was obtained by averaging three repeating measurements. The sample viscosity decreases with the increasing shear rate, indicating that it is non-Newtonian fluid with sheer-thinning behavior. It also means that the particles are much easier to get deformed under large shear rate. For a giving shear rate, the viscosity of sample can be determined by the power-law equation. This provides the opportunity to compare this vegan milk sample to other cow's milks or smoothies.

No visible separation of the milks was observed after 2 weeks or 4 weeks.

Example 27. Process for Making a Liquid Dispersion Using the Strain MK7 Filamentous Fungus In a high speed blender (Vitamix) 200 grams strain MK7, 600 grams water and 1 teaspoon vanilla extract were combined and blended until smooth (at least 90 seconds). The blended mixture was heated on low heat until fungal scent was reduced, preferably to the point of being non-existent (app. 20-30 minutes). The heat was kept low to achieve a maximum of slow speed rolling boil, which initiated when the MK7 milk reached app. 80 C. The MK7 milk was lightly boiled, temperature between 90-92 C and was allowed to boil without disruption without stirring or whisking. The heated blended mixture was allowed to cool and use.

After the heat cycle was completed and the milk was removed from the pot, a residual line was observed on the inside of the vessel at the intersection of the MK7 milk and air. The residue was hard and a well attached amalgamation of dehydrated/cooked strain MK7.

Example 28: Crepes

Ingredients:
King Arthur All Purpose Flour—11.7% Gluten content.
C &H Granulated Sugar.
Strain MK7 Biomass—QCB-249-10% Glycerol—Sep. 3, 2018.
MK7 Milk—QCB-249-10% Glycerol—Sep. 3, 2018 (25% Biomass before cooking)
Nielsen Vanilla Paste.
Plugra Unsalted Butter 82% Fat.
Equipment:
De Buyer Teflon Crepe Pan.
MK7 Crêpe 1

| All Purpose Flour | 120 g |
|---|---|
| Sea Salt | 0.5 g |
| Granulated Sugar | 50 g |
| Fresh Whole Eggs | 100 g |
| Fresh Egg Yolks | 30 g |
| MK7 Milk | 250 g |
| Vanilla Paste | 5 g |
| Unsalted Butter | 30 g |
| Clarified Butter | As Needed |
| Fine Turbinado Sugar | As Needed |
| Total | 585.5 g |

The original fresh milk content of a crêpe batter was replaced with MK7 milk. Milk was produced as follows: 200 grams strain MK7, 600 grams of water, 2 grams vanilla. Mixture was size reduced in a vitamix and heat treated without nitrogen treatment for 20 minutes at low temp boil. The crepe batter was too thick.
MK7 Crêpe 2

| All Purpose Flour | 120 g |
|---|---|
| Sea Salt | 0.5 g |
| Granulated Sugar | 50 g |
| Fresh Whole Eggs | 150 g |
| Fresh Egg Yolks | 30 g |
| MK7 Milk | 250 g |
| Fresh Whole Milk | 100 g |
| Water | 50 g |
| Vanilla Paste | 5 g |
| Unsalted Butter | 30 g |
| Clarified Butter | As Needed |
| Fine Turbinado Sugar | As Needed |
| Total | 785.5 |

A combination of liquids was used to adjust the batter thickness (whole eggs, fresh milk and water). This adjustment yielded appropriate texture and flavor. Sugar may be omitted for savory crepes and savory flavors like onion and garlic powders and herbs added.

MK7 Crêpe 3

| Ingredients | Weights |
|---|---|
| All Purpose Flour | 80 g |
| MK7 Flour | 40 g |
| Sea Salt | 0.5 g |
| Granulated Sugar | 50 g |
| Fresh Whole Eggs | 150 g |
| Fresh Egg Yolks | 30 g |
| MK7 Milk | 250 g |
| Fresh Whole Milk | 100 g |
| Water | 50 g |
| Vanilla Paste | 5 g |
| Unsalted Butter | 30 g |
| Clarified Butter | As Needed |
| Fine Turbinado Sugar | As Needed |
| Total | 785.5 |

Part of the flour was replaced with MK7 flour to increase the proteins. It was observed that the MK7 flour crepe batter requires more liquid since strain MK7 has a 150% hydration power (flour standards are 60 to 70%). The texture of the crepe was more of a tortilla without the addition of extra water.

Example 29: Pasta Dough

Ingredients:
  Strain MK7 Biomass—QCB-249-10% Glycerol—Sep. 3, 2018
  MK7 Flour—QCB-249-10% Glycerol—Sep. 3, 2018
  Bob's Red Mill Semolina.
  Delallo 100% Organic Double 00 flour.
  Bottled Water—PH: 6.5.
Equipment:
  KitchenAid food processor and pasta roller.
1. Pasta Dough Made with Semolina, Mk7 Flour and Water.

| Ingredients | Weights |
|---|---|
| Semolina | 100 grams |
| MK7 Flour | 50 grams |
| Cold Water | 100 grams (66.66% Hydration) |
| Sea Salt | 4 grams |
| Total | 254 grams |

Dough was mixed by hand and no strain MK7 taste was detected. MK7 flour increases the need of liquid hydration from 50% in a regular pasta dough to app. 66.66% for a dough made with ⅔ semolina and ⅓ MK7 flour.

2. Pasta Dough Made with Semolina, Mk7 Flour and Eggs.

| Ingredients | Weights |
|---|---|
| Semolina | 100 grams |
| MK7 Flour | 50 grams |
| Cold Whole Eggs | 100 grams (66.66% Hydration) |
| Sea Salt | 5 grams |
| Total | 255 grams |

Dough was mixed by hand. No detection of strain MK7 taste. The egg base dough had a richer flavor. The texture was similar to trial #1 but slightly less gluten development caused by the fat in eggs (⅓ fat in yolks, so about 13% of the total mass of trial #2). The egg base dough was harder to mix by hand because of the fat interfering with the gluten. A food processor may be used to produce texture that is smoother and like trial #1. The 20% increase of salt in the pasta dough gave good results.

3. MK7 Flour Hydration

| Ingredients | Weights |
|---|---|
| MK7 Flour | 50 grams |
| Cold Water | 75 grams (150% Hydration) |
| Total | 125 grams |

Dough was mixed by hand. Strain MK7 needs about 150% of water to hydrate in a similar manner to standard flour and starch comparative dough. For reference: white wheat flours require 60 to 70% hydration and starches 70 to 90%.

4. Pasta Dough Made with Double 00 Flour, MK7 Flour and Water to Compare to Trial #1.

| Ingredients | Weights |
|---|---|
| Double 00 Flour | 100 grams |
| MK7 Flour | 50 grams |
| Cold Water | 100 grams (66.66% Hydration) |
| Sea Salt | 5 grams |
| Total | 255 grams |

Dough was mixed by hand. No detection of strain MK7 taste. The texture was smoother than trial #1 with the double 00 flour, which confirmed the performance of a much finer milled MK7 flour.

5. Pasta Dough Made with Double 00 Flour, MK7 Flour and Eggs to Compare to Trial #2.

| Ingredients | Weights |
|---|---|
| Double 00 Flour | 100 grams |
| MK7 Flour | 50 grams |
| Cold Whole Eggs | 100 grams (66.66% Hydration) |
| Sea Salt | 5 grams |
| Total | 255 grams |

Dough was mixed in the food processor. No detection of strain MK7 taste. The texture was smoother than trial #2 with food processor and then finished by hand, which confirmed that the food processor performs better for fat base pasta dough.

6. Pasta Dough Made with Semolina, Double 00 Flour, MK7 Flour and Water to Compare to Trial #1 and #4.

| Ingredients | Weights |
|---|---|
| Semolina | 50 grams |
| Double 00 Flour | 50 grams |
| MK7 Flour | 50 grams |
| Cold Water | 100 grams (66.66% Hydration) |
| Sea Salt | 5 grams |
| Total | 255 grams |

Dough was mixed by food processor and finished by hand. No detection of strain MK7 taste. The texture was very similar in terms of smoothness as trial number 4. The combination of two flours with MK7 flour resulted in a diminishment of the semolina like texture and lessened the wheat flour texture.

7. Pasta Dough Made with Semolina, Double 00 Flour, MK7 Flour and Eggs to Compare to Trial #2 and #5.

| Ingredients | Weights |
| --- | --- |
| Semolina | 50 grams |
| Double 00 Flour | 50 grams |
| MK7 Flour | 50 grams |
| Cold Whole Eggs | 100 grams (66.66% Hydration) |
| Sea Salt | 5 grams |
| Total | 255 grams |

Dough mixed by food processor and finished by hand. No detection of strain MK7 taste. The texture was smooth, similar to trial number 5, and the same as above with the pairing of the two flours with MK7 flour.

Example 30: Spatzle

Ingredients:
MK7 Biomass—QCB-249-10% Glycerol—Sep. 3, 2018
MK7 Flour.
King Arthur All Purpose Flour 11.7% Gluten
Equipment:
None
Trial #1:

| Ingredients | Weights |
| --- | --- |
| All Purpose Flour | 200 grams |
| MK7 Flour | 100 grams |
| Whole Eggs | 200 grams (66.66% Hydration) |
| Sparkling Water | 160 grams |
| Sea Salt | 8 grams |
| Total | 668 grams |

Dough was mixed by hand and dispersed with a dough scraper. No detection of strain MK7 taste. It was decided that the spatzle could be more moist inside and would benefit from an addition of cream or similar i.e. heavy cream, crème fraiche, sour cream, buttermilk, yogurt, as well as addition of Nutmeg. It was allowed to dry overnight after cooking and finished the following day.
Trial #2:

| Ingredients | Weights |
| --- | --- |
| All Purpose Flour | 200 grams |
| MK7 Flour | 100 grams |
| Whole Eggs | 200 grams (66.66% Hydration) |
| Sparkling Water | 160 grams |
| Crème Fraiche | 40 grams |
| Sea Salt | 8 grams |
| Nutmeg Powder | 0.5 grams |
| Total | 708.5 grams |

Dough was mixed by hand. No detection of strain MK7 taste. The rested overnight spatzle had the proper color when finished in butter. The cream addition brought the necessary moisture. Numerous chefs at the French Pastry School approved of the product.

Example 31: Bacon

Ingredients:
Strain MK7
2 tablespoons Soy
1.5 tablespoons A1
1 teaspoon liquid smoke
2 tablespoons nutritional yeast
½ teaspoon paprika
1 teaspoon honey Strain MK7 biomat was cut into strips. A marinade/coating was prepared. Both sides of strain MK7 were coated with coating a and fried in oil until browned, patted dry, and dehydrated in dehydrator to drive off excess moisture, until desired texture is achieved. The resulting bacon analogue performed well in terms of both texture (i.e. crispy) and flavor (had an appealing bacon like flavor). Chefs at the French Pastry School approved of the product.

Example 32: Bread

Ingredients:
0.5 cup unsweetened 7-grain cereal (store bought)
2 cups boiling water
1 envelope dry yeast
3 cups bread flour
1 cups MK7 flour
1 tablespoon olive oil
1 tablespoon dark brown sugar
1.5 teaspoons salt
2 teaspoons sesame seeds
2 teaspoons flax seeds
2 teaspoons poppy seeds
2 cups water 2 cups boiling water was poured over 7 grain serial and allowed to soak for 20 minutes to soften the grain. Yeast was added to softened cereal. 1 cup bread flour, oil, sugar and salt was added and stirred gently until smooth. MK7 flour was mixed with remaining bread flour and slowly mixed into above until a dough was formed. Covered and let rest (15-20 minutes). Note: resting should be in a warm place. The dough was kneaded until smooth and elastic. Additional flour was added as required. The kneading was for about 10-15 minutes. A large bowl was oiled. Dough was coated with oil, placed in oiled bowl and covered. The dough was allowed to rise in warm area until doubled, about 1.5 hours. Seeds were mixed in and the dough was punched down. (Turn dough out onto lightly oiled surface. Knead briefly with app ½ seeds.) The dough was shaped into a loaf. Baking sheet was sprinkled with app. 2 teaspoons seeds. Loaf was placed atop seeds, covered with towel and allowed to rise in warm area until almost doubled, about 30 minutes. An oven rack was positioned in center of oven and another oven rack at the bottom of the oven. Oven was pre heated to 425 F. Loaf was brushed with water. Remaining seed mixture was sprinkled on loaf. Diagonal slashes app. ⅛" deep were cut on surface of loaf and baking sheet with loaf was placed in oven. (2 cups water was poured into hot pan on lower rack in oven for steaming.) loaf was baked until golden and crusty and tester inserted into center came out clean, about 35 minutes. The resulting bread had good crumb and very good taste. The addition of MK7 flour was not detectable in the resulting loaf.

Example 33: Vegan Chocolate Ice Cream

Ingredients
- 95 grams raw Cashews
- 750 grams MK7 milk
- 0.7 grams Xanthan Gum
- 0.2 grams Instant Espresso
- 20 grams Cocoa Powder
- 1 gram Salt
- 2 grams Vanilla Extract
- 110 grams Turbinado Sugar (melted into MK7 milk)
- 150.5 grams Green & Blacks dark Chocolate 70%
- 20 grams Ghirardelli sweet cocoa powder (baking chocolate)
- 15 grams Rumford cornstarch (non-GMO)

1:3 MK7 milk analog: In a high speed blender (Vitamix) 200 grams strain MK7, 600 grams water and 1 teaspoon vanilla extract, was combined and blended until smooth (app. seconds). Blended mixture was heated on low heat for 20 minutes. (In another version of the recipe, both blending and heat treatment was also done under nitrogen (i.e. bubble nitrogen through the MK7 milk analog during either or both the size reduction in the Vitamix and/or the heat cycle). Use of Nitrogen resulted in an increase in milk analog creaminess and produced a sweet flavor.) Heat was kept low; to a maximum of slow speed rolling boil. Sugar was added to MK7 milk during the last 5 minutes of heat treatment and mixed to melt into milk. (If MK7 milk is pre-made, heat milk and add sugar to melt.) A foam was visible on top with small parts of the lower liquid showing signs of slow boiling.

In a high-speed blender, all ingredients were combined and blended on high for 120 seconds. According to standard teachings, it is suggested to keep a small part of the mixture aside and dissolve the starch into the mixture separately while whisking briskly to avoid clumping. If a starch mixture is made separately, adding it to the master mix should be done gradually to avoid clumping.

The mixture was poured into ice cream making vessel and covered with cling film with cling film pressed against the surface of the mixture so a skin does not form while mixture is cooling. The mixture was cooled but not frozen. The mixture was churned in ice cream maker for at least 30 minutes but not more than an hour (depending on desired consistency). Packaged into appropriate container and frozen overnight.

Example 34: Chicken Nuggets

Ingredients
- 200 g strain MK7
- 4 g chicken stock (can be meat based chicken stock or vegetarian based chicken stock)
- 4 g binder (egg albumen or vegetarian binder)
- 3 g fat (duck fat works great as does cocoa butter. Other fats have also been successfully used)

Biomat particle size reduction was done with a knife to achieve the desired particle size. All ingredients were combined and processed until the desired particle size distribution was achieved. (If using a food processor, it is recommended to pulse the food processor for seconds and use a spatula to remove biomass stuck to the sides and re-integrate into that biomass closer to the blades, and repeat this 3 times. One can process more or less as desired for the final product.) The size reduced biomass was thoroughly mixed with a spoon/spatula to insure that all ingredients were intimately mixed. Patties of the desired size were formed and steamed for 30 minutes to set the binder. (Note that some binders may require more or less time.) The steamed patties were cooled. In some patties, breading was applied and heat treated to secure breading to patty

Example 35: Burger Breakfast Sausage

Ingredients: Spice Mix
- 30 g molasses
- 30 g tamari
- 15 g sunflower oil
- 15 g A1 sauce
- 21 g ground flax seed
- 21 g nutritional yeast
- 14 g whole wheat four
- 6 g black pepper
- 6 g sage
- 1 g thyme
- 0.5 g nutmeg Ingredients: Burger
- 100 g food processed strain MK7 (Starch feedstock)
- 100 g TVP (Textured Vegetable Protein: re-constituted from dried state in a half and half mixture of vegetable and mushroom bullion)
- 20 g of spice mix
- 20 g cooked brown rice
- 15 g cooked onion (yellow onion cooked in oil until softened)
- 4 g dried egg albumin
- 4 g cocoa butter
- Optional but recommended: food grade red dye (see Pic)

In a mixing bowl the spice mixture was combined and mixed until a homogeneous mixture was obtained. This was allowed to rest for 15 minutes so that the liquids were sufficiently absorbed producing a paste like mixture. In a food processor, the particle size of the biomass was reduced to the desired size i.e. a size consistent with that expected from burger (or sausage). The burger ingredients were combined in a bowl and mixed until homogeneous. With dampened hands, burger patties were formed. The patties were steamed for 30 minutes or baked at 350 for 30 minutes, and fried.

Example 36: Hot Dog Bologna

Ingredients
- 250 g strain MK7
- 1 g ground cumin
- 1 g ground cardamom
- 1 g mace
- 1.5 g black mustard seeds
- 1 g ground coriander
- 4 g black pepper
- 4 g salt
- 5 g fresh minced garlic
- 6 g granulated sugar
- 4 g paprika
- 50 g onion, peeled and chopped
- 18 g vegetable oil (app. 3 tablespoons)
- 9 g soy sauce (app. 2 tablespoons)
- 30 g almond meal
- 140 g wheat gluten
- 2 g arrowroot All of the ingredients except the gluten and arrowroot were added to a food processor. The mixture was processed until completely smooth for at least 60 seconds, and the processed mixture was transferred into a large bowl with a spatula. Wheat gluten and arrowroot was stirred in with a wooden spoon and worked into a dough. It was noted that addition of the gluten and arrowroot formed a dense dough.

The amount of gluten and the amount of processing the strain MK7 may be reduced as desired to achieve a desired density.

The dough was placed on a clean surface, and divided into 8 equal portions. 8 pieces of wax paper and 8 pieces of Al foil of a size capable of encasing a hot dog of the appropriate size were prepared. Each portion of dough was rolled into a shape similar to that of a hot dog. on a table with a consistent pressure from your hand. If dough is dry or has cracks, it may be worked with wet hands thereby forming a smooth surface. Each hot dog was individually wrapped in wax paper and again in aluminum foil. The ends of the foil were twisted into a tootsie roll shape. The hot dogs were steamed in a steamer for 45 minutes. Each hot dog was unwrapped and let cool.

Example 37: Membrane Comparison

A number of simple bioreactor setups were constructed to compare the effects on biomat growth of membrane material. Biomats were grown in each bioreactor under identical conditions (sealed and humid, 26° C., fungus inoculated through the growth medium) and sampled at day 6. The results are shown in Table 19.

TABLE 19

Comparison of membrane materials

| Membrane 1 material | Membrane 1 pore size, μm | Membrane 2 material | Membrane 2 pore size | Hydrophilic or hydrophobic? | Upgrowth, $g/m^2$ | Downgrowth, $g/m^2$ |
| --- | --- | --- | --- | --- | --- | --- |
| None | n/a | None | n/a | n/a | 182 | |
| Polyvinylidene fluoride (PVDF) | 5 | None | n/a | Hydrophilic | 354 | 391 |
| Recycled PVDF | 5 | None | n/a | Hydrophilic | 329 | 333 |
| Polypropylene (PP) | 5 | None | n/a | Hydrophobic | 265 | 76 |
| Polypropylene (PP) | 10 | None | n/a | Hydrophobic | 292 | 306 |
| Mixed cellulose esters (MCE) | 0.45 | None | n/a | Hydrophilic | 31 | 68 |
| Polyamide (nylon) | 0.22 | None | n/a | Hydrophilic | 0 | |
| Polyamide (nylon) | 11 | Polyamide (nylon) | 11 | Hydrophilic | 336 | 365 |
| Recycled nylon | 11 | None | n/a | Hydrophilic | | 187 |
| PP (blue membrane) | 5 | None | n/a | Hydrophilic | 165 | |
| PP (blue membrane) | 5 | Nylon | 0.2 | Hydrophilic | 0 | |
| PP (blue membrane) | 5 | Gas headspace + nylon | 0.2 | Hydrophilic | 208 | |
| PP (blue membrane) | 5 | MCE | 0.45 | Hydrophilic | 0 | |
| PP (blue membrane) | 5 | PP (blue membrane) | 5 | Hydrophilic | 167 | |
| Polyvinylidene fluoride (PVDF) | 5 | PVDF | 5 | Hydrophobic | 132 | |
| Parafilm | n/a | None | n/a | n/a | 0 | |
| Saran wrap | n/a | None | n/a | n/a | 0 | |
| PP (blue membrane) | 5 | PP (blue membrane) | 5 | Hydrophilic | 0 | |
| PP (blue membrane) | 5 | PP | 10 | Hydrophilic | 0 | |

As shown in Table 19, a hydrophilic PVDF membrane (MilliporeSigma, Burlington, MA) was the best-performing membrane material under the provided conditions, yielding the best density of both upgrowth (i.e. growth on the upper side of the membrane) and downgrowth (i.e. growth on the lower side of the membrane) of the biomat of any membrane arrangement tested. In addition to providing the best growth characteristics, the membrane is flexible and remained "clean," i.e. suitable for reuse, after harvesting of the biomat; a subsequent experiment showed that the same membrane could be reused, with no cleaning step, to achieve approximately 80% of initial efficiency. Another subsequent experiment demonstrated comparable results between the 5 μm PVDF membrane shown in Table 19 and a 0.2 μm PVDF membrane when the fungus was inoculated on a top side (i.e. opposite the feedstock) of the membrane. Polypropylene and nylon membranes also provided consistent high yields, although it was found that polypropylene membranes can become clogged. Low-porosity nylon membranes did not provide sufficient structural integrity and tended to crack mid-experiment.

Example 38: "Upside-Down" Flask Bioreactor

Figure 25:
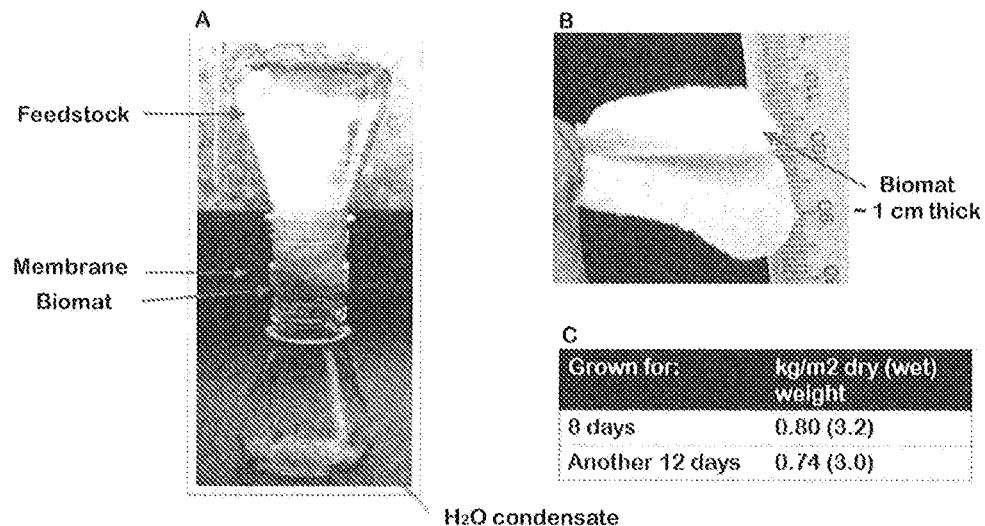
FIG. 25. Illustration of hermetic embodiment of bioreactor configuration "4."

Referring now to FIG. 25A, a "hermetic" (tightly sealed against the environment) embodiment of a bioreactor according to the configuration labeled "4" in FIG. 23 is illustrated. As FIG. 25A illustrates, the bioreactor is an "upside-down" bioreactor formed by sealing together two 125 mL Erlenmeyer flasks at the neck; the membrane (PVDF, pore size 5 μm) is disposed within the necks of the flasks, the feedstock is disposed in the upper flask, and the biomat is growing downwardly from the membrane into the gas headspace provided within the lower flask. Again, condensed water can be seen in the bottom of the lower flask. This embodiment permits continuous replenishment of the feedstock and semi-continuous harvesting and/or sampling of the biomat. Fungus was inoculated within the feedstock (i.e. above the membrane).

Referring now to FIG. 25B, a biomat having a thickness of approximately 1 cm has been harvested as part of a second harvest from the bioreactor after 12 days of growth (at day 20 after inoculation, with the first harvest conducted at day 8). The biomat grew at an average rate of approximately 1 mm thickness per day, producing a dry yield of biomat of up to about 100 g/m², for at least the first three weeks after inoculation. FIG. 25C provides the dry and wet yields of the bioreactor after 8 days (first harvest) and 12 additional days (second harvest). This bioreactor embodiment permits the production of at least about kilograms of dry biomass per square meter per week, equivalent to about 0.35 kilograms of protein per square meter per week, utilizing a feedstock derived from food waste or human waste. 0.35 kilograms per week is approximately equal to the protein requirement for a 73-kilogram human; thus, one square meter of membrane growth area may be sufficient to supply the protein needs of one adult human in, e.g., crewed spaceflight applications or terrestrial applications in which available space is limited.

After harvesting, the PVDF membrane of this Example did not retain biomass visible to the naked eye; as illustrated in FIG. 25B, the membrane appears "clean." However, sufficient cells remained on the membrane to effectively reinoculate the membrane for continued rapid growth. Other similar experiments have shown that biomats can be regrown on a previously used membrane without the need to actively re-inoculate the membrane.

As in several other Examples, PVDF performed particularly well as a membrane material with regard to structural integrity, cleanliness, biomat production, and ease of biomat harvesting; other materials, particularly nylon, have a tendency to fail, crack, clog, or otherwise diminish in performance after only a few days, and are therefore inferior to PVDF in their robustness and suitability for use in long-term (e.g. 2 to 7 weeks) experiments.

Example 39: Bag Bioreactor

Two types of "bag bioreactors" were designed, fabricated, and evaluated for biomat growth performance. A first bag bioreactor was constructed by fashioning a bag from a Gore-Tex material, with feedstock disposed inside the bag and the inoculum of the filamentous fungus placed on the outside of the bag. After 7 days, a biomat ranging in thickness from about 1 mm near a top of the bag and about 6 mm near the bottom of the bag had formed; it is believed that this difference may be attributed to variations in the fluid pressure imparted on various portions of the bag (i.e. greater fluid pressure on the bottom of the bag than on the top). The yield of the biomat was 498 g/m² on a wet basis (estimated 124.5 g/m² on a dry basis), giving a dry production rate of about 17.8 g/m²/day and a carbon conversion efficiency of about 35.8%.

Figure 26:
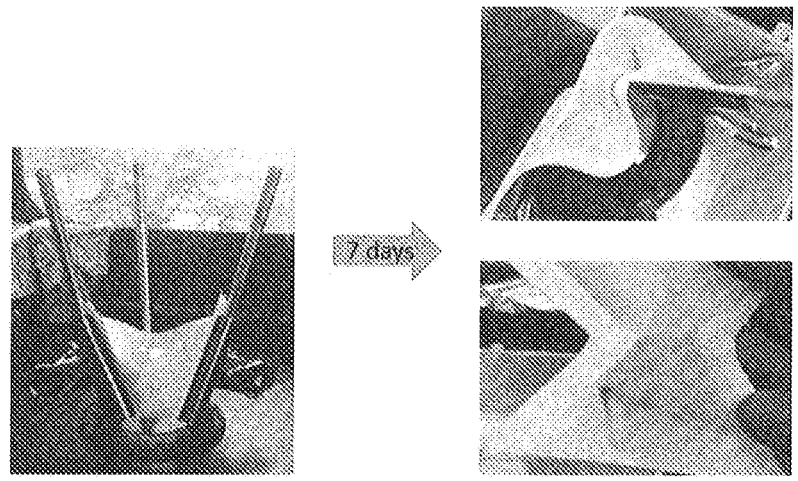
FIG. 26. Biomat growth process of bag reactor.

A second bag bioreactor was constructed by fashioning a bag from a double layer of a PVDF membrane having a pore size of 5 In this embodiment, the filamentous fungus was inoculated through the media (i.e. from inside the bag). After 7 days, substantially all of the feedstock had been consumed, and the carbon conversion efficiency was estimated at 73.4%. The biomat growth process of this bag bioreactor is illustrated in FIG. 26.

Example 40: "Upside-Down" Mason Jar Bioreactor

Figure 27:
FIG. 27. Illustration of hermetic embodiment of bioreactor configuration "4."

Referring now to FIG. 27A, a "hermetic" (tightly sealed against the environment) embodiment of a bioreactor according to the configuration labeled "4" in FIG. 23 is illustrated. The bioreactor was an "upside-down" bioreactor, with an upper mason jar (not pictured) disposed above a lower mason jar (FIG. 27A) and separated by a nylon membrane having a pore size of 0.45 After 10 days of growth, a biomat having a thickness of about 10 mm was produced. FIG. 27A illustrates the growth container at day with feedstock on one side of the membrane and the grown biomat on the other side of the membrane. FIG. 27B illustrates the biomat harvested at day 10, and FIG. 27C illustrates a thin section thereof for use in tensile strength testing (Example 41, infra).

Table 20 provides various characteristics of the biomat illustrated in FIG. 27B.

TABLE 20

| Characteristics of "upside down" mason jar bioreactor-grown biomat | |
|---|---|
| Area of biomat | 25.5 cm² |
| Wet biomass | 17.5 g |
| Dry biomass | 3.13 g |
| Yield (dry weight) | 1226 g/m² |
| Wet density | 0.684 g/cm³ |
| Dry density | 0.123 g/cm³ |
| Fumonisins | 0.0 ppm |
| Carbon conversion efficiency | 62.6% |

Example 41: Tensile Strength Testing of "Upside Down" Mason Jar Bioreactor-Grown Biomat A 5 cm×1 cm section of biomat illustrated in FIG. 27B was separated with a razor blade, as illustrated in FIG. 27C. The thickness of the section was recorded with a caliper, and the cut sample was placed between two glass slides such that 1 cm of the 5 cm length of the sample was pressed between the two slides, while care was taken not to damage the sample by applying excessive pressure via the slides. The glass slides were then attached to a tensile strength testing apparatus via a clip, such that the tension of the clip prevented the sample from slipping. Two additional glass slides were used to press another 1 cm length of the sample at the opposite end. A water receptacle adapted for use with the tensile strength testing apparatus was attached to the slides and filled with water at a rate of 1 mL per second until sample failure. Upon failure, the mass of the water, the receptacle, the clip, and the remaining sample were weighed together; by dividing this weight by the thickness of the sample, the tensile strength of the sample was calculated. The tensile strength of the sample of biomat produced in Example 40, as determined by this method, was 1784 grams-force per square centimeter.

Example 42: Use of "Biomembrane"

Figure 28A:
FIGS. 28A and 28B. Illustration of bioreactor utilizing "biomembrane" 3 days and 6 days after inoculation, respectively.
Figure 28B:
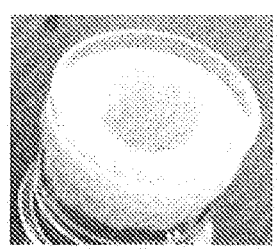

Referring now to FIGS. 28A and 28B, a typical bioreactor setup is illustrated at 3 days (FIG. 28A) and 6 days (FIG. 28B) after inoculation. Fungus was inoculated on the side of the nylon membrane (pore size 0.2 µm) opposite the feedstock, and biomats grew at a rate of approximately 1 mm per day. After an initial harvest at day 3, at which time it was observed that the nylon membrane was significantly deformed, the same membrane was reused and a biomat of approximately the same thickness grew over the following three days. At 6 days after inoculation, it was discovered that the nylon membrane had failed, but a combination of the nylon and the biomat itself continued to act as the membrane. Thus, it has been unexpectedly found that even when the initially provided membrane fails, the biomat itself can act as a "biomembrane" in the practice of the bioreactor.

Example 43: Human Waste Products as Feedstock/Growth Medium

One advantage of bioreactors of the present disclosure and methods of use thereof is that animal waste products, including but not limited to human urine and human feces, agricultural waste products and industrial waste products may be used as a feedstock or growth medium. For this Example, artificial urine medium (AUM) and artificial feces medium (AFM) were prepared according to the compositions shown in Tables 21 and 22.

TABLE 21

| AUM composition | |
| --- | --- |
| Component | Concentration (g/L) |
| Calcium chloride dihydrate | 0.37 |
| Magnesium sulfate heptahydrate | 0.49 |
| Sodium chloride | 5.2 |
| Sodium sulfate decahydrate | 3.2 |
| Citric acid | 0.4 |
| Lactic acid | 0.1 |
| Monopotassium phosphate | 0.95 |
| Dipotassium phosphate | 1.2 |
| Ammonium chloride | 1.3 |
| Urea | 10 |
| Creatinine | 0.8 |
| Yeast extract | 0.005 |
| Bacteriological peptone | 1 |
| Iron sulfate heptahydrate | 0.0012 |
| Sodium carbonate | 2.1 |
| Water | balance |

TABLE 22

| AFM composition | |
| --- | --- |
| Component | Mass fraction |
| Water | 0.8 |
| Dry baker's yeast | 0.06 |
| Microcrystalline cellulose | 0.03 |
| Psyllium | 0.035 |
| Miso paste | 0.035 |
| Oleic acid | 0.04 |

TABLE 22-continued

| AFM composition | |
| --- | --- |
| Component | Mass fraction |
| Sodium chloride | 0.004 |
| Potassium chloride | 0.004 |
| Calcium chloride | 0.002 |

Biomats were grown on various membranes in simple bioreactors, using the prepared AUM and AFM as feedstocks, in addition to samples using lignocellulosic biomass (an efficient carbon source) as a feedstock. The bioreactor yields resulting from these feedstock/membrane combinations are given in Table 23.

TABLE 23

| Bioreactor yields on AUM, AFM, and lignocellulosic biomass | | | |
| --- | --- | --- | --- |
| Membrane material and pore size | Bioreactor yield, AFM:AUM feedstock (g/m²) | Bioreactor yield, AUM feedstock (g/m²) | Bioreactor yield, lignocellulosic biomass (g/m²) |
| None | 317 | 342 | |
| PVDF, 5 µm | 274 | 359 | 247 |
| Nylon, 0.2 µm | 196 | | 145 |
| MCE, 0.2 µm | 298 | | |
| MCE, 0.45 µm | 221 | | |
| PVDF, 0.2 µm | 251 | 348 | |

Figure 30A:
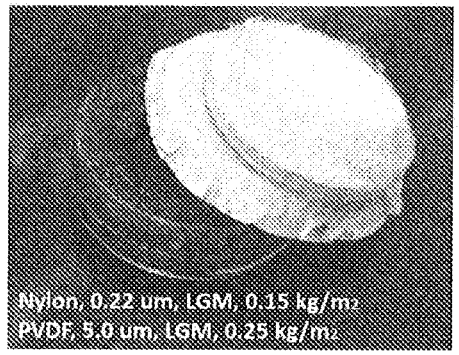
FIGS. 30A and 30B. Macroscopic and microscopic illustrations, respectively, of biomats produced in feedstock comparison test.
Figure 30B:
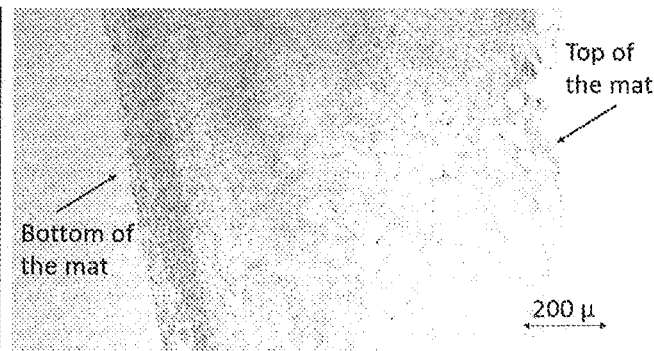

Biomats produced in these tests are illustrated in FIGS. 30A and 30B. Additionally, it was observed that biomats grown on 1:1, AFM, AUM adhered very loosely to the PVDF membranes and would simply fall off when a certain thickness/weight was attained. Thus, a self-harvesting system was envisioned where biomats would fall away from the membranes after a certain weight was attained—no need for physical/manual removal from the membrane would be necessary

Example 44: Continuous Feeding of Feedstock in Absence of Backpressure

Figure 31A:
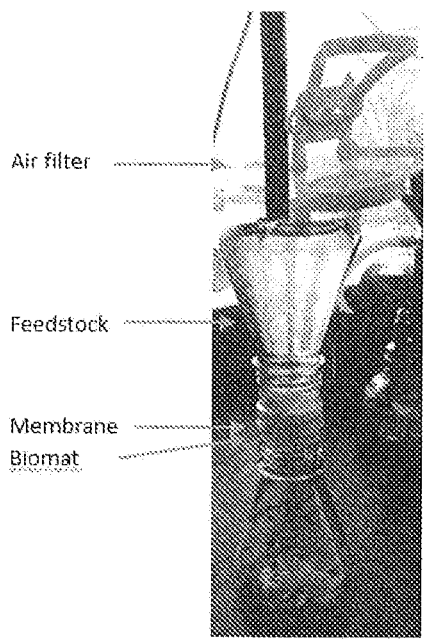
FIGS. 31A and 31B. An illustration of an embodiment of a continuously fed, backpressure-eliminating bioreactor and a generalized schematic for continuously fed, backpressure-eliminating bioreactors, respectively.
Figure 31B:
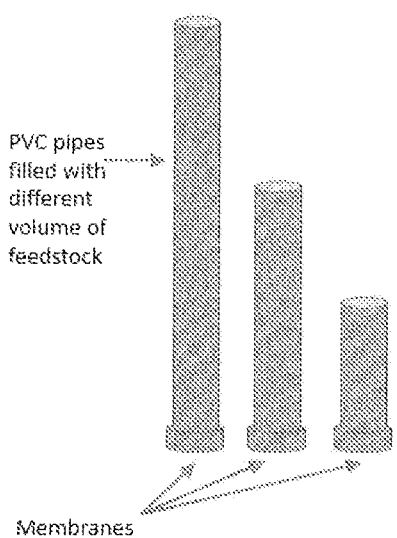

A bioreactor enabling continuous feeding of the feedstock to the bioreactor was constructed that eliminated the backpressure caused by depletion of the liquid feedstock and enabled equilibration of the liquid feedstock medium with the outside environment via a gas-permeable filter; this was accomplished by drilling a hole in the top Erlenmeyer flask and placing an air filter in the hole created thereby. This embodiment is illustrated in FIG. 31A, and a more generalized bioreactor setup is illustrated in FIG. 31B.

Use of a nylon membrane having a pore size of 0.2 µm proved ineffective in this embodiment because the membrane tended to leak. By contrast, a polypropylene membrane having a pore size of 10 µm tolerated the pressure inside the bioreactor and did not fail, crack, or leak.

Example 45: Membrane-Bag Biofilm Reactor (MBBR) System

A membrane-bag biofilm reactor (MBBR) system may provide a scalable and convenient means for producing dense usable biomass, including by using wastes and carbon substrates that are anticipated to be available, e.g., on crewed space missions or in terrestrial applications. The MBBR may provide a lightweight, compact, simple, and reusable system for culturing filamentous fungi, which may be used, by way of non-limiting example, not only as a foodstuff but in pharmaceuticals, nutraceuticals, fuels, leather analogues, textiles, and/or building materials.

Figure 32:
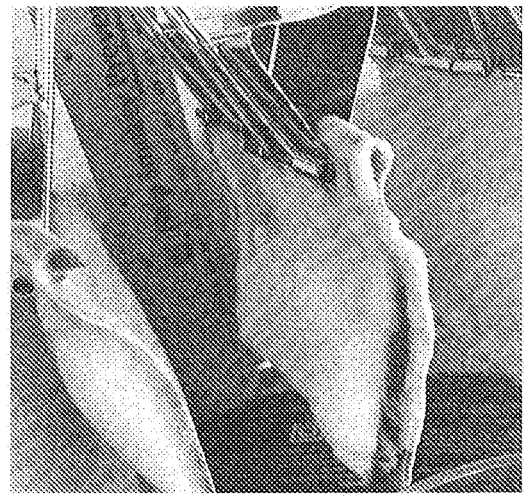
FIG. 32. Illustration of biomat growth in membrane-bag biofilm reactor.

A three-layer Gore-Tex fabric was chosen as the MBBR membrane for its durability and water-resistant and gas exchange properties. The bags were fabricated by using a heat-fluxable sealing tape to provide watertight seams, and a simple roll closure system for sealing the top of the bag and attaching it to a support was employed. The outside surface of the bags were inoculated with filamentous fungus strain MK7 and filled with a growth medium, then the tops of the bags were sealed and the bags were suspended on a rack in a sealed, temperature—and humidity—controlled box (50 cm×50 cm×70 cm, 25±1° C., approximately 95% relative humidity). After 3 days, each bag was fully covered with a layer of strain MK7 biomat displaying a thick layer of hyphae, aerial hyphae, and mycelia. Biomat growth after 5 days is illustrated in FIG. 32. By the end of the 7-day growth period, the bags were completely depleted of the glycerol feedstock, and the calculated conversion of the glycerol feedstock into dry biomat was approximately 35%, not accounting for any glycerol sorbed by the membrane fabric.

Example 46: Effect of Membrane Material and Pore Size on Biomat Growth

Tests in simple bioreactors were performed under identical conditions using four different membrane materials at five different pore sizes (20 different membranes total). The characteristics of the membranes are given in Table 24.

TABLE 24

Membrane materials and characteristics

| Specimen # | Material | Hydrophilic or hydrophobic? | Pore size, µm | Thickness, mm | Water flow rate per area, cm/min | Bubble point, kPa |
|---|---|---|---|---|---|---|
| 1 | PTFE w/ | Hydrophobic | 0.2 | 0.2 ± 0.1 | >6.2 | >140 |
| 2 | PP | | 0.45 | | >30.9 | >70 |
| 3 | backing | | 1 | | >86.6 | >24 |
| 4 | | | 3 | | >98.17 | >14 |
| 5 | | | 5 | | >196.9 | >7 |
| 6 | PP, no | Hydrophobic | 0.2 | | >18 | >14 |
| 7 | backing | | 0.45 | | >54.2 | >9 |
| 8 | | | 1 | | >120 | >4 |
| 9 | | | 3 | | >180.5 | >3.5 |
| 10 | | | 5 | | >240.7 | >3 |
| 11 | Nylon w/ | Hydrophilic | 0.2 | 0.085 – 0.14 | >4 | 310 – 410 |
| 12 | PET | | 0.45 | | >16 | 150 – 250 |
| 13 | substrate | | 1 | | >85 | 80 – 120 |
| 14 | | | 3 | | >165 | 40 – 60 |
| 15 | | | 5 | | >240 | 30 – 50 |
| 16 | PVDF w/ | Hydrophobic | 0.2 | 0.085 – 0.12 | >5 | 70 – 150 |
| 17 | PET | | 0.45 | | >10 | 40 – 80 |
| 18 | substrate | | 1 | | >20 | 25 – 35 |
| 19 | | | 3 | | >40 | 15 – 20 |
| 20 | | | 5 | | >50 | 10 – 15 |

Selected characteristics of the biomats grown on these membranes are given in Table 25.

TABLE 25

Biomat characteristics

| Specimen # | Thickness, cm | | Area, cm2 | | Wet density, g/cm3 | | Dry yield, g/cm2 | |
|---|---|---|---|---|---|---|---|---|
| | AUM | MK | AUM | MK | AUM | MK | AUM | MK |
| 1 | 0.1 | 0.2 | 4.9 | 3.14 | 1.05 | 0.71 | 84 | 261 |
| 2 | 0.2 | 0.2 | 3.14 | 9.62 | 0.96 | 0.43 | 169 | 128 |
| 3 | 0.25 | 0.1 | 4.9 | 9.62 | 0.59 | 0.62 | 245 | 113 |
| 4 | 0.3 | 0.4 | 4.9 | 9.62 | 0.75 | 0.31 | 241 | 195 |
| 5 | 0.2 | 0.5 | 3.94 | 9.62 | 1.17 | 0.28 | 203 | 165 |
| 6 | 0.2 | 0.1 | 4.52 | 9.62 | 1.03 | 0.56 | 55 | 4 |
| 7 | | 0.3 | | 9.62 | | 0.30 | | 37 |
| 8 | 0.3 | | 9.62 | 9.62 | 0.22 | | 109 | 61 |
| 9 | 0.2 | | 9.62 | 9.62 | 0.48 | | 122 | 75 |
| 10 | 0.3 | 0.6 | 9.62 | 9.62 | 0.34 | 0.36 | 79 | 213 |
| 11 | 0.5 | 0.7 | 9.62 | 9.62 | 0.404 | 0.611 | 342 | 507 |
| 12 | 0.2 | 0.55 | 9.62 | 9.62 | 0.412 | 0.380 | 150 | 298 |
| 13 | | 0.55 | | 9.62 | | 0.618 | | 532 |
| 14 | | 0.55 | | 9.62 | | 0.553 | | 435 |
| 15 | 0.4 | 0.1 | 9.62 | 9.62 | 0.368 | 0.466 | 321 | 67 |

The minimum biomat densities observed in these experiments was 0.22 g/cm 3 wet and 0.036 g/cm$^3$ dry.

Visual inspection of the specimens of this Example provided several insights. In PTFE and PP membranes, which were characterized by greater thickness and tortuosity, it appeared that significant quantities of biomass accumulated inside the membrane itself and were thus unavailable for harvesting; moreover, in PTFE membranes, the fungal inoculum did not "spread" to cover the entire surface of the membrane but had to be applied via a spray, a vacuum pump, a Q-tip, a paintbrush, or the like, and biomat did not grow across the entire membrane area as a result. Additionally, the PET-backed nylon membrane did not suffer the same structural integrity problems (cracking, failure, etc.) evidenced by the pure nylon membranes of earlier Examples. It is hypothesized that the poor results for hydrophobic PVDF with PET backed membranes was caused by the thinner, smoother membrane used for these experiments, which may have resulted in less ability for fungal bodies to get purchase on the membrane (a problem which could potentially be solved by roughening the membrane), but PVDF membranes also were characterized by the formation of a thick "slime" that requires further study. Another possibility is that hydrophobic PVDF with PET backing performance was more due to significantly lower liquid flow rates through the membranes, compared to the same thin and smooth nylon membrane (see table 24). Nylon and PVDF membranes also came out quite "clean," i.e. suitable for reuse. 0.2 hydrophobic PVDF-PET was quite clean, but 0.45, 1, 3 or 5 had slime. Hydrophylic PVDF or 5.0 did not have a slime (see data in table 19).

One further result of note is that while yields tended to increase with increasing pore size for PTFE and PP membranes, the opposite trend was observed for PET-backed nylon membranes. Without wishing to be bound by any particular theory, it is hypothesized that the hydrophilic nature of this membrane might, in large-pore embodiments, have provided conditions too "wet" for optimal biomat growth, and that the trend may be different if the membrane were "flipped" to attempt to grow the biomat on the hydrophobic surface instead.

Example 47: Tensile Strength Testing

The tensile strength of various biomat samples was tested according to the procedure described in Example 41. Biomat characteristics and testing results are given in Table 26.

TABLE 26

| | | | | | | | |
|---|---|---|---|---|---|---|---|
| | | | | Biomat characteristics | | | |
| Membrane | Medium | Membrane area, cm$^2$ | Biomat age, days | Biomat thickness, mm | Wet density, g/cm$^3$ | Test strip area | Tensile strength, gr/cm$^2$ |
| Nylon, 0.2 μm | MK | 25.5 | 10 | 10 | 0.68 | 4 cm × 0.1 cm | 1784 |
| PVDF-PET, 0.2 μm (hydrophobic) | AUM | 25.5 | 10 | 5 | 0.52 | 2 cm × 1 cm | 998 |
| PVDF, 0.2 μm (hydrophilic) | AUM | 9.62 | 7 | 5 | 0.37 | 2.6 cm × 0.9 cm | 1080 |
| Nylon-PET, 1.0 μm | MK | 9.62 | 5 | 5.5 | 0.62 | 2.4 cm × 0.8 cm | 661 |
| Nylon-PET, 0.2 μm | MK | 9.62 | 5 | 7 | 0.61 | 2.4 cm × 0.9 cm | 682 |
| Nylon-PET, 0.2 μm | AUM | 9.62 | 5 | 5 | 0.40 | 2.3 cm × 0.9 cm | 748 |

Example 48: Backpressure-Eliminating Bioreactors

Bioreactors that eliminate backpressure resulting from consumption of the feedstock, substantially conforming to the generalized schematic presented in FIG. 31A, were constructed and used to test the performance under fluid pressure of various membranes. Results of these tests are given in Table 27.

TABLE 27

| | | | | | | |
|---|---|---|---|---|---|---|
| Fluid pressure performance of various membrane types | | | | | | |
| Membrane material | Pore size, μm | Membrane hydrophilic or hydrophobic? | Backing material | Backing hydrophilic or hydrophobic? | Height of liquid column, cm | Result |
| Nylon | 0.2 | Hydrophilic | None | n/a | n/a | Immediate leaking. |
| Nylon | 0.2 | Hydrophilic | PET | Hydrophobic | n/a | Immediate leaking. |
| Polypropylene | 10.0 | Hydrophobic | None | n/a | 11 | Slow leaking, with mat growth on membrane. |
| PTFE | 0.22 | Hydrophobic | PP | Hydrophobic | 8.3 | No leaking, with mat growth on membrane. |

TABLE 27-continued

Fluid pressure performance of various membrane types

| Membrane material | Pore size, μm | Membrane hydrophilic or hydrophobic? | Backing material | Backing hydrophilic or hydrophobic? | Height of liquid column, cm | Result |
|---|---|---|---|---|---|---|
| PTFE | 0.45 | Hydrophobic | PP | Hydrophobic | 8.3 | No leaking. |
| PTFE | 1.0 | Hydrophobic | PP | Hydrophobic | 9 | No leaking, with mat growth on membrane. |
| PTFE | 3.0 | Hydrophobic | PP | Hydrophobic | n/a | Immediate leaking. |
| PTFE | 5.0 | Hydrophobic | PP | Hydrophobic | n/a | Immediate leaking. |

These results tend to indicate that hydrophilic membranes and membranes with larger pore sizes are less capable of withstanding hydrostatic pressure than small-pore hydrophobic membranes. It is hypothesized, without wishing to be bound by any particular theory, that hydrophilic membranes and large-pore membranes, which readily allow feedstock to pass through, may be more suitable for applications in which the feedstock is disposed below the membrane, whereas small-pore hydrophobic membranes may be more suitable for applications in which the feedstock is disposed above the membrane. It is also hypothesized that variations in fluid pressure may allow an operator of the bioreactor to adjust or tune biomat growth rate or other biomat characteristics, and/or facilitate in situ removal of the biomat from the membrane.

Example 49: Effect of Light Conditions on Biomat Growth

Figure 34:
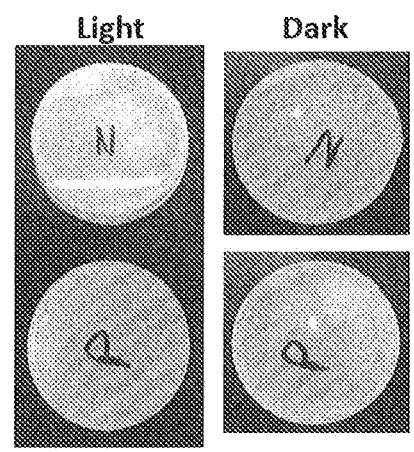
FIG. 34. Comparison of biomats grown in light and dark conditions.

Fungal strain MK7 was inoculated onto nylon and polypropylene membranes and grown into biomats in light and dark conditions. Although all mats appeared identical after 4 days of growth, by day 7 biomats grown under light conditions had begun to die, likely due to nutrient depletion in the feedstock. Biomats grown in dark conditions, by contrast, appeared healthy well after day 7, and appeared to evolve small bubbles of gas, suggesting a different metabolic pathway than that of biomats grown in light conditions. Biomats grown in dark conditions did not begin to darken and appear unhealthy until day 14. These results are illustrated in FIG. 34 ("N" denotes nylon membrane, "P" denotes polypropylene membrane.

Example 50: Comparative Protein Content

Each of several filamentous fungi were grown by at least one method selected from surface fermentation according to the present invention, submerged fermentation according to the methods of the prior art, and fruiting body (i.e. "natural") growth. In each case of surface fermentation, the carbon-to-nitrogen ratio of the liquid growth medium was 7.5. Average protein contents for each fungus grown by each method are presented in Table 28.

TABLE 28

Comparative protein content

| Fungus | Growth method | Growth medium | Protein content (wt %) |
|---|---|---|---|
| Strain MK7 | Surface | MK7-102 | 51.0 |
|  |  | R1 fructose | 51.4 |
|  | Submerged | MK7 glycerol | 34.6 |
| Sparassis crispa | Surface | Malt 001 | 46.2 |
|  | Fruiting body | n/a | 8.9 |
| Morchella conica | Surface | Malt 001 | 44.1 |
|  | Fruiting body | n/a | 34.3 |

The results of this Example demonstrate that the surface fermentation methods of the present invention produce filamentous fungus biomats having greater protein content than can be achieved by either submerged fermentation or natural growth of the fungal fruiting bodies. Even more particularly, the methods of the present invention produce biomats having protein contents of at least about 40 wt %, which for many species of filamentous fungus cannot be achieved by any previously known method.

Example 51: Mesh Solid Support 1.75 kilograms of a 1:1 sucrose:fructose carbon source in M2 media was poured into a 10"×13" inch Pyrex tray. A 0.09 m² section of a #7 polyolefin mesh (mesh size 2 mm, material believed to be LDPE) was coated with an inoculum of strain MK7 and applied to the surface of the growth medium, whereupon the tray was cultured at 27° C. for 72 hours. Initial biomat formation was observed to be more rapid on the mesh surface than on the bulk medium in the tray.

A first section of biomat was harvested from the tray by cutting around the perimeter of the polyolefin mesh, and a second section of the biomat was harvested from the tray by cutting around the periphery of the tray. It was immediately apparent that biomat harvested from the surface of the mesh (wet mass 70 g) had a much lower content of entrained liquid growth medium than the sample from the surface of the medium (wet mass 144 g).

Both biomat samples were processed by steaming for 30 minutes, followed by soaking in water at 50° C. for 15 minutes and hand pressing. The final (dried) mass of the biomat harvested from the mesh surface was 30 g (333.33 g/m²), while the final (dried) mass of the biomat harvested from the bulk medium was 24 g (266.67 g/m²). This Example thus provides evidence that yields of biomat can be improved by approximately 20% simply by providing a solid mesh as a scaffold or substrate to which biomat structures can attach.

Example 52: Refreshed Medium Experiment with King Oyster and Reishi Mushroom

The experimental procedure (including control comparison) of Example 2 was repeated, except that king oyster mushroom (*Pleurotys eryngii*) and reishi mushroom (*Ganoderma lucidum*) were used in place of strain MK7, a mesh support as in Example 51 was used, and the experiment was allowed to proceed for a period of 22 days, with measurements of total biomat growth obtained at 5, 10, and 22 days. The results are given in Table 29 (all yields are given in grams dry mass per square meter).

TABLE 29

Mushroom growth on mesh support vs. control

| Day | King oyster Refresh | King oyster Control | Reishi Refresh | Reishi Control |
|---|---|---|---|---|
| 5 | 120 | 78 | 108 | 87 |
| 10 | 238 | 143 | 239 | 129 |
| 22 | 444 | 128 | 433 | 132 |

Example 53: Medium Characteristics and Effect on Protein Content

An artificial urine medium ("AUM"), a lignocellulosic biomass medium ("LCBM"), and an MK102 medium were prepared according to the compositions in Tables 28, 29, and respectively.

TABLE 30

Artificial urine medium composition

| Component | Concentration (g/L) |
|---|---|
| Calcium chloride dihydrate | 0.37 |
| Magnesium sulfate heptahydrate | 0.49 |
| Sodium chloride | 5.2 |
| Sodium sulfate | 1.41 |
| Trisodium citrate | 0.61 |
| Lithium lactate | 0.1 |
| Bipotassium phosphate | 0.95 |
| Monopotassium phosphate | 1.2 |
| Ammonium chloride | 1.3 |
| Urea | 10 |
| Creatinine | 0.8 |
| Yeast extract | 0.005 |
| Bacteriological peptone | 1 |
| Iron sulfate heptahydrate | 2.1 |
| Water | balance |

TABLE 31

Lignocellulosic biomass composition

| Component | Concentration (g/L) |
|---|---|
| Ground hay | 100 |
| Ammonium nitrate | 10.5 |
| Urea | 3.5 |
| Calcium chloride | 1 |
| Magnesium sulfate heptahydrate | 1 |
| Bipotassium phosphate | 4 |
| EDTA-free trace | 0.4 |
| Yeast extract | 2 |
| Water | balance |

TABLE 32

MK102 medium composition

| Component | Concentration (g/L) |
|---|---|
| Ammonium nitrate | 10.5 |
| Urea | 3.5 |
| Calcium chloride | 1 |
| Magnesium sulfate heptahydrate | 1 |
| Bipotassium phosphate | 4 |
| EDTA-free trace | 0.4 |
| Glycerol | 10 |
| Yeast extract | 2 |
| Water | balance |

The media were then acidified with hydrochloric (for AUM and MK102) or sulfuric (for LCBM) acid to achieve a pH of 3.5. The ionic strength and osmolality of the media were determined, and mats were grown on each medium and then desiccated and/or dried and assayed to determine protein content. Results of these determinations are given in Table 31.

TABLE 31

Comparison of media and mats grown therefrom

| Component | Ionic strength (mmol/L) | Osmolality (mOsm) | Best yield (g/m$^2$) | Protein content |
|---|---|---|---|---|
| AUM | 308.5 | 1902 | 359 | 43.8% |
| MK102 | 296 | 1804 | 507 | 41.2% |
| LCBM | 1401.6 | 2723 | 247.4 | Not reported |

The invention claimed is:
1. A food product, comprising:
 (a) filamentous fungal biomass, consisting essentially of fungal mycelium and being free of feedstock on which the filamentous fungal biomass was grown, wherein a protein content of the filamentous fungal biomass is at least about 46 wt. %; and
 (b) a vegetarian version of a meat product.
2. The food product of claim 1, wherein the filamentous fungal biomass has been subjected to a treatment to inactivate the viability of the filamentous fungal biomass.
3. The food product of claim 2, wherein the treatment is selected from the group consisting of heating, irradiation, steaming, and combinations thereof.
4. The food product of claim 1, wherein the filamentous fungal biomass makes up between about 10 wt. % and about 50 wt. % of the food material.
5. The food product of claim 1, wherein the filamentous fungal biomass comprises size-reduced particles derived from a filamentous fungal biomat produced by surface fermentation.
6. The food product of claim 1, wherein the filamentous fungal biomass comprises particles having an average particle length of 0.05 mm to 500 mm, an average particle width of 0.03 mm to 7 mm, and an average particle height of 0.03 to 1.0 mm.
7. The food product of claim 6, wherein the average particle length is about 0.4 mm to about 500 mm and the average particle width is about 0.4 mm to about 7 mm.
8. The food product of claim 7, wherein the average particle length is about 4 mm to about 10 mm, the average particle width is about 1 mm to about 3 mm, and the average particle height is less than about 0.75 mm.
9. The food product of claim 7, wherein the average particle length is less than about 1.5 mm, the average particle width is less than about 1 mm, and the average particle height is less than about 0.75 mm.

10. The food product of claim 1, wherein the vegetarian version of a meat product is selected from the group consisting of vegetarian versions of beef, chicken, pork, and fish.

11. The food material of claim 1, wherein the filamentous fungal biomass comprises at least one filamentous fungus selected from the group consisting of *Fusarium* strain MK7 (ATCC Accession Deposit No. PTA-10698), *Fusarium venenatum, Fusarium avenaceum, Neurospora crassa, Agaricus bisporus, Boletus edulis, Cantarellus cibarius, Calvatia gigantea, Cyclocybe aegerita, Ganoderma lucidum, Grifola frondosa, Morchella* spp., *Hypsizygus tessellatus, Hypsizygus ulmarius, Laetiporus* spp., *Lentinula edodes, Pleurotus eryngii, Pleurotus ostreatus, Pholiota microspora, Sparassis crispa,* and *Tuber* spp.

12. The food product of claim 1, wherein the fungal mycelium comprises aerial hyphae.

13. The food product of claim 1, further comprising at least one additive selected from the group consisting of flavors, spices, flavor enhancers, fats, fat replacers, preservatives, sweeteners, color additives, nutrients, emulsifiers, stabilizers, thickeners, pH control agents, acidulants, leavening agents, anti-caking agents, humectants, yeast nutrients, dough strengtheners, dough conditioners, firming agents, enzyme preparations, gases, and combinations thereof.

14. The food product of claim 13, wherein the at least one additive is selected from the group consisting of flavors, spices, flavor enhancers, and sweeteners.

15. The food product of claim 13, wherein the at least one additive comprises a spice mixture selected from the group consisting of a Cajun spice mixture, a cheese spice mixture, a soy spice mixture, a vinegar spice mixture, an herb spice mixture, a sour cream and onion spice mixture, a liquid smoke spice mixture, and a vegan meat spice mixture.

16. The food product of claim 13, made by a method comprising:
    (a) contacting the filamentous fungal biomass, the vegetarian version of a meat product, and the at least one additive; and
    (b) dehydrating the filamentous fungal biomass.

17. The food product of claim 1, wherein at least one of the filamentous fungal biomass and the vegetarian version of a meat product has been subjected to tenderization.

18. The food product of claim 1, comprising all essential amino acids.

19. The food product of claim 1, wherein the filamentous fungal biomass is the source for at least about 25 wt. % of protein in the food material.

20. The food product of claim 1, wherein the filamentous fungal biomass and the vegetarian version of a meat product are the only sources of protein in the food material.

21. The food product of claim 1, wherein the filamentous fungal biomass comprises particles having an average particle size of about 75 to about 120 microns.

22. The food product of claim 21, wherein at least about 5 wt % of the particles have a particle size of at least about 180 microns and at least about 5 wt % of the filamentous fungal particles have a particle size of less than about 75 microns.

23. The food product of claim 1, wherein the filamentous fungal biomass comprises all essential amino acids.

24. The food product of claim 1, wherein the filamentous fungal biomass has a fiber content of at least about 23 wt. %.

25. The food product of claim 1, wherein the filamentous fungal biomass has a lipid content of about 6 wt. % to about 11 wt. %.

26. The food product of claim 1, wherein the food product is selected from the group consisting of a burger, a sausage, a hot dog, a chicken nugget, bacon, jerky, and a fish filet.

27. A food product, comprising:
    (a) filamentous fungal biomass, wherein the filamentous fungal biomass consists essentially of fungal mycelium and is free of feedstock on which the filamentous fungal biomass was grown; wherein the filamentous fungal biomass comprises at least about 46 wt. % protein; wherein the filamentous fungal biomass comprises fiber; and the filamentous fungal biomass has been subjected to a treatment selected from the group consisting of inactivation of viability, deactivation of enzymes, and combinations thereof;
    (b) a vegetarian version of a meat product; and
    (c) at least one additive selected from the group consisting of flavors, spices, flavor enhancers, fats, fat replacers, preservatives, sweeteners, color additives, nutrients, emulsifiers, stabilizers, thickeners, pH control agents, acidulants, leavening agents, anti-caking agents, humectants, yeast nutrients, dough strengtheners, dough conditioners, firming agents, enzyme preparations, gases, and combinations thereof.

28. The food product of claim 1, wherein the vegetarian version of a meat product comprises a protein source selected from the group consisting of egg white protein, textured vegetable protein, bulgur, potato, brown rice, almond meal, wheat gluten, and combinations thereof.

29. The food product of claim 28, wherein the vegetarian version of a meat product comprises textured vegetable protein.

30. The food product of claim 1, wherein a ratio of the filamentous fungal biomass to the vegetarian version of a meat product is 10:90 to 90:10.

* * * * *